(12) United States Patent
Sasisekharan et al.

(10) Patent No.: US 7,560,106 B2
(45) Date of Patent: *Jul. 14, 2009

(54) RATIONALLY DESIGNED HEPARINASES DERIVED FROM HEPARINASE I AND II AND METHODS OF SEQUENCING THEREWITH

(75) Inventors: Ram Sasisekharan, Bedford, MA (US); Zachary Shriver, Boston, MA (US); Dongfang Liu, Westborough, MA (US); Ganesh Venkataraman, Bedford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 310 days.

This patent is subject to a terminal disclaimer.

(21) Appl. No.: 11/191,144

(22) Filed: Jul. 27, 2005

(65) Prior Publication Data

US 2006/0105430 A1 May 18, 2006

Related U.S. Application Data

(62) Division of application No. 09/384,959, filed on Aug. 27, 1999, now Pat. No. 7,056,504.

(60) Provisional application No. 60/098,153, filed on Aug. 27, 1998.

(51) Int. Cl.
   *A61K 38/00* (2006.01)
   *C12N 9/88* (2006.01)

(52) U.S. Cl. .......................... 424/94.5; 435/2; 435/232; 435/252.33; 435/320.1; 536/23.2

(58) Field of Classification Search ........................ None
   See application file for complete search history.

(56) References Cited

U.S. PATENT DOCUMENTS

| | | | |
|---|---|---|---|
| 4,281,108 A | 7/1981 | Fussi | |
| 4,341,869 A | 7/1982 | Langer, Jr. et al. | |
| 4,373,023 A | 2/1983 | Langer et al. | |
| 4,396,762 A | 8/1983 | Langer et al. | |
| 4,443,545 A | 4/1984 | Langer, Jr. et al. | |
| 4,551,296 A | 11/1985 | Kavesh et al. | |
| 4,745,105 A | 5/1988 | Griffin et al. | |
| 4,757,056 A | 7/1988 | Van Gorp et al. | |
| 4,816,446 A | 3/1989 | Feller et al. | |
| 4,830,013 A | 5/1989 | Maxwell | |
| 4,928,694 A | 5/1990 | Maxwell | |
| 4,942,156 A | 7/1990 | Foley et al. | |
| 4,990,502 A | 2/1991 | Lormeau et al. | |
| 5,010,063 A | 4/1991 | Piani et al. | |
| 5,039,529 A | 8/1991 | Bergendal et al. | |
| 5,106,734 A | 4/1992 | Nielsen | |
| 5,145,778 A | 9/1992 | Bellamy et al. | |
| 5,152,784 A | 10/1992 | Tsilibary | |
| 5,164,378 A | 11/1992 | Conti et al. | |
| 5,169,772 A | 12/1992 | Zimmerman et al. | |
| 5,204,323 A | 4/1993 | Findlay et al. | |
| 5,252,339 A | 10/1993 | Cristofori et al. | |
| 5,262,325 A | 11/1993 | Zimmermann et al. | |
| 5,290,695 A | 3/1994 | Morikawa et al. | |
| 5,338,677 A | 8/1994 | Zimmermann et al. | |
| 5,362,645 A | 11/1994 | Bellamy et al. | |
| 5,389,539 A | 2/1995 | Sasisekharan et al. | |
| 5,453,171 A | 9/1995 | Ma et al. | |
| 5,455,162 A | 10/1995 | Bellamy et al. | |
| 5,474,987 A | 12/1995 | Cohen et al. | |
| 5,567,417 A | 10/1996 | Sasisekharan et al. | |
| 5,569,366 A | 10/1996 | Chen et al. | |
| 5,569,600 A | 10/1996 | Sasisekharan et al. | |
| 5,576,304 A | 11/1996 | Kakkar et al. | |
| 5,599,801 A | 2/1997 | Branellec et al. | |
| 5,607,859 A | 3/1997 | Biemann et al. | |
| 5,618,917 A | 4/1997 | Toback et al. | |
| 5,619,421 A | 4/1997 | Venkataraman et al. | |
| 5,681,733 A | 10/1997 | Su et al. | |
| 5,687,090 A | 11/1997 | Chen et al. | |
| 5,714,376 A | 2/1998 | Sasisekharan et al. | |
| 5,744,515 A | 4/1998 | Clapper | |
| 5,752,019 A | 5/1998 | Rigoutsos et al. | |
| 5,753,445 A | 5/1998 | Fillit et al. | |
| 5,759,767 A | 6/1998 | Lakowicz et al. | |
| 5,763,427 A | 6/1998 | Weitz et al. | |
| 5,767,269 A | 6/1998 | Hirsh et al. | |

(Continued)

FOREIGN PATENT DOCUMENTS

EP 0 140 781 5/1985

(Continued)

OTHER PUBLICATIONS

[No Author Listed] MIT News Office. "MIT Tool Impacts Multi-Billion Dollar Drug." Online at http://www.sciencedaily.com. Printed Sep. 21, 2000.

(Continued)

*Primary Examiner*—Richard G Hutson
(74) *Attorney, Agent, or Firm*—Wolf, Greenfield & Sacks, P.C.

(57) ABSTRACT

Modified heparinases having altered binding specificity and activity are provided. Isolated nucleic acids encoding the same as well as vectors and host cells are provided. Methods for using the modified heparinases are also provided.

13 Claims, 4 Drawing Sheets

U.S. PATENT DOCUMENTS

| | | | |
|---|---|---|---|
| 5,795,875 A | 8/1998 | Holme et al. |
| 5,808,021 A | 9/1998 | Holme et al. |
| 5,824,299 A | 10/1998 | Luster et al. |
| 5,830,726 A | 11/1998 | Sasisekharan et al. |
| 5,856,928 A | 1/1999 | Yan |
| 5,879,713 A | 3/1999 | Roth et al. |
| 5,919,693 A | 7/1999 | Su et al. |
| 5,922,358 A | 7/1999 | Doutremepuich et al. |
| 5,952,653 A | 9/1999 | Covey et al. |
| 5,968,822 A | 10/1999 | Pecker et al. |
| 5,990,097 A | 11/1999 | Kennedy |
| 5,993,846 A | 11/1999 | Friedman et al. |
| 5,997,863 A | 12/1999 | Zimmermann et al. |
| 6,013,628 A | 1/2000 | Skubitz et al. |
| 6,190,875 B1 | 2/2001 | Ben-Artzi et al. |
| 6,217,863 B1 | 4/2001 | Godavarti et al. |
| 6,268,146 B1 | 7/2001 | Shultz et al. |
| 6,291,439 B1 | 9/2001 | Klock |
| 6,309,853 B1 | 10/2001 | Friedman et al. |
| 6,333,051 B1 | 12/2001 | Kabanov et al. |
| 6,597,996 B1 | 7/2003 | Venkataraman et al. |
| 6,642,363 B1 | 11/2003 | Mooney et al. |
| 6,734,288 B2 | 5/2004 | Filvaroff et al. |
| 6,869,789 B2 | 3/2005 | Liu et al. |
| 6,962,699 B2 | 11/2005 | Pojasek et al. |
| 7,056,504 B1 | 6/2006 | Sasisekharan et al. |
| 7,083,937 B2 | 8/2006 | Sasisekharan et al. |
| 7,105,334 B2 | 9/2006 | Pojasek et al. |
| 7,110,889 B2 | 9/2006 | Venkataraman et al. |
| 7,117,100 B2 | 10/2006 | Venkataraman et al. |
| 7,129,335 B2 | 10/2006 | Pojasek et al. |
| 7,139,666 B2 | 11/2006 | Venkataraman et al. |
| 7,247,445 B2 | 7/2007 | Sasisekharan et al. |
| 7,270,815 B2 | 9/2007 | Sasisekharan et al. |
| 2002/0122793 A1 | 9/2002 | Liu et al. |
| 2002/0128225 A1 | 9/2002 | Liu et al. |
| 2002/0169143 A1 | 11/2002 | Sasisekharan et al. |
| 2003/0008820 A1 | 1/2003 | Kwan et al. |
| 2003/0099628 A1 | 5/2003 | Liu et al. |
| 2003/0191587 A1 | 10/2003 | Venkataraman et al. |
| 2004/0091471 A1 | 5/2004 | Myette et al. |
| 2004/0091472 A1 | 5/2004 | Pojasek et al. |
| 2004/0092037 A1 | 5/2004 | Sasisekharan et al. |
| 2004/0197933 A1 | 10/2004 | Venkataraman et al. |
| 2004/0204869 A1 | 10/2004 | Venkataraman et al. |
| 2005/0037376 A1 | 2/2005 | Sasisekharan et al. |
| 2005/0214276 A9 | 9/2005 | Myette et al. |
| 2005/0227320 A1 | 10/2005 | Pojasek et al. |
| 2005/0233402 A1 | 10/2005 | Liu et al. |
| 2005/0233419 A1 | 10/2005 | Pojasek et al. |
| 2006/0024664 A1 | 2/2006 | Sasisekharan et al. |
| 2006/0057638 A1 | 3/2006 | Bosques et al. |
| 2006/0067927 A1 | 3/2006 | Chandrasekaran et al. |
| 2006/0067928 A1 | 3/2006 | Liu et al. |
| 2006/0078959 A1 | 4/2006 | Prabhakar et al. |
| 2006/0083711 A1 | 4/2006 | Berry et al. |
| 2006/0105430 A1 | 5/2006 | Sasisekharan et al. |
| 2006/0127950 A1 | 6/2006 | Bosques et al. |
| 2006/0154894 A1 | 7/2006 | Berry et al. |
| 2006/0177885 A1 | 8/2006 | Myette et al. |
| 2006/0177910 A1 | 8/2006 | Myette et al. |
| 2006/0177911 A1 | 8/2006 | Myette et al. |
| 2006/0182734 A1 | 8/2006 | Liu et al. |
| 2006/0183713 A1 | 8/2006 | Liu et al. |
| 2006/0183891 A1 | 8/2006 | Myette et al. |
| 2006/0292130 A1 | 12/2006 | Sasisekharan et al. |
| 2006/0292655 A1 | 12/2006 | Sasisekharan et al. |
| 2006/0292673 A1 | 12/2006 | Sasisekharan et al. |
| 2007/0004012 A1 | 1/2007 | Sasisekharan et al. |
| 2007/0020243 A1 | 1/2007 | Sengupta et al. |
| 2007/0065424 A1 | 3/2007 | Pojasek et al. |
| 2007/0065921 A1 | 3/2007 | Sasisekharan et al. |
| 2007/0066769 A1 | 3/2007 | Venkataraman et al. |
| 2007/0148157 A1 | 6/2007 | Prabhakar et al. |
| 2007/0148158 A1 | 6/2007 | Sasisekharan et al. |
| 2007/0148740 A1 | 6/2007 | Prabhakar et al. |
| 2007/0161073 A1 | 7/2007 | Sasisekharan et al. |
| 2007/0202563 A1 | 8/2007 | Prabhakar et al. |
| 2007/0224670 A1 | 9/2007 | Prabhakar et al. |
| 2008/0071148 A1 | 3/2008 | Bosques et al. |

FOREIGN PATENT DOCUMENTS

| | | |
|---|---|---|
| EP | 0 114 589 B1 | 9/1987 |
| EP | 0 244 236 A2 | 11/1987 |
| EP | 0 394 971 A1 | 10/1990 |
| EP | 0 433 225 A1 | 11/1990 |
| EP | 0 557 887 A2 | 2/1993 |
| EP | 0 342 215 B1 | 8/1993 |
| EP | 0 370 958 B1 | 7/1994 |
| WO | WO 89/12692 A1 | 12/1989 |
| WO | WO 92/01003 A1 | 1/1992 |
| WO | WO 92/17203 A1 | 10/1992 |
| WO | WO 93/05167 A1 | 3/1993 |
| WO | WO 93/08289 | 4/1993 |
| WO | WO 93/10450 A1 | 5/1993 |
| WO | WO 93/15406 A1 | 8/1993 |
| WO | WO 93/19096 | 9/1993 |
| WO | WO 93/19734 A1 | 10/1993 |
| WO | WO 94/12618 A1 | 6/1994 |
| WO | WO 94/21689 | 9/1994 |
| WO | WO 95/13830 A1 | 5/1995 |
| WO | WO 95/34635 | 12/1995 |
| WO | WO 96/01648 A1 | 1/1996 |
| WO | WO 97/06783 A1 | 2/1997 |
| WO | WO 97/11684 A1 | 4/1997 |
| WO | WO 97/16556 | 5/1997 |
| WO | WO 97/35562 A1 | 10/1997 |
| WO | WO 98/04902 A1 | 2/1998 |
| WO | WO 98/31346 A1 | 7/1998 |
| WO | WO 00/12726 A2 | 3/2000 |
| WO | WO 00/65521 A2 | 11/2000 |
| WO | WO 01/66772 | 9/2001 |
| WO | WO 02/23190 | 3/2002 |
| WO | WO 02/32406 | 4/2002 |
| WO | WO 02/077199 | 10/2002 |
| WO | WO 03/102160 | 12/2003 |
| WO | WO 2004/055491 | 7/2004 |
| WO | WO 2004/062592 | 7/2004 |
| WO | WO 2004/069152 | 8/2004 |
| WO | WO 2005/087920 | 9/2005 |
| WO | WO 2005/110438 | 11/2005 |
| WO | WO 2005/111627 | 11/2005 |
| WO | WO 2006/076627 | 7/2006 |
| WO | WO 2006/083328 | 8/2006 |
| WO | WO 2006/088491 | 8/2006 |
| WO | WO 2006/105313 A2 | 10/2006 |
| WO | WO 2006/105315 A2 | 10/2006 |
| WO | WO 2007/044471 A2 | 4/2007 |
| WO | WO 2007/120478 A2 | 10/2007 |

OTHER PUBLICATIONS

Alderman et al., "Continuous Subcutaneous Heparin Infusion for Treatment . . . ", 1995, 29:710-713.

Ameer et al., "Ex vivo evaluation of a Taylor-Couette flow, immobilized heparinase I device for clinical application," *PNAS*, Mar. 1999, 96:2350-55.

Ameer et al., "A New Approach to Regional Heparinization: Design and Development of a Novel Immobilized Heparinase Device", *Blood Purification Meeting Information: The International Conference on Continuous Renal Replacement Therapies*, 16(2): 107-118, 1998. Abstract Only.

Baumann et al., "Three-dimensional structure of the alkaline protease of *Pseudomonas aeruginosa*: a calcium binding parallel beta roll motif", *The EMBO Journal*, vol. 12, No. 9, pp. 3357-3364, 1993.

Bernstein et al., *Methods in Enzymology*, (1988),137:515-529.

Berry et al., "Distinct Heparan Sulfate Glycosaminoglycans are Responsible for Mediating Fibroblast Growth Factor-2 Biological Activity Through Different Fibroblast Growth Factor Receptors", *The FASEB Journal Online*, Article #: 10.1096/fj.00-0661fje: 1-19, 2001.

Biemann, "Four Decades of Structure Determination by Mass Spectrometry: From Alkaloids to Heparin", *J. Am. Soc. Mass. Spectrom.*, 13: 1254-1272, 2002.

Bruce et al., *Flavobacterium heparinum* 6-O-sulphatase for N-substituted glucosamine 6-O-sulphate. Eur J Biochem. Oct. 1, 1985;152(1):75-82.

Cardin et al., *Arteriosclerosis*, (1989), 9:21-32.

Carlson et al., "Behavior of Antithrombin III Isoforms on Immobilized Heparins: Evidence that the Isoforms Bind to Different Numbers of Low-affinity Heparin Sites", *The Journal of Biological Chemistry*, 263(5): 2187-2194, 1988.

Chuang et al., Determination of the primary structures of heparin- and heparan sulfate-derived oligosaccharides using band-selective homonuclear-decoupled two-dimensional 1H NMR experiments. Anal Chem. May 15, 2001;73(10):2310-6.

Claverie et al., "Information Enhancement Methods for Large Scale Sequence Analysis", *Computers Chem.*, 17(2): 191-201, 1993.

Cohen, The Parallel β Helix of Pectate Lyase C: Something to Sneeze At, *Science*, vol. 260, Jun. 4, 1993, pp. 1444-1445.

Comfort et al., Immobilized enzyme cellulose hollow fibers: III physical properties and in vitro biocompatibility. Biotechnology and Bioengineering. 1989;34:1383-1390.

Coulombe et al., "Elucidating the early stages of keratin filament assembly," *J. Cell. Biol.*, Jul. 1990, 111:153-169.

Crum et al., "A New Class of Steroids Inhibits Angiogenesis in the Presence of Heparin or a Heparin Fragment", *Science*, 230: 1375-1378, 1985.

Desai et al., Specificity studies on the heparin lyases from *Flavobacterium heparinum*. Biochemistry. Aug. 17, 1993;32(32):8140-5.

Dietrich et al., Enzymic degradation of heparin. A glucosaminidase and a glycuronidase from *Flavobacterium heparinum*. Biochemistry. May 1969;8(5):2089-94.

Dietrich et al., Enzymic degradation of heparin. A sulphamidase and a sulphoesterase from *Flavobacterium heparinum*. Biochem. J. Jan. 1969;111(1):91-5.

Dietrich et al., Sequential degradation of heparin in *Flavobacterium heparinum*. Purification and properties of five enzymes involved in heparin degradation. J Biol Chem. Sep. 25, 1973;248(18):6408-15.

Dull et al., "Lung Endothelial Heparan Sulfates Mediate Cationic Peptide-induced Barrier Dysfunction: A New Role for the Glycocalyx", *Am. J. Physiol. Lung Cell Mol. Physiol.*, 285: L986-995, 2003.

Edwards et al., "Large Porous Particles for Pulmonary Drug Delivery", *Science Reprint Series*, 276: 1868-1871, 1997.

Edwards et al., "Recent Advances in Pulmonary Drug Delivery Using Large, Porous Inhaled Particles", *J. Appl. Physiol.*, 85(2): 379-385, 1998.

Enriquez-Harris et al., "Growth Factors and the Extracellular Matrix", *Meeting Report*, Trends in Cell Biology, 1994.

Ernst et al., "Expression in *Escherichia coli*, Purification and Characterization of Heparinase I from *Flavobacterium heparinum*", *Biochem. J.*, 315: 589-597, 1996.

Ernst et al., "Enzymatic Degradation of Glycosaminoglycans", *Critical Reviews in Biochemistry and Molecular Biology*, 30(5): 387-444, 1995.

Ernst et al., "Direct Evidence for a Predominantly Exolytic Processive Mechanism for Depolymerization of Heparin-like Glycosaminoglycans by Heparinase I", *Proc. Natl. Acad. Sci. USA*, 95: 4182-4187, 1998.

Feingold et al., "Conformational aspects of the reaction mechanisms of polysaccharide lyases and epimerases", *FEBS Letters*, vol. 223, No. 2, Nov. 1987, pp. 207-211.

Feldman et al., "Identification of a linear heparin binding domain for human respiratory syncytial virus attachment glycoprotein G," *J. of Virology*, Aug. 1999, 73(8):6610-17.

Franklin et al, "*Pseudomonas aeruginosa* AlgG is a Polymer Level Alginate C5-Mannuronan Epimerase", *Journal of Bacteriology*, vol. 176, No. 7, Apr. 1994, p. 1821-1830.

Folkman et al., "Angiogenesis Inhibition and Tumor Regression Caused by Heparin or a Heparin Fragment in the Presence of Cortisone", *Science*, 221:719-725, 1983.

Gacesa, "Alginate-modifying enzymes—A proposed unified mechanism of action for the lyases and epimerases", *FEBS Letters*, vol. 212, No. 2, Feb. 1987, pp. 199-202.

Gioldassi et al., "Determination of Phosphorylated and Sulfated Linkage-region Oligosaccharides in Chondroitin / Dermatan and Heparan Sulfate Proteoglycans by High Performance Liquid Chromatography", *J. Liq. Chrom. & Rel. Technol.*, 22(13): 1997-2007, 1999.

Godavarti et al., "Heparinase I from *Flavobacterium heparinum*. Identification of a Critical Histidine Residue Essential for Catalysis As Probed by Chemical Modification and Site-Directed Mutagensis" *Biochemistry*, 1996, 35, 6846-6852.

Godavarti et al., "Heparinase III from *Flavobacterium heparinum*: Cloning and Recombinant Expression in *Escherichia coli*", *Biochemical and Biophysical Research Communications*, 225(3): 751-758, 1996.

Godavarti et al., "A Comparative Analysis of the Primary Sequences and Characteristics of Heparinases I, II, and III from *Flavobacterium heparinum*", *Biochemical and Biophysical Research Communications*, 229(3): 770-777, 1996.

Godvarti et al., "Heparinase I from *Flavobacterium heparinum*: Role of Positive Charge in Enzymatic Activity", *The Journal of Biological Chemistry*, 273(1): 248-255, 1998.

Gu et al., Purification, characterization and specificity of chondroitin lyases and glycuronidase from *Flavobacterium heparinum*. Biochem J. Dec. 1, 1995;312 ( Pt 2):569-77.

Guerrini et al., "A Novel Computational Approach to Integrate NMR Spectroscopy and Capillary Electrophoresis for Structure Assignment of Heparin and Heparan Sulfate Oligosaccharides", *Glycobiology*, 12(11): 713-719, 2002.

Harenberg et al., "Anticoagulant Effects and Tissue Factor Pathway Inhibitor after Intrapulmonary Low-Molecular-Weight Heparin", *Blood Coagulation and Fibrinolysis*, 7: 477-483, 1996.

Hart, "Glycosylation", *Current Opinion in Cell Biology*, 1992, 4:1017-1023.

Hayes, "Prototeins", *American Scientist, the Magazine of Sigma Xi, the Scientific Research Society*, 86(3): 216-221, 1998.

Higuchi et al., "PCR Protocols: A Guide to Methods and Applications", *Academic Press, Inc.* NY, (1990), 177-183.

Horner et al., "Heterogeneity of Rat Skin Heparin Chains with High Affinity for Antithrombin", *Biochem. J.*, 244: 693-698, 1987.

Huang et al., "Low-Molecular-Weight Heparins", *Coagulation Disorders*, vol. 12, No. 6, Dec. 1998, pp. 1251-1277.

Hovingh et al., Specificity of flavobacterial glycuronidases acting on disaccharides derived from glycosaminoglycans. Biochem J. Aug. 1, 1977;165(2):287-93.

Jackson et al., "Glycosaminoglycans: Molecular Properties, Protein Interactions, and Role in Physiological Processes", *Reviews*, vol. 71, No. 2, Apr. 1991, pp. 481-539.

Johnson et al., "Endothelial Cells Preparing to Die by Apoptosis Initiate a Program of Transcriptome and Glycome Regulation", *The FASEB Journal*, 18: 188-190, 2004.

Kakkar et al., Venous Thromboembolism and Cancer, 1998, 675-687.

Kanabrocki et al., "Heparin as a Therapy for Atherosclerosis: Preliminary Observations on the Intrapulmonary Administration of Low-Dose Heparin in the Morning Versus Evening Gauged by its Effect on Blood Variables", *Chronobiology International*, 8(3): 210-233, 1991.

Kanabrocki et al., "A Quest for the Relief of Atherosclerosis: Potential Role of Intrapulmonary Heparin—A Hypothesis", *Quarterly Journal of Medicine, New Series*, 83(300): 259-282, 1992.

Keiser et al., "Direct Isolation and Sequencing of Specific Protein-binding Glycosaminoglycans", *Nature Medicine*, 7(1): 123-128, 2001.

Kishibe et al., "Structural Requirements of Heparan Sulfate for the Binding to the Tumor-derived Adhesion Factor/ Angiomodulin that Induces Cord-like Structures to ECV-304 Human Carcinoma Cells", *The Journal of Biological Chemistry*, 275(20): 15321-15329, 2000.

Kreitz et al., "Controlled Delivery of Therapeutics from Microporous Membranes. II. In vitro Degradation and Release of Heparin-loaded Poly (D,L-lactide-*co*-glycolide)", *Biomaterials*, 18(24): 1645-1651, 1997.

Kretsinger et al., Structure and evolution of calcium-modulated proteins. CRC Crit Rev Biochem. 1980;8(2):119-74. Review.

Lee et al., "Mannose receptor-mediated regulation of serum glycoprotein homeostasis," *Science*, Mar. 8, 2002, 295:1898-1901.

Lewin et al., "Cells Obey the Laws of Physics & Chemistry", *GENES V*, 1994, p. 13.

Leckband et al., *Biotech Bioeng.*, (1991), 37:227-237.

Leckband et al., "Characterization of the Active Site of Heparinase", *Abstracts of Papers Part 1: Fourth Chemical Congress of North America*, 202(1): a56, 1991.

Linhardt et al., Polysaccharide lyases. Appl Biochem Biotechnol. Apr. 1986;12(2):135-76.

Linhardt et al., Examination of the substrate specificity of heparin and heparan sulfate lyases. Biochemistry. Mar. 13, 1990;29(10):2611-7.

Linhardt et al., "Production and Chemical Processing of Low Molecular Weight Heparins," *Seminars in Thrombosis and Hemostasis*, vol. 25, Suppl. 3, 1999, pp. 5-16.

Linker et al., The enzymatic degradation of heparin and heparitin sulfate. I. The fractionation of a crude heparinase from flavobacteria. J Biol Chem. Oct. 1965;240(10):3724-8.

Liu, Dongfang, et al., "The Calcium-binding Sites of Heparinase I from *Flavobacterium heparinum* are Essential for Enzymatic Activity", *The Journal of Biological Chemistry*, 274(7): 4089-4095, 1999.

Liu, Dongfang, et al., "Dynamic Regulation of Tumor Growth and Metastasis by Heparan Sulfate Glycosaminoglycans", *Seminars in Thrombosis and Hemostasis*, 28(1): 67-78, 2002.

Liu, Dongfang, et al., "Tumor Cell Surface Heparan Sulfate as Cryptic Promoters or Inhibitors of Tumor Growth and Metastasis", *PNAS*, 99(2): 568-573, 2002.

Liu, Jian, et al., "Strategy for the Sequence Analysis of Heparin", *Glycobiology*, 5(8): 765-774, 1995.

Liu, Jian, et al., "Characterization of a Heparan Sulfate Octasaccharide that Binds to Herpes Simplex Virus Type 1 Glycoprotein D", *The Journal of Biological Chemistry*, 277(36): 33456-33467, 2002.

Liu, Jian, et al., "Heparan Sulfate D-Glucosaminyl 3-*O*-Sulfotransferase -3A Sulfates *N*-Unsubstituted Glucosamine Residues", *The Journal of Biological Chemistry*, 274(53): 38155-38162, 1999.

Lohse et al., "Purification and Characterization of Heparin Lyases from *Flavobacterium heparinum*," *J. Biol. Chem.*, 267(34):24347-24355, 1992.

Lustig et al., "Alternative Splicing Determines the Binding of Platelet-Derived Growth Factor (PDGF-AA) to Glycosaminoglycans", *Biochemistry*, vol. 35, No. 37 1996, pp. 12077-12085.

Marciniak, "Differential Role of Fractionated Heparin in Antithrombin-III Proteolysis", *Blood*, 59(3): 576-581, 1982.

McLean et al., "Enzymic Removal of 2-*O*-Sulphato-$\Delta_{4,5}$-Glycuronic Acid Residues from Heparin Oligosaccharides", *Proc. of the 7$^{th}$ Int'l. Symposium of Glycoconjugates*, p. 68-69, 1983.

McLean et al., *Flavobacterium heparinum* 2-O-sulphatase for 2-O-sulphato-delta 4,5-glycuronate-terminated oligosaccharides from heparin. Eur J Biochem. Dec. 17, 1984;145(3):607-15.

Monagle et al., Covalent heparin cofactor II-heparin and heparin cofactor II-dermatan sulfate complexes. Characterization of novel anticoagulants. J Biol Chem. Dec. 11, 1998;273(50):33566-71.

Murphy et al., "Basic Fibroblast Growth Factor Binding and Processing by Human Glioma Cells", *Molecular and Cellular Endocrinology*, 114: 193-203, 1995.

Myette et al., "The Heparin / Heparan Sulfate 2-*O*-Sulfatase from *Flavobacterium heparinum*", *The Journal of Biological Chemistry*, 278(14): 12157-12166, 2003.

Myette et al., "Molecular Cloning of the Heparin / Heparan Sulfate $\Delta$4,5 Unsaturated Glycuronidase from *Flavobacterium heparinum*, its Recombinant Expression in *Escherichia coli*, and Biochemical Determination of its Unique Substrate Specificity", *Biochemistry*, 41(23): 7424-7434, 2002.

Myette et al., "Expression in *Escherichia coli*, Purification and Kinetic Characterization of Human Heparan Sulfate 3-*O*-Sulfotransferase-1", *Biochemical and Biophysical Research Communications*, 290(4): 1206-1213, 2002.

Natke et al., "Heparinase Treatment of Bovine Smooth Muscle Cells Inhibits Fibroblast Growth Factor-2 Binding to Fibroblast Growth Factor Receptor but Not FGF-2 Mediated Cellular Proliferation", *Angiogenesis*, 3: 249-257, 1999.

Nesheim et al., "Dependence of Antithrombin III and Thrombin Binding Stoichiometries and Catalytic Activity on the Molecular Weight of Affinity-purified Heparin", *The Journal of Biological Chemistry*, 261(7): 3214-3221, 1986.

Padera et al., "FGF-2/ Fibroblast Growth Factor Receptor/ Heparin-like Glycosaminoglycan Interactions: A Compensation Model for FGF-2 Signaling", *The FASEB Journal*, 13(13): 1677-1687, 1999.

Pixley et al., "Preparation of Highly Stable Antithrombin-sepharose and Utilization for the Fractionation of Heparin", *Thrombosis Research*, 26(2): 129-133, 1982.

Pojasek et al., "Histidine 295 and Histidine 510 are Crucial for the Enzymatic Degradation of Heparan Sulfate by Heparinase III", *Biochemistry*, 39(14): 4012-1019, 2000.

Pojasek et al., "Biochemical Characterization of the Chondroitinase B Active Site", *The Journal of Biological Chemistry*, 277(34): 31179-31186, 2002.

Pojasek et al., "Recombinant Expression, Purification, and Kinetic Characterization of Chondroitinase AC and Chondroitinase B from *Flavobacterium heparinum*", *Biochemical and Biophysical Research Communications*, 286(2): 343-351, 2001.

Pope et al., Analysis of heparan sulfate oligosaccharides by nano-electrospray ionization mass spectrometry. Glycobiology. Jun. 2001;11(6):505-13.

Raman et al., "Identification of Structural Motifs and Amino Acids within the Structure of Human Heparan Sulfate 3-*O*-Sulfotransferase that Mediate Enzymatic Function", *Biochemical and Biophysical Research Communications*, 290(4): 1214-1219, 2002.

Raman et al., "The Heparin / Heparan Sulfate 2-*O*-Sulfatase from *Flavobacterium heparinum*: A Structural and Biochemical Study of the Enzyme Active Site and Saccharide Substrate Specificity", *Journal of Biological Chemistry*, 278(14): 12167-12174, 2003.

Rhomberg et al., "Mass Spectrometric Sequencing of Heparin and Heparan Sulfate Using Partial Digestion with Heparinases", *45$^{th}$ Annual Conference of Mass Spectrometry Allied Topics*, p. 1026-1027, 1997.—Abstract Only.

Rhomberg, Andrew J., "Mass Spectrometric and Capillary Electrophoretic Investigation of Heparin, Heparinases, and Related Compounds", *MIT (Department of Chemistry)*, 1998. Thesis.

Rhomberg et al., "Mass Spectrometric and Capillary Electrophoretic Investigations of the Enzymatic Degradation of Heparin-like Glycosaminoglycans", *Proc. Natl. Acad. Sci. USA*, 95: 4176-4181, 1998.

Rhomberg et al., "Mass Spectrometric Evidence for the Enzymatic Mechanism of the Depolymerization of Heparin-like Glycosaminoglycans by Heparinase II", *Proc. Natl. Acad. Sci. USA*, 95: 12232-12237, 1998.

Rudd et al., "Oligosaccharide Sequencing Technology", *Nature*, 388: 205-207, 1997.

Sampaio et al., Effect of monensin on the sulfation of heparan sulfate proteoglycan from endothelial cells. J Cell Biochem. Sep. 1992;50(1):103-10.

Sasisekharan et al., *.Natl. Acad. Sci.*, (1993), 90:3660-3664.

Sasisekharan et al., *Proc. Natl. Acad. Sci.*, (1994), 91:1524-1528.

Sasisekharan et al., "Heparinase I from *Falbobacterium heparinum*", *The Journal of Biological Chemistry*, vol. 271, No. 6, Issue Feb. 9, pp. 3124-3131.

Sasisekharan et al., "Heparinase I from *Flavobacterium heparinum*" The Role of the Cysteine Residue in Catalysis as Probed by Chemical Modification and Site-Directed Mutagenesis, Biochemistry, vol. 34, No. 44, 1995, pp. 14441-14448.

Sasisekharan et al., "Roles of Heparan-sulfate Glycosaminoglycans in Cancer", *Nature Reviews*, 2: 521-528, 2002.

Sasisekharan et al., "Heparin and Heparan Sulfate: Biosynthesis, Structure and Function", *Current Opinions in Biological Chemistry*, 4(6): 626-631, 2000.

Shriver, Z.. et al., "Heparinase II from *Flavobacterium hepainum*: Role of histidine residues in enzymatic activity as probed by chemical modification and site-directed mutagenesis," *Journal of Biological Chemistry*, vol. 273, No. 36, 1998, pp. 10160-10167.

Shriver, Z.. et al., "Heparinase II from *Flavobacterium hepainum*: Role of cysteine in enzymatic activity as probed by chemical modification and site-directed mutagenesis," *Journal of Biological Chemistry*, vol. 273, No. 17, 1998, pp. 22904-22912.

Shriver et al., "Biochemical Investigations and Mapping of the Calcium-binding Sites of Heparinase I from *Flavobacterium heparinum*", *The Journal of Biological Chemistry*, 274(7): 4082-4088, 1999.

Shriver et al., "Sequencing of 3-O Sulfate Containing Heparin Decasaccharides with a Partial Antithrombin III Binding Site", *PNAS*, 97(19): 10359-10364, 2000.

Shriver et al., "Cleavage of the Antithrombin III Binding Site in Heparin by Heparinases and its Implication in the Generation of Low Molecular Weight Heparin", *PNAS*, 97(19): 10365-10370, 2000.

Shriver et al., "Emerging Views of Heparan Sulfate Glycosaminoglycan Structure / Activity Relationships Modulating Dynamic Biological Functions", *TCM*, 12(2): 71-77, 2002.

Su et al., *Appl. Environ. Microbiol*. 62(8):2723-34, 1996.

Sugahara et al., Novel sulfated oligosaccharides containing 3-O-sulfated glucuronic acid from king crab cartilage chondroitin sulfate K. Unexpected degradation by chondroitinase ABC. J Biol Chem. Oct. 25, 1996;271(43):26745-54.

Sundaram et al., "Rational Design of Low-molecular Weight Heparins with Improved In vivo Activity", *PNAS*, 100(2): 651-656, 2003.

Taylor et al., "Protamine is an Inhibitor of Angiogenesis", *Nature*, 297: 307-312, 1982.

Turnbull et al., "Heparan sulfate: decoding a dynamic multifunctional cell regulator," *Trends in Cell Biology*, Feb. 2001, 11(2):75-82.

Valentine et al., "Low-Molecular-Weight Heparin Therapy and Mortality," *Seminars in Thrombosis and Hemostasis*, vol. 23, No. 2, 1997, pp. 173-178.

Venkataraman et al., A stereochemical approach to pyranose ring flexibility: its implications for the conformation of dermatan sulfate. Proc Natl Acad Sci U S A. Jun. 21, 1994;91(13):6171-5.

Venkataraman et al., "Sequencing Complex Polysaccharides", *Science*, 286: 537-542, 1999.

Vlodavsky et al., Mammalian heparanase: gene cloning, expression and function in tumor progression and metastasis. Nat Med. Jul. 1999;5(7):793-802.

Von Bulow et al., Crystal structure of an enzyme-substrate complex provides insight into the interaction between human arylsulfatase A and its substrates during catalysis. J Mol Biol. Jan. 12, 2001;305(2):269-77.

Warnick et al., Purification of an unusual -glycuronidase from flavobacteria. Biochemistry. Feb. 15, 1972;11(4):568-72.

Wishart et al., "A Single Mutation Converts a Novel Phosphotyrosine Binding Domain into a Dual-specificity Phosphatase", *The Journal of Biological Chemistry*, 270(45): 26782-26785, 1995.

Witkowski et al., "Conversion of a β-Ketoacyl Synthase to a Malonyl Decarboxylase by Replacement of the Active-site Cysteine with Glutamine", *Biochemistry*, 38(36): 11643-11650, 1999.

Yamada et al., "Structural Studies on the Bacterial Lyase-resistant Tetrasaccharides Derived from the Antithrombin III-binding Site of Porcine Intestinal Heparin", *The Journal of Biological Chemistry*, 268(7): 4780-4787, 1993.

Yan et al., "Prime Numbers and the Amino Acid Code: Analogy in Coding Properties", *J. Theor. Biol.*, 151: 333-341, 1991.

Yang et al., Purification and characterization of heparinase from *Flavobacterium heparinum*. J Biol Chem. Feb. 10, 1985;260(3):1849-57.

Yoder et al., "Unusual structural features in the parallel β-helix in pectate lyases", *Structure*, Dec. 15, 1993, 1:241-251.

Yoder et al., "New Domain Motif: The Structure of Pectate Lyase C., a Secreted Plant Virulence Factor", *Science*, vol. 260, Jun. 4, 1993, pp. 1503-1506.

Zhang et al., "6-O-Sulfotransferase-1 Represents a Critical Enzyme in the Anticoagulant Heparan Sulfate Biosynthetic Pathway", *The Journal of Biological Chemistry*, 276(45): 42311-42321, 2001.

Zhao et al., "Rapid, Sensitive Structure Analysis of Oligosaccharides", *Proc. Natl. Acad. Sci. USA*, 94: 1629-1633, 1997.

Zucharski et al., "Blood Coagulation Activation in Cancer: Challenges for Cancer Treatement", *Hamostaseologie*, 1995, 15:14-20.

Genbank Accession No. U27585, BCT, Nov. 5, 1996 (2 pages).

Genbank Accession No. 171364, PAT, Dec. 23, 1997 (1 page).

SEQUENCE LISTING

<160> NUMBER OF SEQ ID NOS: 14

<210> SEQ ID NO 1
<211> LENGTH: 2339
<212> TYPE: DNA
<213> ORGANISM: Flavobacterium heparinum

<400> SEQUENCE: 1

-continued

```
atgaaaagac aattatacct gtatgtgatt tttgttgtag ttgaacttat ggttttaca        60
acaaagggct attcccaaac caaggccgat gtggtttgga agacgtgga tggcgtatct       120
atgcccatac cccctaagac ccacccgcgt ttgtatctac gtgagcagca agttcctgac       180
ctgaaaaaca ggatgaacga ccctaaactg aaaaaagttt gggccgatat gatcaagatg       240
caggaagact ggaagccagc tgatattcct gaagttaaag actttcgttt ttattttaac       300
cagaaagggc ttactgtaag ggttgaacta atggccctga actatctgat gaccaaggat       360
ccaaaggtag gacgggaagc catcacttca attattgata cccttgaaac tgcaactttt       420
aaaccagcag gtgatatttc gagagggata gtgatatttc gagagggata ggcctgttta       480
tggttacagg ggccattgtg tatgactggt gctacgatca gctgaaacca gaagagaaaa       540
cacgttttgt gaaggcattt gtgaggctgg ccaaaatgct cgaatgtggt tatcctccgg       600
taaaagacaa gtctattgtt gggcatgctt ccgaatggat gatcatgcgg gacctgcttt       660
ctgtagggat tgccatttac gatgaattcc ctgagatgta aacctggct gcgggtcgtt       720
ttttcaaaga acacctggtt gcccgcaact ggttttatcc ctcgcataac taccatcagg       780
gtatgtcata cctgaacgta agatttacca acgacctttt tgccctctgg atattagacc       840
ggatgggcgc tggtaatgtg tttaatccag ggcagcagtt tatcctttat gacgcgatct       900
ataaacgccg ccccgatgga cagattttag caggtggaga tgtagattat tccaggaaaa       960
aaccaaaata ttatacgatg cctgcattgc ttgcaggtag ctattataaa gatgaatacc      1020
ttaattacga attcctgaaa gatcccaatg ttgagccaca ttgcaaattg ttcgaatttt      1080
tatggcgcga tacccagttg ggaagtcgta agcctgatga tttgccactt tccaggtact      1140
caggatcgcc ttttggatgg atgattgccc gtaccggatg gggtccggaa agtgtgattg      1200
cagagatgaa agtcaacgaa tattccttc ttaaccatca gcatcaggat gcaggagcct      1260
tccagatcta ttacaaaggc ccgctggcca tagatgcagg ctcgtataca ggttcttcag      1320
gaggttataa cagtccgcac aacaagaact ttttaagcg gactattgca cacaatagct      1380
tgctgattta cgatcctaaa gaaactttca gttcgtcggg atatggtgga agtgaccata      1440
ccgattttgc tgccaacgat ggtggtcagc ggctgcccgg aaaaggttgg attgcaccc      1500
gcgaccttaa agaaatgctg gcaggcgatt tcaggaccgg caaaattctt gcccagggct      1560
ttggtccgga taaccaaacc cctgattata cttatctgaa aggagacatt acagcagctt      1620
attcggcaaa agtgaaggaa gtaaaacgtt catttctatt cctgaacctt aaggatgcca      1680
aagttccggc agcgatgatc gttttttgaca aggtagttgc ttccaatcct gatttttaaga      1740
agttctggtt gttgcacagt attgagcagc ctgaaataaa ggggaatcag attaccataa      1800
aacgtacaaa aaacggtgat agtgggatgt tggtgaatac ggctttgctg ccggatgcgg      1860
ccaattcaaa cattacctcc attggcggca agggcaaaga cttctgggtg tttggtacca      1920
attataccaa tgatcctaaa ccgggcacgg atgaagcatt ggaacgtgga gaatggcgtg      1980
tggaaatcac tccaaaaaag gcagcagccg aagattacta cctgaatgtg atacagattg      2040
ccgacaatac acagcaaaaa ttacacgagg tgaagcgtat tgacggtgac aaggttgttg      2100
gtgtgcagct tgctgacagg atagttactt ttagcaaaac ttcagaaact gttgatcgtc      2160
cctttggctt ttccgttgtt ggtaaaggaa cattcaaatt tgtgatgacc gatctttag      2220
cgggtacctg gcaggtgctg aaagacggaa aaatactta tcctgcgctt tctgcaaaag      2280
gtgatgatgg accccttat tttgaaggaa ctgaaggaac ctaccgtttt ttgagataa       2339
```

<210> SEQ ID NO 2
<211> LENGTH: 772
<212> TYPE: PRT
<213> ORGANISM: Flavobacterium heparinum

<400> SEQUENCE: 2

```
Met Lys Arg Gln Leu Tyr Leu Tyr Val Ile Phe Val Val Glu Leu
 1               5                  10                  15

Met Val Phe Thr Thr Lys Gly Tyr Ser Gln Thr Lys Ala Asp Val Val
                20                  25                  30

Trp Lys Asp Val Asp Gly Val Ser Met Pro Ile Pro Pro Lys Thr His
            35                  40                  45

Pro Arg Leu Tyr Leu Arg Glu Gln Gln Val Pro Asp Leu Lys Asn Arg
        50                  55                  60

Met Asn Asp Pro Lys Leu Lys Lys Val Trp Ala Asp Met Ile Lys Met
65                  70                  75                  80

Gln Glu Asp Trp Lys Pro Ala Asp Ile Pro Glu Val Lys Asp Phe Arg
                85                  90                  95

Phe Tyr Phe Asn Gln Lys Gly Leu Thr Val Arg Val Glu Leu Met Ala
            100                 105                 110

Leu Asn Tyr Leu Met Thr Lys Asp Pro Lys Val Gly Arg Glu Ala Ile
        115                 120                 125

Thr Ser Ile Ile Asp Thr Leu Glu Thr Ala Thr Phe Lys Pro Ala Gly
    130                 135                 140

Asp Ile Ser Arg Gly Ile Gly Leu Phe Met Val Thr Gly Ala Ile Val
145                 150                 155                 160

Tyr Asp Trp Cys Tyr Asp Gln Leu Lys Pro Glu Glu Lys Thr Arg Phe
                165                 170                 175

Val Lys Ala Phe Val Arg Leu Ala Lys Met Leu Glu Cys Gly Tyr Pro
            180                 185                 190

Pro Val Lys Asp Lys Ser Ile Val Gly His Ala Ser Glu Trp Met Ile
        195                 200                 205

Met Arg Asp Leu Leu Ser Val Gly Ile Ala Ile Tyr Asp Glu Phe Pro
    210                 215                 220

Glu Met Tyr Asn Leu Ala Ala Gly Arg Phe Phe Lys Glu His Leu Val
225                 230                 235                 240

Ala Arg Asn Trp Phe Tyr Pro Ser His Asn Tyr His Gln Gly Met Ser
                245                 250                 255

Tyr Leu Asn Val Arg Phe Thr Asn Asp Leu Phe Ala Leu Trp Ile Leu
            260                 265                 270

Asp Arg Met Gly Ala Gly Asn Val Phe Asn Pro Gly Gln Gln Phe Ile
        275                 280                 285

Leu Tyr Asp Ala Ile Tyr Lys Arg Arg Pro Asp Gly Gln Ile Leu Ala
    290                 295                 300

Gly Gly Asp Val Asp Tyr Ser Arg Lys Lys Pro Lys Tyr Tyr Thr Met
305                 310                 315                 320

Pro Ala Leu Leu Ala Gly Ser Tyr Tyr Lys Asp Glu Tyr Leu Asn Tyr
                325                 330                 335

Glu Phe Leu Lys Asp Pro Asn Val Glu Pro His Cys Lys Leu Phe Glu
            340                 345                 350

Phe Leu Trp Arg Asp Thr Gln Leu Gly Ser Arg Lys Pro Asp Asp Leu
        355                 360                 365

Pro Leu Ser Arg Tyr Ser Gly Ser Pro Phe Gly Trp Met Ile Ala Arg
    370                 375                 380
```

```
Thr Gly Trp Gly Pro Glu Ser Val Ile Ala Glu Met Lys Val Asn Glu
385                 390                 395                 400

Tyr Ser Phe Leu Asn His Gln His Gln Asp Ala Gly Ala Phe Gln Ile
            405                 410                 415

Tyr Tyr Lys Gly Pro Leu Ala Ile Asp Ala Gly Ser Tyr Thr Gly Ser
            420                 425                 430

Ser Gly Gly Tyr Asn Ser Pro His Asn Lys Asn Phe Phe Lys Arg Thr
435                 440                 445

Ile Ala His Asn Ser Leu Leu Ile Tyr Asp Pro Lys Glu Thr Phe Ser
450                 455                 460

Ser Ser Gly Tyr Gly Gly Ser Asp His Thr Asp Phe Ala Ala Asn Asp
465                 470                 475                 480

Gly Gly Gln Arg Leu Pro Gly Lys Gly Trp Ile Ala Pro Arg Asp Leu
                485                 490                 495

Lys Glu Met Leu Ala Gly Asp Phe Arg Thr Gly Lys Ile Leu Ala Gln
                500                 505                 510

Gly Phe Gly Pro Asp Asn Gln Thr Pro Asp Tyr Thr Tyr Leu Lys Gly
                515                 520                 525

Asp Ile Thr Ala Ala Tyr Ser Ala Lys Val Lys Glu Val Lys Arg Ser
                530                 535                 540

Phe Leu Phe Leu Asn Leu Lys Asp Ala Lys Val Pro Ala Ala Met Ile
545                 550                 555                 560

Val Phe Asp Lys Val Ala Ser Asn Pro Asp Phe Lys Lys Phe Trp
                565                 570                 575

Leu Leu His Ser Ile Glu Gln Pro Glu Ile Lys Gly Asn Gln Ile Thr
                580                 585                 590

Ile Lys Arg Thr Lys Asn Gly Asp Ser Gly Met Leu Val Asn Thr Ala
                595                 600                 605

Leu Leu Pro Asp Ala Ala Asn Ser Asn Ile Thr Ser Ile Gly Gly Lys
                610                 615                 620

Gly Lys Asp Phe Trp Val Phe Gly Thr Asn Tyr Thr Asn Asp Pro Lys
625                 630                 635                 640

Pro Gly Thr Asp Glu Ala Leu Glu Arg Gly Glu Trp Arg Val Glu Ile
                645                 650                 655

Thr Pro Lys Lys Ala Ala Ala Glu Asp Tyr Tyr Leu Asn Val Ile Gln
                660                 665                 670

Ile Ala Asp Asn Thr Gln Gln Lys Leu His Glu Val Lys Arg Ile Asp
                675                 680                 685

Gly Asp Lys Val Val Gly Val Gln Leu Ala Asp Arg Ile Val Thr Phe
                690                 695                 700

Ser Lys Thr Ser Glu Thr Val Asp Arg Pro Phe Gly Phe Ser Val Val
705                 710                 715                 720

Gly Lys Gly Thr Phe Lys Phe Val Met Thr Asp Leu Leu Pro Gly Thr
                725                 730                 735

Trp Gln Val Leu Lys Asp Gly Lys Ile Leu Tyr Pro Ala Leu Ser Ala
                740                 745                 750

Lys Gly Asp Asp Gly Pro Leu Tyr Phe Glu Gly Thr Glu Gly Thr Tyr
                755                 760                 765

Arg Phe Leu Arg
        770

<210> SEQ ID NO 3
<211> LENGTH: 1379
```

```
<212> TYPE: DNA
<213> ORGANISM: Flavobacterium heparinum
<220> FEATURE:
<221> NAME/KEY: CDS
<222> LOCATION: (173)...(1327)
<220> FEATURE:
<221> NAME/KEY: mat_peptide
<222> LOCATION: (236)...(1324)

<400> SEQUENCE: 3
```

| | |
|---|---|
| cctttttggga gcaaaggcag aaccatctcc gaacaaaggc agaaccagcc tgtaaacaga | 60 |
| cagcaattca tccgctttca accaaagtga aagcatttaa tacaatacca gaatgtcgca | 120 |
| tttcccttc agcgtacttt ttgggtaaat aaccaataaa aactaaagac gg atg aaa | 178 |
|                                                                                                                                                                                                                                                                      Met Lys | |
|                                                                                                                                                                                                                                                                         1 | |
| aaa caa att cta tat ctg att gta ctt cag caa ctg ttc ctc tgt tcg<br>Lys Gln Ile Leu Tyr Leu Ile Val Leu Gln Gln Leu Phe Leu Cys Ser<br>        5                   10                 15 | 226 |
| gct tac gcc cag caa aaa aaa tcc ggt aac atc cct tac cgg gta aat<br>Ala Tyr Ala Gln Gln Lys Lys Ser Gly Asn Ile Pro Tyr Arg Val Asn<br> 20                    25                    30 | 274 |
| gtg cag gcc gac agt gct aag cag aag gcg att att gac aac aaa tgg<br>Val Gln Ala Asp Ser Ala Lys Gln Lys Ala Ile Ile Asp Asn Lys Trp<br>35                   40                    45                    50 | 322 |
| gtg gca gta ggc atc aat aaa cct tat gca tta caa tat gac gat aaa<br>Val Ala Val Gly Ile Asn Lys Pro Tyr Ala Leu Gln Tyr Asp Asp Lys<br>                  55                    60                    65 | 370 |
| ctg cgc ttt aat gga aaa cca tcc tat cgc ttt gag ctt aaa gcc gaa<br>Leu Arg Phe Asn Gly Lys Pro Ser Tyr Arg Phe Glu Leu Lys Ala Glu<br>                70                    75                    80 | 418 |
| gac aat tcg ctt gaa ggt tat gct gca gga gaa aca aag ggc cgt aca<br>Asp Asn Ser Leu Glu Gly Tyr Ala Ala Gly Glu Thr Lys Gly Arg Thr<br>              85                    90                    95 | 466 |
| gaa ttg tcg tac agc tat gca acc acc aat gat ttt aag aaa ttt ccc<br>Glu Leu Ser Tyr Ser Tyr Ala Thr Thr Asn Asp Phe Lys Lys Phe Pro<br>100                   105                    110 | 514 |
| cca agc gta tac caa aat gcg caa aag cta aaa acc gtt tat cat tac<br>Pro Ser Val Tyr Gln Asn Ala Gln Lys Leu Lys Thr Val Tyr His Tyr<br>115                   120                   125                 130 | 562 |
| ggc aaa ggg att tgt gaa cag ggg agc tcc cgc agc tat acc ttt tca<br>Gly Lys Gly Ile Cys Glu Gln Gly Ser Ser Arg Ser Tyr Thr Phe Ser<br>                 135                   140                   145 | 610 |
| gtg tac ata ccc tcc tcc ttc ccc gac aat gcg act act att ttt gcc<br>Val Tyr Ile Pro Ser Ser Phe Pro Asp Asn Ala Thr Thr Ile Phe Ala<br>               150                   155                   160 | 658 |
| caa tgg cat ggt gca ccc agc aga acg ctt gta gct aca cca gag gga<br>Gln Trp His Gly Ala Pro Ser Arg Thr Leu Val Ala Thr Pro Glu Gly<br>             165                   170                   175 | 706 |
| gaa att aaa aca ctg agc ata gaa gag ttt ttg gcc tta tac gac cgc<br>Glu Ile Lys Thr Leu Ser Ile Glu Glu Phe Leu Ala Leu Tyr Asp Arg<br>180                   185                    190 | 754 |
| atg atc ttc aaa aaa aat atc gcc cat gat aaa gtt gaa aaa aaa gat<br>Met Ile Phe Lys Lys Asn Ile Ala His Asp Lys Val Glu Lys Lys Asp<br>195                   200                   205                 210 | 802 |
| aag gac gga aaa att act tat gta gcc gga aag cca aat ggc tgg aag<br>Lys Asp Gly Lys Ile Thr Tyr Val Ala Gly Lys Pro Asn Gly Trp Lys<br>               215                   220                   225 | 850 |
| gta gaa caa ggt ggt tat ccc acg ctg gcc ttt ggt ttt tct aaa ggg<br>Val Glu Gln Gly Gly Tyr Pro Thr Leu Ala Phe Gly Phe Ser Lys Gly<br>             230                   235                   240 | 898 |

```
tat ttt tac atc aag gca aac tcc gac cgg cag tgg ctt acc gac aaa        946
Tyr Phe Tyr Ile Lys Ala Asn Ser Asp Arg Gln Trp Leu Thr Asp Lys
            245                 250                 255 gcc gac cgt aac aat gcc aat ccc gag aat agt gaa gta atg aag ccc        994
Ala Asp Arg Asn Asn Ala Asn Pro Glu Asn Ser Glu Val Met Lys Pro
260                 265                 270 tat tcc tcg gaa tac aaa act tca acc att gcc tat aaa atg ccc ttt       1042
Tyr Ser Ser Glu Tyr Lys Thr Ser Thr Ile Ala Tyr Lys Met Pro Phe
275                 280                 285                 290 gcc cag ttc cct aaa gat tgc tgg att act ttt gat gtc gcc ata gac       1090
Ala Gln Phe Pro Lys Asp Cys Trp Ile Thr Phe Asp Val Ala Ile Asp
                295                 300                 305 tgg acg aaa tat gga aaa gag gcc aat aca att ttg aaa ccc ggt aag       1138
Trp Thr Lys Tyr Gly Lys Glu Ala Asn Thr Ile Leu Lys Pro Gly Lys
            310                 315                 320 ctg gat gtg atg atg act tat acc aag aat aag aaa cca caa aaa gcg       1186
Leu Asp Val Met Met Thr Tyr Thr Lys Asn Lys Lys Pro Gln Lys Ala
        325                 330                 335 cat atc gta aac cag cag gaa atc ctg atc gga cgt aac gat gac gat       1234
His Ile Val Asn Gln Gln Glu Ile Leu Ile Gly Arg Asn Asp Asp Asp
    340                 345                 350 ggc tat tac ttc aaa ttt gga att tac agg gtc ggt aac agc acg gtc       1282
Gly Tyr Tyr Phe Lys Phe Gly Ile Tyr Arg Val Gly Asn Ser Thr Val
355                 360                 365                 370 ccg gtt act tat aac ctg agc ggg tac agc gaa act gcc aga tag            1327
Pro Val Thr Tyr Asn Leu Ser Gly Tyr Ser Glu Thr Ala Arg
                375                 380 caaaagccct aagcgcatcc gatagggctt ttcttatatt tacaataaaa tt              1379

<210> SEQ ID NO 4
<211> LENGTH: 384
<212> TYPE: PRT
<213> ORGANISM: Flavobacterium heparinum

<400> SEQUENCE: 4

Met Lys Lys Gln Ile Leu Tyr Leu Ile Val Leu Gln Gln Leu Phe Leu
  1               5                  10                  15

Cys Ser Ala Tyr Ala Gln Gln Lys Lys Ser Gly Asn Ile Pro Tyr Arg
                 20                  25                  30

Val Asn Val Gln Ala Asp Ser Ala Lys Gln Lys Ala Ile Ile Asp Asn
             35                  40                  45

Lys Trp Val Ala Val Gly Ile Asn Lys Pro Tyr Ala Leu Gln Tyr Asp
 50                  55                  60

Asp Lys Leu Arg Phe Asn Gly Lys Pro Ser Tyr Arg Phe Glu Leu Lys
 65                  70                  75                  80

Ala Glu Asp Asn Ser Leu Glu Gly Tyr Ala Ala Gly Glu Thr Lys Gly
                 85                  90                  95

Arg Thr Glu Leu Ser Tyr Ser Tyr Ala Thr Thr Asn Asp Phe Lys Lys
            100                 105                 110

Phe Pro Pro Ser Val Tyr Gln Asn Ala Gln Lys Leu Lys Thr Val Tyr
        115                 120                 125

His Tyr Gly Lys Gly Ile Cys Glu Gln Gly Ser Ser Arg Ser Tyr Thr
    130                 135                 140

Phe Ser Val Tyr Ile Pro Ser Ser Phe Pro Asp Asn Ala Thr Thr Ile
145                 150                 155                 160

Phe Ala Gln Trp His Gly Ala Pro Ser Arg Thr Leu Val Ala Thr Pro
                165                 170                 175
```

-continued

```
Glu Gly Glu Ile Lys Thr Leu Ser Ile Glu Glu Phe Leu Ala Leu Tyr
            180                 185                 190

Asp Arg Met Ile Phe Lys Lys Asn Ile Ala His Asp Lys Val Glu Lys
            195                 200                 205

Lys Asp Lys Asp Gly Lys Ile Thr Tyr Val Ala Gly Lys Pro Asn Gly
    210                 215                 220

Trp Lys Val Glu Gln Gly Gly Tyr Pro Thr Leu Ala Phe Gly Phe Ser
225                 230                 235                 240

Lys Gly Tyr Phe Tyr Ile Lys Ala Asn Ser Asp Arg Gln Trp Leu Thr
                245                 250                 255

Asp Lys Ala Asp Arg Asn Asn Ala Asn Pro Glu Asn Ser Glu Val Met
            260                 265                 270

Lys Pro Tyr Ser Ser Glu Tyr Lys Thr Ser Thr Ile Ala Tyr Lys Met
            275                 280                 285

Pro Phe Ala Gln Phe Pro Lys Asp Cys Trp Ile Thr Phe Asp Val Ala
    290                 295                 300

Ile Asp Trp Thr Lys Tyr Gly Lys Glu Ala Asn Thr Ile Leu Lys Pro
305                 310                 315                 320

Gly Lys Leu Asp Val Met Met Thr Tyr Thr Lys Asn Lys Lys Pro Gln
                325                 330                 335

Lys Ala His Ile Val Asn Gln Gln Glu Ile Leu Ile Gly Arg Asn Asp
            340                 345                 350

Asp Asp Gly Tyr Tyr Phe Lys Phe Gly Ile Tyr Arg Val Gly Asn Ser
            355                 360                 365

Thr Val Pro Val Thr Tyr Asn Leu Ser Gly Tyr Ser Glu Thr Ala Arg
    370                 375                 380

<210> SEQ ID NO 5
<211> LENGTH: 10
<212> TYPE: PRT
<213> ORGANISM: Flavobacterium heparinum

<400> SEQUENCE: 5

Lys Asp Pro Asn Val Glu Pro His Cys Lys
1               5                   10

<210> SEQ ID NO 6
<211> LENGTH: 34
<212> TYPE: PRT
<213> ORGANISM: Flavobacterium heparinum

<400> SEQUENCE: 6

Lys Tyr Tyr Thr Met Pro Ala Leu Leu Ala Gly Ser Tyr Tyr Lys Asp
1               5                   10                  15

Glu Tyr Leu Asn Tyr Glu Phe Leu Lys Asp Pro Asn Val Glu Pro His
            20                  25                  30

Cys Lys

<210> SEQ ID NO 7
<211> LENGTH: 14
<212> TYPE: PRT
<213> ORGANISM: Flavobacterium heparinum

<400> SEQUENCE: 7

Arg Thr Ile Ala His Asn Ser Leu Leu Ile Tyr Asp Pro Lys
1               5                   10

<210> SEQ ID NO 8
```

```
<211> LENGTH: 15
<212> TYPE: PRT
<213> ORGANISM: Flavobacterium heparinum

<400> SEQUENCE: 8

Lys Arg Thr Ile Ala His Asn Ser Leu Leu Ile Tyr Asp Pro Lys
1               5                   10                  15

<210> SEQ ID NO 9
<211> LENGTH: 7
<212> TYPE: PRT
<213> ORGANISM: Flavobacterium heparinum

<400> SEQUENCE: 9

Lys Glu His Leu Val Ala Arg
1               5

<210> SEQ ID NO 10
<211> LENGTH: 14
<212> TYPE: PRT
<213> ORGANISM: Flavobacterium heparinum

<400> SEQUENCE: 10

Lys Phe Trp Leu Leu His Ser Ile Glu Gln Pro Glu Ile Lys
1               5                   10

<210> SEQ ID NO 11
<211> LENGTH: 7
<212> TYPE: PRT
<213> ORGANISM: Flavobacterium heparinum

<400> SEQUENCE: 11

Lys Ala Ile Ile Asp Asn Lys
1               5

<210> SEQ ID NO 12
<211> LENGTH: 13
<212> TYPE: PRT
<213> ORGANISM: Flavobacterium heparinum

<400> SEQUENCE: 12

Lys Asn Ile Ala His Asp Lys Val Glu Lys Lys Asp Lys
1               5                   10

<210> SEQ ID NO 13
<211> LENGTH: 10
<212> TYPE: PRT
<213> ORGANISM: Flavobacterium heparinum

<400> SEQUENCE: 13

Arg Val Asn Val Gln Ala Asp Ser Ala Lys
1               5                   10

<210> SEQ ID NO 14
<211> LENGTH: 26
<212> TYPE: PRT
<213> ORGANISM: Flavobacterium heparinum

<400> SEQUENCE: 14

Lys Phe Gly Ile Tyr Arg Val Gly Asn Ser Thr Val Pro Val Thr Tyr
1               5                   10                  15

Asn Leu Ser Gly Tyr Ser Glu Thr Ala Arg
            20                  25
```

RATIONALLY DESIGNED HEPARINASES DERIVED FROM HEPARINASE I AND II AND METHODS OF SEQUENCING THEREWITH

RELATED APPLICATIONS

This application is a divisional of U.S. patent application Ser. No. 09/384,959, filed on Aug. 27, 1999, allowed, which claims priority under 35 U.S.C. §119 from U.S. provisional application Ser. No. 60/098,153, filed Aug. 27, 1998, the entire contents of each of which are herein incorporated by reference.

GOVERNMENT SUPPORT

This invention was made with government support under Grant No. NIH-1R01-GM57073 awarded by the National Institutes of Health. The government may have certain rights to the invention.

FIELD OF THE INVENTION

The present invention relates to heparinases and the rational design of the same. In particular, the present invention relates to new heparinases rationally designed and based upon heparinase I and II of *Flavobacterium heparinum*.

BACKGROUND OF THE INVENTION

Heparin-like glycosaminoglycans (HLGAGs) are key components of the extracellular matrix (ECM) that serve to regulate an array of biological functions (Jackson, R. L., Busch, S. J., Cardin, A. D. (1991) *Physiological Reviews* 71, 481-539; Lindahl, U., Lidholt, K., Spillmann, D., Kjellén, L. (1994) *Thrombosis Research* 75, 1-32). HLGAGs, which include the polysaccharides heparin and heparan sulfate, are characterized by a disaccharide repeating unit of uronic acid and hexosamine, where the uronic acid is either L-iduronic acid or D-glucuronic acid and the hexosamine is linked to the uronic acid by a 1→4 linkage (Jackson, R. L., Busch, S. J., & Cardin, A. D. (1991) Physiol. Rev. 71:481-539). Heparin possesses predominantly L-iduronic acid with a high degree of sulfation (Conrad, H. E. (1989) *Ann. N.Y. Acad. Sci.* 556, 18-28; Ernst, S., Langer, R., Cooney, C. L., Sasisekharan, R. (1995) *CRC Critical Rev. Biochem. Mol. Biol.* 30, 387-444). Heparan sulfate is chemically similar to heparin but contains less 2-O-sulfate and N-sulfate groups than heparin and also possesses a higher percentage of D-glucuronic acid within the polymer (Conrad, H. E. (1989) *Ann. N.Y. Acad. Sci.* 556, 18-28; Linhardt, R. J., Rice, K. G., Kim, Y. S., Lohse, D. L., Wang, H. M., Loganathan, D. (1988) *Biochem. J.* 254, 781-87). HLGAGs are complex due to the high degree and varying patterns of sulfation and acetylation on both the uronic acid and the hexosamine residues. It is believed that it is the sulfation which is responsible for the numerous different functional roles of these carbohydrates.

Our understanding of heparin's and heparan-sulfate's functional roles is severely limited, however, by our limited knowledge of the heparin and heparan sulfate sequence. In fact one of the major challenges in elucidating a specific role for HLGAGs in certain biological systems is that the considerable chemical heterogeneity of HLGAGs has thwarted attempts to determine sequence-function relationships (Ernst, S., Langer, R., Cooney, C. L., Sasisekharan, R. (1995) *CRC Critical Rev. Biochem. Mol. Biol.* 30, 387-444; Hascall, V. C., Midura, R. J. (1989) in *Keratan Sulphate—Chemistry, Biology, Clinical Pathology* (Greiling, H. and Scott, J. E., eds.), pp. 66-73, The Biochemical Society, London).

HLGAG degrading enzymes, or heparinases, are a family of polysaccharide lyases that catalyze the cleavage of HLGAGs through an elimination reaction by a nucleophilic amino acid. Heparinases have proved to be useful tools in heparin degradation and in providing composition and sequence information (Linhardt, R. J., Turnbull, J. E., Wang, H. M., Longanathan, D., & Gallagher, J. T. (1990) Biochemistry 29:2611-2617). *F. heparinum* produces at least three types of heparinases (I, II and III) with different substrate specificities (Lohse, D. L., & Linhardt, R. J. (1992) J. Biol. Chem. 267:24347-24355). All three enzymes have been cloned and recombinantly expressed (Sasisekharan, R., Bulmer, M., Moremen, K. W., Cooney, C. L., Langer, R. (1993) *Proc. Natl. Acad. Sci. USA* 90, 3660-64; Godavarti, R., Davis, M, Venkatararnan, G, Cooney, C, Langer, R, and Sasisekharan, R (1996a) *Biochem. Biophys. Res. Comm.* 225, 751-758; Godavarti, R., Cooney, C. L., Langer, R., Sasisekharan, R. (1996b) *Biochemistry* 35, 6846-6852; Ernst, S., Venkataraman, G., Winkler, S., Godavarti, R., Langer, R., Cooney, C. L., Sasisekharan, R. (1996) *Biochem. J.* 315, 589-597).

The three heparinases, from *F. heparinum*, are distinguished on the basis of their size, charge properties, and substrate specificities (Ernst, S., Langer, R., Cooney, C. L., Sasisekharan, R. (1995) *CRC Critical Rev. Biochem. Mol. Biol.* 30, 387-444). Heparinase I, a 42 kDa protein with a pI of 8.5-9.3, primarily cleaves HLGAGs at sites with an O-sulfated L-iduronic acid linkage (i.e., heparin-like regions). Heparinase III, a 73 kDa protein with a pI of about 9, requires primarily an unsulfated D-glucuronic acid moiety (heparan sulfate-like regions). While there is evidence for a secondary substrate specificity for heparinases I and III (Yamada, S., Murakami, T., Tsuda, H., Yoshida, K., Sugahara, K. (1995) *J. Biol. Chem.* 270, 8696-705; Desai, U., Wang, H., Linhardt, R. (1993) *Arch. Biochem. Biophys.* 306, 461-8), these enzymes do show a predominant enzymatic preference for a C5 epimer of uronic acid, with heparinase III primarily acting at hexosamine-glucuronic acid linkages and heparinase I acting primarily at hexosamine-iduronic acid linkages. Heparinase II is the largest of the heparinases and has the broadest substrate specificity. The 84 kDa protein has a pI of around 9 and cleaves both heparin and heparan sulfate-like regions of HLGAGs (Ernst, S., Langer, R., Cooney, C. L., Sasisekharan, R. (1995) *CRC Critical Rev. Biochem. Mol. Biol.* 30, 387-444; Lohse, D. L., Linhardt, R. J. (1992) *J. Biol. Chem.* 267, 24347-55). Thus, unlike heparinase I and heparinase III, which distinguish between the C5 epimers L-iduronic acid and D-glucuronic acid, heparinase II is catalytically active towards both (Ernst, S., Langer, R., Cooney, C. L., Sasisekharan, R. (1995) *CRC Critical Rev. Biochem. Mol. Biol.* 30, 387-444).

Through extensive biochemical and site-directed mutagenesis experiments, our studies with heparinase I have led to the identification of three residues: cysteine 135, histidine 203, and lysine 199, that are critical for enzymatic function (Godavarti, R., Cooney, C. L., Langer, R., Sasisekharan, R. (1996b) *Biochemistry* 35, 6846-6852; Ernst, S., Venkataraman, G., Winkler, S., Godavarti, R., Langer, R., Cooney, C. L., Sasisekharan, R. (1996) *Biochem. J.* 315, 589-597; Sasisekharan, R., Leckband, D., Godavarti, R., Venkataraman, G., Cooney, C. L., Langer, R. (1995) *Biochemistry* 34, 14441-14448, and PCT Patent Application WO 97/16556, claiming priority to U.S. Provisional Patent Application Ser. No., 60/008,069, and it's related US National Phase patent application, (U.S. Ser. No. 09/066,481), which is hereby incorporated by reference). A mechanism was proposed wherein cysteine 135 was the active site base that abstracted the C5 hydrogen from iduronic acid, which, when coupled to the cleavage of the glycosidic bond, led to the formation of the 4,5-unsaturated uronate product (Sasisekharan, R., Leckband, D., Godavarti, R., Venkataraman, G., Cooney, C. L., Langer, R. (1995) *Biochemistry* 34, 14441-14448). Thus, a stereospecific role for cysteine 135 was posited that allowed heparinase I to distinguish between heparin and heparan sulfate-like regions.

It is desirable to develop molecular tools that can serve to elucidate structure-function relationships between HLGAGs and biological molecules, such as growth factors and cytokines. One such tool has proved to be the three heparinases derived from *F. heparinum* (Linhardt, R. J., et al., *Heparin and Related Polysaccharides*, (Lane, D. A., et al eds.) P. 37-47, Plenum Press, New York). Using heparinases, HLGAGs have been shown to be critical players in major biological functions including angiogenesis (14) and development (Binari, R. C., et al., *Development*, (Camb) 124, p. 2623-2632 (1997); Cumberledge and Reichsman, *Trends Genet*, 13, p. 421-423 (1997)). Heparinase I has been utilized in the sequence determination of sugars, in the preparation of small heparin fragments for therapeutic uses, and in the ex vivo removal of heparin from blood (Linhardt, R. J., Turnbull, J. E., Wang, H. M., Longanathan, D., & Gallagher, J. T. (1990) *Biochemistry* 29:2611-2617; Bernstein, H., Yang, V. C., Cooney, C. L., & Langer, R. (1988) Methods in Enzymol. 137:515-529). Extracorporeal medical devices (e.g. hemodialyzer, pump-oxygenator) rely on systemic heparinization to provide blood compatibility within the device and a blood filter containing immobilized heparinase I at the effluent which is capable of neutralizing the heparin before the blood is returned to the body (Bernstein, H., Yang, V. C., Cooney, C. L., & Langer, R. (1988) Methods in Enzymol. 137:515-529).

There has been much speculation in the art about the possibility of creating "designer" enzymes, rationally designed to have desired substrate specificities and activities. Yet, although the importance of different levels (primary, secondary, and tertiary) of protein structure in determining the functional activity of enzymes has long been recognized, the lack of a broad and detailed understanding of the relationship between structure and function has prevented significant progress. Even for enzymes which have known activities, substrates, and primary structures, the general lack of information about secondary and tertiary structures and the relationship of these to function has made it difficult to predict the functional effect of any particular changes to the primary structure.

SUMMARY OF THE INVENTION

The present invention provides new polysaccharide lyases derived from heparinase and rationally designed based upon detailed structural and functional characterization of heparinase I and II. The novel heparinases of the invention demonstrate different properties than the native enzymes. Some of the novel heparinases, for example, demonstrate enhanced stability, freedom from calcium dependence, or unique binding catalytic functions that result in the production of a unique product profile. These novel heparinases are useful for studying structure-function relationship of HLGAGs as well as for therapeutic purposes.

The invention in one aspect is a substantially pure heparinase including a modified heparinase II that can cleave a glycosaminoglycan substrate having a modified heparinase II $k_{cat}$ value, wherein the modified heparinase II $k_{cat}$ value is at least 10% different than a native heparinase II $k_{cat}$ value. In one embodiment the modified heparinase II $k_{cat}$ value is at least 20% different than a native heparinase II $k_{cat}$ value. In one embodiment the modified heparinase II $k_{cat}$ value is at least 50% different than a native heparinase II $k_{cat}$ value. In another embodiment the modified heparinase II has a reduced enzymatic activity with respect to heparin. Preferably the modified heparinase II has substantially the same enzymatic activity as native heparinase with respect to heparan sulfate. In yet another embodiment the modified heparinase II has a reduced enzymatic activity with respect to heparan sulfate. Preferably the modified heparinase II has substantially the same enzymatic activity as native heparinase with respect to heparin.

The modified heparinase can differ from native heparinase by including one or more amino acid substitutions, deletions or additions. The modified heparinase II can have the amino acid sequence of the mature peptide of SEQ ID NO: 2 wherein at least one amino acid residue has been substituted and wherein the substitution is selected from the group consisting of (a) a substitution of a cysteine residue corresponding to position 348 of SEQ ID NO: 2 with a residue selected from the group consisting of alanine, serine, tyrosine, histidine, threonine, and lysine; (b) a substitution of a histidine residue corresponding to at least one of positions 238, 440, 451, and 579 of SEQ ID NO: 2 with a residue selected from the group consisting of alanine, serine, tyrosine, threonine, and lysine; and (c) a conservative substitution of a heparin-binding sequence corresponding to positions 446-451 of SEQ ID NO: 2.

In one embodiment the modified heparinase II has the amino acid sequence of the mature peptide of SEQ ID NO: 2 wherein the cysteine residue corresponding to position 348 of SEQ ID NO: 2 has been substituted with a residue selected from the group consisting of alanine, serine, tyrosine, histidine, threonine, and lysine. Preferably the cysteine residue has been substituted with an alanine.

In another embodiment the modified heparinase II has the amino acid sequence of the mature peptide of SEQ ID NO: 2 wherein the histidine residue corresponding to position 440 of SEQ ID NO: 2 has been substituted with a residue selected from the group consisting of alanine, serine, tyrosine, threonine, and lysine. Preferably the histidine residue has been substituted with an alanine.

According to another embodiment an immobilized substantially pure modified heparinase II is also provided. The immobilized substantially pure modified heparinase II includes any of the substantially pure heparinase II molecules encompassed by the invention, and a solid support membrane, wherein the modified heparinase II is immobilized on the solid support membrane.

According to another aspect of the invention a substantially pure heparinase is provided. The heparinase includes a modified heparinase I wherein the modified heparinase I has enzymatic activity that is not dependent on the presence of calcium. In one embodiment the modified heparinase I has a modified heparinase I $k_{cat}$ value that is at least 10% different than a native heparinase I $k_{cat}$ value. In one embodiment the modified heparinase I has a modified heparinase I $k_{cat}$ value that is at least 20% different than a native heparinase I $k_{cat}$ value. In one embodiment the modified heparinase I has a modified heparinase I $k_{cat}$ value that is at least 50% different than a native heparinase I $k_{cat}$ value.

The heparinase can have one or more amino acid substitutions, deletions or additives. The modified heparinase I, in one embodiment, has the amino acid sequence of the mature peptide of SEQ ID NO: 4 wherein at least one amino acid residue has been substituted and wherein the substitution is a substitution of a serine residue corresponding to position 377 of SEQ ID NO: 4 with a residue selected from the group consisting of alanine, serine, tyrosine, histidine, threonine, and lysine. Preferably the serine residue has been substituted with an alanine.

In another aspect, the invention is a modified heparinase II having at least one amino acid substitution in the substrate binding region or active site, wherein the active site retains a positive charge.

According to another embodiment an immobilized substantially pure modified heparinase I is also provided. The immobilized substantially pure modified heparinase I includes any of the substantially pure heparinase I molecules encompassed by the invention, and a solid support membrane, wherein the modified heparinase I is immobilized on the solid support membrane.

The invention in another aspect is a substantially pure heparinase of a modified heparinase II having a modified product profile, wherein the modified product profile of the modified heparinase II is at least 10% different than a native product profile of a native heparinase II. In one embodiment the modified heparinase II has a modified product profile that is at least 20% different than a native product profile of a native heparinase II. In another embodiment the modified heparinase II has a modified product profile that is at least 50% different than a native product profile of a native heparinase II.

In one embodiment the modified product profile is modified with respect to heparin. In another embodiment the modified product profile is modified with respect to heparan sulfate.

According to another embodiment an immobilized substantially pure modified heparinase II is also provided. The immobilized substantially pure modified heparinase II includes the modified heparinase II described above, and a solid support membrane, wherein the modified heparinase II is immobilized on the solid support membrane.

A pharmaceutical preparation comprising a sterile formulation of any of the substantially pure heparinases encompassed by the invention and a pharmaceutically acceptable carrier are also included in the invention.

In another aspect the invention is a method of specifically cleaving a heparin-like glycosaminoglycan. The method includes the step of contacting a heparin-like glycosaminoglycan with any of the modified heparinase encompassed by the invention.

In one embodiment the heparin-like glycosaminoglycan is contacted with a modified heparinase II, wherein the modified heparinase II has the amino acid sequence of the mature peptide of SEQ ID NO: 2 wherein the histidine residue corresponding to position 440 of SEQ. ID NO: 2 is substituted with a residue selected from the group consisting of alanine, serine, tyrosine, threonine, and lysine to specifically cleave a heparin-like glycosaminoglycan.

In another embodiment the heparin-like glycosaminoglycan is contacted with a modified heparinase I, wherein the modified heparinase I has the amino acid sequence of the mature peptide of SEQ ID NO: 4 wherein at least one amino acid residue has been substituted and wherein the substitution is a substitution of a serine residue corresponding to position 377 of SEQ ID NO: 4 with a residue selected from the group consisting of alanine, serine, tyrosine, histidine, threonine, and lysine.

The modified heparinase in one embodiment may be used to remove active heparin from a heparin containing fluid. This may be accomplished by immobilizing the heparinase on a solid support.

In another embodiment the modified heparinase may be used to sequence heparin or heparin sulfate.

In one embodiment the method is a method for inhibiting angiogenesis and wherein an effective amount for inhibiting angiogenesis of the heparinase is administered to a subject in need of treatment thereof. Preferably the heparinase is administered to a tumor. In a preferred embodiment the heparinase is administered in a biodegradable, biocompatible polymeric delivery device. In another preferred embodiment the heparinase is administered in a pharmaceutically acceptable vehicle for injection. Preferably in each embodiment the heparinase is administered in an effective amount for diminishing the number of blood vessels growing into a tumor. Preferably an effective amount for inhibiting angiogenesis is between approximately one and four µg heparinase or a concentration of between 10 and 100 nM heparinase.

In another embodiment the heparinase is administered in a pharmaceutically acceptable vehicle for topical application to the eye. Preferably the heparinase is administered in an effective amount for diminishing the symptoms of an eye disease characterized by abnormal neovascularization.

In yet another embodiment the heparinase is administered in a pharmaceutical vehicle suitable for topical application. Preferably the heparinase is administered in an effective amount for diminishing the symptoms of psoriasis.

According to another aspect of the invention a method of specifically cleaving a heparan sulfate-like glycosaminoglycan is provided. The method includes the step of contacting a heparan sulfate containing fluid with the modified heparinase II of the invention. Preferably, the method is a method for inhibiting cellular proliferation.

The modified heparinase in one embodiment may be used to remove active heparan sulfate from a heparan sulfate containing fluid. This may be accomplished by immobilizing the heparinase on a solid support.

In one embodiment the heparan sulfate-like glycosaminoglycan is contacted with a substantially pure modified heparinase II, wherein the modified heparinase II has the amino acid sequence of the mature peptide of SEQ ID NO: 2 wherein the cysteine residue corresponding to position 348 of SEQ ID NO: 2 has been substituted with a residue selected from the group consisting of alanine, serine, tyrosine, histidine, threonine, and lysine to specifically cleave a heparin sulfate-like glycosaminoglycan.

A substantially pure heparinase is provided in another aspect of the invention. The heparinase is a polypeptide having the amino acid sequence of the mature peptide of SEQ ID NO: 2 wherein at least one amino acid residue has been substituted and wherein the substitution is selected from the group consisting of (a) a substitution of a cysteine residue corresponding to position 348 of SEQ ID NO: 2 with a residue selected from the group consisting of alanine, serine, tyrosine, histidine, threonine, and lysine; (b) a substitution of a histidine residue corresponding to position 440 of SEQ ID NO: 2 with a residue selected from the group consisting of alanine, serine, tyrosine, threonine, and lysine; and (c) a conservative substitution of a heparin-binding sequence corresponding to positions 446-451 of SEQ ID NO: 2. In one embodiment the heparinase is formulated as a pharmaceutical preparation comprising a sterile formulation of the heparinase and a pharmaceutically acceptable carrier.

According to another embodiment an immobilized substantially pure modified heparinase II is also provided. The immobilized substantially pure modified heparinase II includes the modified heparinase II described above, and a solid support membrane, wherein the modified heparinase II is immobilized on the solid support membrane.

According to another aspect the invention is an isolated nucleic acid including (a) an isolated nucleic acid encoding the substantially pure heparinase II described above;

(b) nucleic acids which hybridize under stringent hybridization conditions to the nucleic acid of SEQ ID NO:1 or to the complement of the nucleic acid of SEQ ID NO:1 and which are modified to encode a modified heparinase II described above; and (c) nucleic acids that differ from the nucleic acids of (b) in codon sequence due to the degeneracy of the genetic code.

In one embodiment the isolated nucleic acid is included in a recombinant host cell. In another embodiment the isolated nucleic acid is included in an expression vector.

In another aspect of the invention is a substantially pure modified heparinase II having the same activity as native heparinase II. The modified heparinase II differs from native heparinase II in the amino acid sequence and includes amino acid substitutions, deletions and/or additions of amino acids which are not essential to the enzymatic function of the heparinase such amino acids are described in more detail below.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE SEQUENCE LISTING

Figure 1:
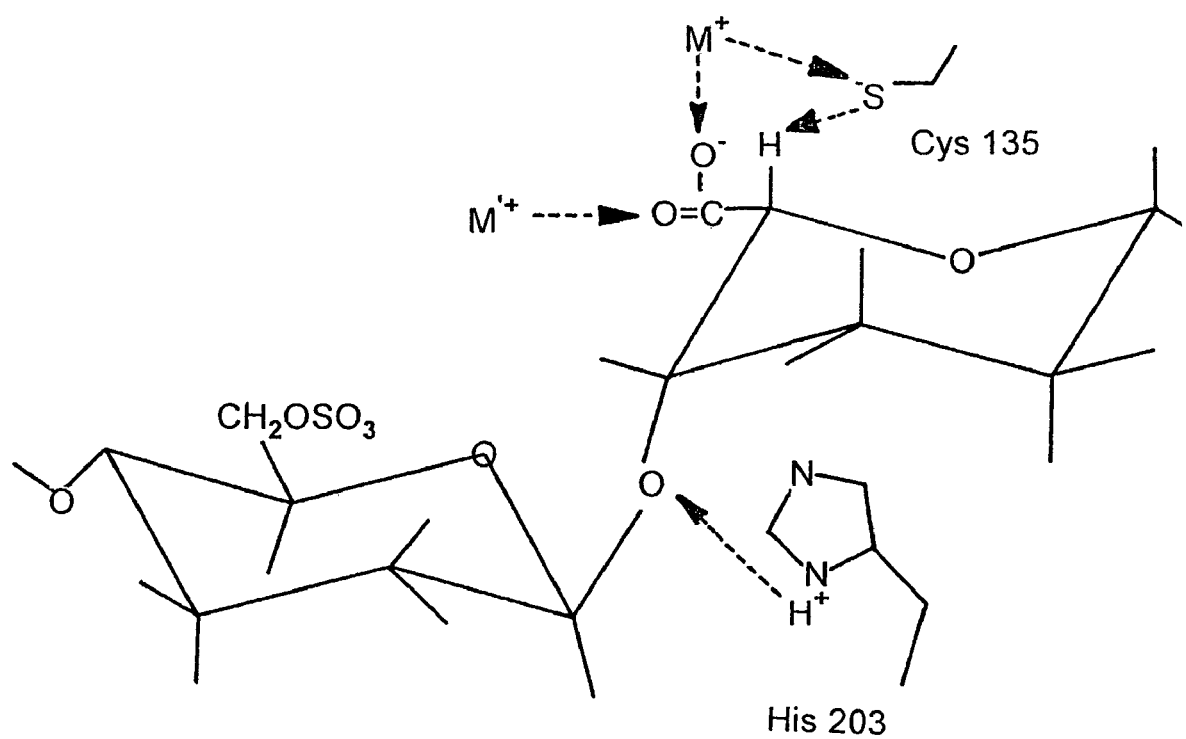
FIG. 1 is a schematic model of the catalytic domain of heparinase I.

SEQ ID NO:1 is the nucleotide sequence of the heparinase II gene.
SEQ ID NO:2 is the predicted amino acid sequence of the polypeptide encoded by the heparinase II gene.
SEQ ID NO:3 is the nucleotide sequence of the heparinase I gene.
SEQ ID NO:4 is the predicted amino acid sequence of the polypeptide encoded by the heparinase I gene.
SEQ ID NO:5 is a heparinase II peptide containing $Cys^{348}$.
SEQ ID NO:6 is a larger heparinase II peptide containing $Cys^{348}$.
SEQ ID NO:7 is a heparinase II peptide containing $His^{451}$.
SEQ ID NO:8 is a heparinase II peptide containing $His^{451}$.
SEQ ID NO:9 is a heparinase II peptide containing $His^{238}$.
SEQ ID NO:10 is a heparinase II peptide containing $His^{579}$.
SEQ ID NO:11 is a heparinase II peptide.
SEQ ID NO:12 is a heparinase II peptide.
SEQ ID NO:13 is a heparinase II peptide.
SEQ ID NO:14 is a heparinase II peptide.

DETAILED DESCRIPTION OF THE INVENTION

The present invention provides a series of new polysaccharide lyases derived from the heparinase I and II of *F. heparinum*. In particular, based upon a detailed structural and functional characterization of heparinase I and II, new heparinases with altered stability, activity and specificity are provided. The modified heparinases of the invention have many in vivo, in vitro and ex vivo utilities. For instance, they have great value in generating low molecular weight heparin or heparin fragments (or heparan sulfate) for clinical use. Additionally they can be used to neutralize heparin's anticoagulant function. Other uses are described herein.

The nucleotide and amino acid sequences of heparinase II are provided in SEQ ID NO: 1 and SEQ ID NO: 2 and of heparinase I are provided in SEQ ID NO: 3 and SEQ ID NO: 4, respectively. The sequence of heparinase I has been reported in Sasisekharan, R., Bulmer, M., Moremen, K., Cooney, C. L., & Langer, R. (1993) Proc. Natl. Acad. Sci. (USA) 90:3660-3664, U.S. Pat. No. 5,714,376, and PCT WO 97/16556. The sequence of heparinase II has been reported in U.S. Pat. No. 5,681,733, Su, H. et al, and is listed in Accession number 171364. These sequences have provided the first insight into the primary structure of the native heparinase I and II of *F. heparinum*.

The present disclosure provides a wealth of additional information about the secondary and tertiary structure of these heparinases as well as information relating to the functional roles of the various regions of the enzymes. This information is based upon detailed biochemical mapping of the active site and polysaccharide binding domain, characterization of these sites through kinetic studies, characterization of mutants created by site-directed mutagenesis, etc. The result is a detailed picture of the primary, secondary, and tertiary structures of heparinase I and II and the functional roles of various regions of the enzyme as well as the functions of specific mutants thereof.

The invention is based on several scientific findings. It was discovered according to the invention that various amino acid residues within heparinase I and II are essential to the catalytic function of these enzymes and can be modified to alter the enzymatic activity of these compounds. It was also discovered that other amino acid residues are not critical to the function of heparinase I and II and can be substituted or modified without affecting the activity of these compounds (e.g., cysteine 164 and cysteine 189 do not have a functional role in catalysis).

Heparinase I is a 42,500 Da enzyme isolated from the periplasm of *F. heparinum* that catalyzes the degradation of heparin-like glycosaminoglycans by cleaving heparin specifically in a random endolytic fashion (Linker, A., & Hoving, P. (1972) Methods in Enzymol. 28:902-911; Linhardt, R. J., Fitzgerald, G. L., Cooney, C. L., & Langer, R. (1982) *Biochem. Biophys. Acta* 702:197-203) at linkages of the type $H_{NS,6X}$-$I_{2S}$ or $H_{NS,6S}$-$I_{2X}$, where X is either sulfated or unsubstituted (Linhardt, R. J., Turnbull, J. E., Wang, H. M., Longanathan, D., & Gallagher, J. T. (1990) *Biochemistry* 29:2611-2617). The characteristic heparin degradation product profile includes $\Delta U_{2S}H_{NS}$ (disaccharide 1); $\Delta U_{2S}H_{NS,6S}$ (disaccharide 2), $\Delta U_{2S}H_{NS}I_{2S}H_{NS,6S}$ (tetrasaccharide 1), $\Delta U_{2S}H_{NS,6S}GH_{NS,6S}$ (tetrasaccharide 2), $\Delta U_{2S}H_{NS,6S}I_{2S}H_{NS,6S}$ (tetrasaccharide 3), and $\Delta U_{2S}H_{NS,6S}IH_{NAc,6S}GH_{NS,3S,6S}$ (hexasaccharide).

It is known that in heparinase I, the highly charged environment of the active site facilitates binding of the polyanionic heparin substrate through charge complimentarity (Sasisekharan, R. et al. (1998), *Biochemistry* 34, 1441-1448). Support for this finding includes the fact that charged reagents are much more facile inhibitors of heparinase I action as compared to neutral reagents. Heparinase I was found to be susceptible to IAA, but not IAM or NEM, an unusual situation in that IAM is generally considered to be more reactive than IAA towards cysteine residues. It is believed that the unusual reactivity observed with heparinase I was due to the charged environment of the active site facilitating partitioning of the charged reagent into the active site.

Heparinase II, also isolated from the periplasm of *F. heparinum*, catalyzes the degradation of both heparin-like and heparan sulfate-like glycosaninoglycans by cleaving specifically $H_{NY,6X}$-$I_{2X}$/$G_{2X}$-$H_{NY,6X}$, in which Y can be sulfated or acetylated and X can be sulfated or unsubstituted.

It was discovered according to the invention that the substrate binding and active site region of heparinase II surrounding $Cys^{348}$ is positively charged, similar to that of heparinase I, but that it is less charged than the active site region of heparinase I. Neutral modification reagents, such as IAM and NEM, inactivate heparinase II much more readily than the charged reagent IAA. As mentioned above it is believed that Heparinase I is susceptible to IAA, but not IAM or NEM, because the charged environment facilitates partitioning of the charged reagent into the active site. It is believed that this partitioning does not occur in heparinase II because IAA inhibits heparinase II activity less readily than IAM.

Additional evidence that the active site of heparinase II is charged, but less than the heparinase I active site, includes the observation that the decrease in inhibition by pCMB upon increasing salt concentration was much less marked for heparinase II than for heparinase I. For heparinase I, addition of 200 mM salt resulted in complete nullification of pCMB labeling of heparinase I. Conversely, for heparinase II, addition of even 500 mM salt still resulted in a first-order rate constant of inactivation of 0.06 $min^{-1}$.

Thus, the substrate binding environment which exists in heparinase II possesses some of the characteristics of the heparinase I binding pocket. Heparinase II possesses the ability to bind the highly charged heparin polymer through ionic interactions. Heparinase II, however, also maintains the ability to interact with the less ionic substrate heparan sulfate. It is believed that the lower ionic nature of the substrate binding pocket of heparinase II with respect to heparinase I, allows the heparinase II to be able to interact with both heparin and heparan sulfate, the data described in the Examples section below suggest that the $Cys^{348}$ of heparinase II functions as a base catalyst to abstract the C5 proton of iduronic acid within the heparin polymer. Functioning in this manner the $Cys^{348}$ can contribute to the degradation of heparin but not heparan sulfate. Thus, the data presented herein demonstrates that the substrate binding pocket of heparinase II includes two active sites, one containing $Cys^{348}$, that cleaves heparin and the other, that does not contain $Cys^{348}$, that cleaves heparan sulfate. The protection experiments described below in the Examples section also demonstrate that the two active sites are proximate to one another.

The data presented in the Examples also suggests a conserved enzymatic strategy among the heparinases for the breakdown of both heparin and heparan sulfate. Like heparinase I, heparinase II requires a cysteine to depolymerize heparin. In addition, like heparinase III, which does not contain any cysteines, heparinase II does not require a cysteine to depolymerize heparan sulfate.

The mapping studies also indicate that $Cys^{348}$ is proximate to $His^{451}$, another putative active site residue. Tritium labeling of the pCMB-reactive cysteine resulted in a peptide that did not contain a cysteine but did contain $His^{451}$. It is possible that $[^3H]$ NEM either labels the reactive histidine proximate to $Cys^{348}$ or that labeling of $Cys^{348}$ protects the histidine-containing peptide from proteolytic cleavage. In either case, this result suggests that $Cys^{348}$ and $His^{451}$ are both present in the active site of heparinase II.

It was also discovered according to the invention that although heparinase II contains three cysteines there are no disulfide bonds formed. Interaction with DTNB results in the modification of >2 cysteine residues. Unlike the highly ionic pCMB, which is present in low concentrations, and partitions almost exclusively to the active site, DTNB reacts with all three cysteines in heparinase II to a varying extent indicating none are involved in a disulfide bond. Aromatic disulfides in general, and DTNB in particular, react exclusively with free sulfhydryl groups.

It has also been found according to the invention that several histidine residues are critical for the catalytic activity of heparinase II. Through a combination of chemical modification, proteolytic mapping studies and site-directed mutagenesis, it has been found that histidines are essential amino acids in heparinase II. Mature native heparinase II contains 13 histidine residues.

The chemical modification data, described in the Examples below, points to three histidines that are solvent accessible, chemically more reactive towards modifying reagents, and essential for heparinase II activity. Further, the data indicates that different histidines must be involved in the enzymatic breakdown of heparin versus heparan sulfate. In both cases, a plot of log k versus log [DEPC] yielded a straight line with a slope of one indicating either that one histidine is modified or more than one histidine, all with the same apparent rate constant, are modified and are essential for the degradation of heparin versus heparan sulfate. Protection experiments further support this finding. With heparin as substrate, only heparin, but not heparan sulfate, was able to protect heparinase II from inactivation. With heparan sulfate as the substrate, neither heparin or heparan sulfate was able to protect heparinase II from DEPC inactivation. These results indicate that at least one histidine is proximate to the active site(s) since addition of substrate shields the histidine from modifying reagents, such as DEPC.

One possible interpretation of the above data is that the chemical modification of the reactive surface accessible histidines may alter the conformation of heparinase II, or impede substrate access to the active site and thereby affect heparinase II activity. Also, the substrate protection could somehow affect the chemical modification reaction and hence reduce the labeling kinetics. It is also possible that the reactive histidines are not in the active site, but rather they might be necessary for stability. If this were the case, then the protection experiments would be interpreted as showing that heparin binding stabilizes the correct tertiary structure of heparinase II, protecting the critical histidines from modification. However, when heparin or heparan sulfate are used for protection experiments with either substrates, only heparin is able to protect heparinase II when heparin is used as a substrate, and not heparan sulfate. This observation strongly points to the fact that the results of the protection experiments are not due to the artifacts caused or induced by heparin or heparan sulfate. In fact, when heparin is used as a substrate, heparan sulfate becomes a positive control and vice versa.

Proteolytic digests of heparinase II to map the histidine residues, were consistent with the chemical modification data. Mapping studies identified the three histidines that are modified by DEPC. The experiments demonstrated that at least histidines 238, 451 and 579 are essential for heparinase II activity.

Site-directed mutagenesis experiments further corroborated the chemical modification and peptide mapping experiments in the identification of histidines 238, 451 and 579 as being essential for heparinase II activity. Site-directed mutagenesis experiments indicated that histidines 238, 451 and 579 are essential for the enzymatic activity of heparinase II, as these three histidine to alanine mutations rendered the mutant enzymes enzymatically inactive towards both substrates. This data along with the chemical modification experiments can be interpreted to indicate that these three histidines are not only surface accessible and catalytically essential for heparinase I, but that these residues are also important structural elements of heparinase II.

Thus the data described in the Examples section, in particular, the biochemical and site-directed mutagenesis experiments together point to three histidines ($His^{238}$, $His^{451}$, and $His^{579}$) which play a key role in catalysis. It was also shown that $His^{451}$ plays a critical role in the breakdown of heparin because the addition of heparin to heparinase II protected this residue from DEPC modification. Additionally, the $His^{252}$, $His^{347}$, and $His^{440}$ mutants displayed differential activity towards heparin and heparan sulfate. For instance, the $His^{440}$ mutant displayed nearly the same enzymatic activity as recombinant heparinase II when heparan sulfate was used as the substrate, and displayed much less enzymatic activity towards heparin than recombinant heparinase II. These results demonstrate that the histidine 252, 347, and 440 residues can be manipulated to alter the substrate binding ability of heparinase II with respect to either heparin or heparan sulfate.

Mutant heparinases have also been developed which alter the ability of calcium to regulate the enzymatic activity of heparinase I. We find that calcium acts as a switch to turn heparinase on or off. As shown below there are several ways that the enzymatic properties of heparinase I can be rationally altered through modifying the calcium binding sites of heparinase I.

Initially, it was found that calcium plays a role in the processivity of heparinase I, that is, calcium allows the enzyme to bind to one end of the heparin chain and clip multiple times without releasing the substrate into solution. By modulating the calcium binding sites of heparinase I the enzyme can be made more or less processive (the wild type version of the enzyme is ~90% processive). A more processive enzyme would act faster and thus would be of use clinically for the digestion of heparin. A heparinase I mutant enzyme that is less processive would be of value in sequencing HLGAGs since intermediates would be released and could be identified.

Secondly, certain mutant forms of heparinase I, viz., S377A (where the amino acid serine 377 in wild type heparinase I is mutated to alanine), have been developed that result in a heparinase I enzyme that is calcium-independent, i.e., the enzyme is as active in the absence of calcium as it is in the presence of calcium. Such a mutant is of great of value because it has much less variability in activity as a function of the calcium in the surrounding environment. The wild type enzyme is ~10× more activity in 2 mm Ca++ than it is in the absence of calcium. The mutant does not exhibit this wide fluctuation in activity. Additionally the mutant can be used in the absence of calcium.

In light of the present disclosure, one of ordinary skill in the art is now able to rationally design new modified heparinases with altered activity and specificity. In particular, one is able to design heparinases with altered activity by modifying various residues involved in the regulation of enzymatic activity or calcium regulation of the enzyme, or by altering the positively charged residues surrounding the active site or the heparin binding domain. In addition, one is able to produce various other novel modified heparinases in which non-essential residues are freely changed or substituted conservatively.

The present invention provides for novel modified heparinases rationally designed on the basis of the sequence of the heparinase I and II of *F. heparinum* and the structural and functional characterizations disclosed herein.

In the description that follows, reference will be made to the amino acid residues and residue positions of native heparinase I and II disclosed in SEQ ID NO: 4 and 2 respectively. In particular, residues and residue positions will be referred to as "corresponding to" a particular residue or residue position of heparinase I or II. As will be obvious to one of ordinary skill in the art, these positions are relative and, therefore, insertions or deletions of one or more residues would have the effect of altering the numbering of downstream residues. In particular, N-terminal insertions or deletions would alter the numbering of all subsequent residues. Therefore, as used herein, a residue in a recombinant modified heparinase will be referred to as "corresponding to" a residue of the full heparinase I or II if, using standard sequence comparison programs, they would be aligned. Many such sequence alignment programs are now available to one of ordinary skill in the art and their use in sequence comparisons has become standard (e.g., "LALIGN" available via the Internet at http://phaedra.crbm-.cnrs-mop.fr/fasta/lalign-query.html). As used herein, this convention of referring to the positions of residues of the recombinant modified heparinases by their corresponding heparinase I or II residues shall extend not only to embodiments including N-terminal insertions or deletions but also to internal insertions or deletions (e.g, insertions or deletions in "loop" regions).

In addition, in the description which follows, certain substitutions of one amino acid residue for another in a recombinant modified heparinase will be referred to as "conservative substitutions." As used herein, a "conservative amino acid substitution" or "conservative substitution" refers to an amino acid substitution in which the substituted amino acid residue is of similar charge as the replaced residue and is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). Methods for making amino acid substitutions, additions or deletions are well known in the art and are described in detail in the Examples below.

Additionally, some of the amino acid substitutions are non-conservative substitutions. In certain embodiments where the substitution is remote from the active or binding sites, the non-conservative substitutions are easily tolerated provided that they preserve the tertiary structure characteristic of native heparinase, thereby preserving the active and binding sites.

In one aspect, the invention is a substantially pure heparinase which is a modified heparinase II having a modified heparinase II $k_{cat}$ value, wherein the modified heparinase II $k_{cat}$ value is at least 10% different than a native heparinase II $k_{cat}$ value. In a preferred embodiment, the modified heparinase II $k_{cat}$ value is at least 20% different than a native heparinase II $k_{cat}$ value. In another preferred embodiment the modified heparinase II $k_{cat}$ value is at least 50% different than a native heparinase II $k_{cat}$ value. A "modified heparinase II $k_{cat}$ value" as used herein is a measurement of the catalytic activity of the modified heparinase II enzyme with respect to either a heparin-like glycosaminoglycan substrate or a heparan sulfate-like glycosaminoglycan substrate. For instance, if a modified heparinase has 25% less activity with respect to a heparin-like glycosaminoglycan and 10% less activity with respect to a heparan sulfate-like glycosaminoglycan then the $k_{cat}$ value of the modified heparinase would be 25% different with respect to the heparin-like substrate and 10% different with respect to the to heparan sulfate. Thus, the $k_{cat}$ value is determined separately for each substrate.

The $k_{cat}$ value may be determined using any enzymatic activity assay which is useful for assessing the activity of a heparinase enzyme, such as the assays set forth in the Examples below. Several such assays are well-known in the art. For instance, an assay for measuring $k_{cat}$ is described in (Ernst, S. E., Venkataraman, G., Winkler, S., Godavarti, R., Langer, R., Cooney, C. and Sasisekharan. R. (1996) Biochem. J. 315, 589-597. The "native heparinase II $k_{cat}$ value" is the measure of enzymatic activity of the native heparinase II.

The modified heparinase may have a reduced enzymatic activity with respect to heparin or heparan sulfate. A "reduced enzymatic activity" is assessed by comparing the $k_{cat}$ value of the modified heparinase with that of native heparinase. Preferably the $k_{cat}$ value of the modified heparinase II will be less than or equal to 75% of the native heparinase II $k_{cat}$ value. A modified heparinase having reduced enzymatic activity with respect to heparin is one which has modifications in the residues essential for catalytic activity with respect to heparin. For instance, mutation of $Cys^{348}$, a residue which is involved in heparin binding, causes the heparinase II to have a reduced enzymatic activity with respect to heparin. This modification produces a modified heparinase II which becomes exclusively a heparan sulfate degrading enzyme. A modified heparinase II which has a reduced enzymatic activity with respect to heparan sulfate is one which has altered residues which are critical for heparan sulfate degrading activity. For instance, mutation of histidines 451, 238, and 579 of heparinase II produces modified heparinase II molecules having reduced enzymatic activity with respect to heparan sulfate. These modified heparinase II molecules also have reduced enzymatic activity with respect to heparin. Additionally, when histidine 440 is mutated in heparinase II, a modified heparinase II is produced which has reduced enzymatic activity with respect to heparin but which displays nearly the same enzymatic activity as native heparinase II when heparan sulfate is used as the substrate.

As used herein, with respect to heparinases, the term "substantially pure" means that the heparinases are essentially free of other substances with which they may be found in nature or in vivo systems to an extent practical and appropriate for their intended use. In particular, the heparinases are sufficiently free from other biological constituents of their hosts cells so as to be useful in, for example, producing pharmaceutical preparations or sequencing. Because the heparinases of the invention may be admixed with a pharmaceutically acceptable carrier in a pharmaceutical preparation, the heparinase may comprise only a small percentage by weight of the preparation. The heparinase is nonetheless substantially pure in that it has been substantially separated from the substances with which it may be associated in living systems.

In one embodiment, the modified heparinase II has the amino acid sequence of the mature peptide of SEQ ID NO:2 wherein at least one amino acid residue has been substituted and wherein the substitution is selected from the group consisting of (a) a substitution of a cysteine residue corresponding to position 348 of SEQ ID NO:2 with a residue selected from the group consisting of alanine, serine, tyrosine, histidine, threonine, and lysine; (b) a substitution of a histidine residue corresponding to at least one of positions 238, 440, 451, and 579 of SEQ ID NO:2 with a residue selected from the group consisting of alanine, serine, tyrosine, threonine, and lysine; and (c) a conservative substitution of a heparin-binding sequence corresponding to positions 446-451 of SEQ ID NO:2.

Mutation of $Cys^{348}$ to alanine or other conservative substitutions causes heparinase II to become exclusively a heparan-sulfate degrading enzyme. By mutation of $Cys^{348}$ to other amino acids such as serine, the ability of heparinase II to degrade heparin-like glycosaminoglycans can be fine tuned. Any amino acid which has the capacity to serve as a base within the active site of heparinase II could perform this function, e.g., tyrosine, threonine, lysine, serine, and histidine.

The histidine residues identified herein as important for heparinase II activity include histidine 451, 238, 440 and 579. Mutation of histidines 451, 238, and 579 to alanine results in some loss of activity towards both heparin and heparan sulfate, but the activity is not abolished. Thus, mutations of these residues produce an enzyme with lower activity towards both substrates. Mutation of histidine 440, however, displays differential activity towards heparin and heparan sulfate when mutated to alanine. Mutation of histidine 440 to alanine causes a greater loss in activity with respect to the heparin substrate than the heparan sulfate substrate.

Heparinase II also contains three heparin-binding sequences. For instance, sequence 446-451, including the histidine 451 residue, is a heparin-binding sequence. Mutations in this sequence can produce modified heparinase II molecules having increased or decreased activity towards heparin.

Based on the disclosure provided herein, those of ordinary skill in the art will easily be able to identify other modified heparinase II molecules having reduced enzymatic activity with respect to the native heparinase II molecule.

In another aspect, the invention is a substantially pure heparinase which is a modified heparinase II having a modified product profile, wherein the modified product profile of the modified heparinase II is at least 10% different than a native product profile of a native heparinase II. Preferably it is at least 20% or even at least 50%. A "modified product profile" as used herein is a set of degradation products produced by a modified heparinase which differ from the degradation products which are produced by a native heparinase under identical enzymatic conditions. The difference in the product profile may be due to the presence of different enzymatic products or simply in the number of enzymatic products formed by the modified heparinase compared to the native heparinase, or a combination of the two. For instance, the formation of different enzymatic products by a modified heparinase as opposed to the native heparinase, would constitute a modified product profile. Additionally, the production of the same types of enzymatic products but in a lesser or greater amount by the modified heparinase as opposed to the native heparinase, would also constitute a modified product profile. The product profile is determined separately for each substrate.

The product profile produced by a modified heparinase or a native heparinase may be determined by any method known in the art for examining the type or quantity of degradation product produced by heparinase. One preferred method for determining the type and quantity of product is described in Rhomberg, A. J. et al., *PNAS*, v. 95, p. 4176-4181 (April 1998), which is hereby incorporated in its entirety by reference. The method disclosed in the Rhomberg reference utilizes a combination of mass spectrometry and capillary electrophoretic techniques to identify the enzymatic products produced by heparinase. The Rhomberg study utilizes heparinase I and II to degrade heparin to produce heparin-like glycosaminoglycan oligosaccharides. MALDI (Matrix-Assisted Laser Desorption Ionization) mass spectrometry can be used for the identification and semiquantitative measurement of substrates, enzymes, and end products in the enzymatic reaction. The capillary electrophoresis technique separates the products to resolve even small differences amongst the products and is applied in combination with mass spectrometry to quantitate the products produced. Capillary electrophoresis may even resolve the difference between a disaccharide and its semicarbazone derivative. Detailed methods for sequencing polysaccharides and other polymers are disclosed in co-pending U.S. Patent Applications Ser. Nos. 60/130,792 and 60/130,747, both filed on Apr. 23, 1999 and having common inventorship. The entire contents of both applications are hereby incorporated by reference.

Briefly, the method is performed by enzymatic digestion, followed by mass spectrometry and capillary electrophoresis. The enzymatic assays can be performed in a variety of manners, as long as the assays are performed identically on the modified heparinase and the native heparinase, so that the results may be compared. In the example described in the Rhomberg reference, enzymatic reactions are performed by adding 1 mL of enzyme solution to 5 mL of substrate solution. The digestion is then carried out at room temperature (22° C.), and the reaction is stopped at various time points by removing 0.5 mL of the reaction mixture and adding it to 4.5 mL of a MALDI matrix solution, such as caffeic acid (approximately 12 mg/mL) and 70% acetonitrile/water. The reaction mixture is then subjected to MALDI mass spec. The MALDI surface is prepared by the method of Xiang and Beavis (Xiang and Beavis (1994) *Rapid. Commun. Mass. Spectrom.* 8, 199-204). A two-fold lower access of basic peptide $(Arg/Gly)_{15}$ is premixed with matrix before being added to the oligosaccharide solution. A 1 mL aliquot of sample/matrix mixture containing 1-3 picomoles of oligosaccharide is deposited on the surface. After crystallization occurs (typically within 60 seconds), excess liquid is rinsed off with water. MALDI mass spectrometry spectra is then acquired in the linear mode by using a PerSeptive Biosystems (Framingham, Mass.) Voyager Elite reflectron time-of-flight instrument fitted with a 337 nanometer nitrogen laser. Delayed extraction is used to increase resolution (22 kV, grid at 93%, guidewire at 0.15%, pulse delay 150 ns, low mass gate at 1,000, 128 shots averaged). Mass spectra are calibrated externally by using the signals for proteinated $(Arg/Gly)_{15}$ and its complex with the oligosaccharide.

Capillary electrophoresis is then performed on a Hewlett-Packard$^{3D}$ CE unit by using uncoated fused silica capillaries (internal diameter 75 micrometers, outer diameter 363 micrometers, $1_{det}$ 72.1 cm, and $1_{tot}$ 85 cm). Analytes are monitored by using UV detection at 230 nm and an extended light path cell (Hewlett-Packard). The electrolyte is a solution of 10 mL dextran sulfate and 50 millimolar Tris/phosphoric acid (pH2.5). Dextran sulfate is used to suppress nonspecific interactions of the heparin oligosaccharides with a silica wall. Separations are carried out at 30 kV with the anode at the detector side (reversed polarity). A mixture of a ⅕-naphtalenedisulfonic acid and 2-naphtalenesulfonic acid (10 micromolar each) is used as an internal standard.

Other methods for assessing the product profile may also be utilized. For instance, other methods include methods which rely on parameters such as viscosity (Jandik, K. A., Gu, K. and Linhardt, R. J., (1994), *Glycobiology*, 4:284-296) or total UV absorbance (Ernst, S. et al., (1996), *Biochem. J.*, 315:589-597) or mass spectrometry or capillary electrophoresis alone.

The invention in another aspect is a substantially pure heparinase which is a modified heparinase I wherein the modified heparinase I has enzymatic activity that is not dependent on the presence of calcium. The enzymatic activity of native heparinase I is calcium dependent. Heparinase I cleaves the glucosamine-uronic acid glycosidic bond of heparin-like glycosaminoglycans (HLGAG) by an eliminative mechanism leaving the uronic acid with an unsaturated C4-C5 bond. Heparinase I, however, does not degrade heparan-sulfate.

There are two putative "EF-hand" calcium coordinating motifs in heparinase I, CB-1 and CB-2, spanning residues 206-220 and 372-384 which are believed to be involved in calcium binding. CB-1 is part of the primary heparin binding site (residues 196-221) in heparinase I. It has been found, according to the invention that both CB-1 and CB-2 bind calcium and that this calcium binding can protect heparinase I from the inactivation caused by Woodward's regent K (WRK). The data also demonstrates that aspartate 210, 212, glycine 213, threonine 216 are important residues in calcium binding and/or enzyme catalysis and that glutamate 207 is not. It was also discovered that the residues in the second half of CB-1 (glycine 213 and threonine 216) are more important in calcium binding and/or enzymatic activity than the residues in the first half of CB-1 (glutamate 207, aspartate 210 and 212). Mutagenesis studies on CB-2 reveal that CB-2 appears to be more important than CB-1 in calcium binding and/or enzymatic activity.

Preferably the modified heparinase I has enzymatic activity that is not dependent on the presence of calcium. A modified heparinase I which is calcium independent may be prepared by modifying amino acids within the CB-1 or CB-2 regions which are essential for calcium binding but which will not alter the enzymatic activity of the heparinase. For instance, modification of serine 377 which is within the CB-2 region produces an enzymatically active heparinase which is not dependent on calcium.

The modified heparinases of the invention may be used to specifically cleave a heparin like glycosaminoglycan or a heparan sulfate like glycosaminoglycan by contacting each substrate with one of the modified heparinases of the invention. The invention is useful in a variety of in vitro, in vivo and ex vivo methods in which it is useful to cleave heparin-like glycosaminoglycans or heparan sulfate-like glycosaminoglycans.

In one embodiment when the modified heparinase is a modified heparinase which cleaves a heparin-like glycosaminoglycan, the method may be a method for inhibiting angiogenesis, wherein an effective amount for inhibiting angiogenesis of the heparinase is administered to a subject in need of treatment thereof. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in a generation of new blood vessels. Several of the angiogenic mitogens are heparin binding peptides which are related to endothelial cell growth factors. The inhibition of angiogenesis can cause tumor regression in animal models, suggesting a use as a therapeutic anticancer agent. Heparinases which specifically cleave a heparin like glycosaminoglycans function as inhibitors of angiogenesis by degrading the heparin involved in the elongation of the endothelial cells. The modified heparinases of the invention are useful because of their altered product profiles as well as requirements for enzymatic activity. For instance, a modified heparinase I having a serine 377 mutation to alanine specifically cleaves heparin-like glycosaminoglycans without cleaving heparan sulfate, similar to native heparinase I, but does not require calcium for its enzymatic activity. Therefore this enzyme has more therapeutic value for in vivo administration purposes.

An effective amount for inhibiting angiogenesis is an amount of heparinase which is sufficient to cause enzymatic degradation of heparin like glycosaminoglycans. Preferably that amount is an amount which is effective for diminishing the number of blood vessels growing into a tumor. This amount can be assessed in an animal model of tumors and angiogenesis, many of which are known in the art.

The modified heparinases are also useful for inhibiting neovascularization associated with eye disease. In another embodiment, the modified heparinase is administered to treat psoriasis. Psoriasis is a common dermatologic disease causes by chronic inflammation.

The modified heparinases of the invention are also useful for specifically cleaving a heparin sulfate-like glycosaminoglycan. Heparinases which cleave heparin sulfate-like regions are useful for inhibiting cellular proliferation.

The modified heparinases of the invention may also be used to remove active heparin from a heparin containing fluid. A heparin containing fluid is contacted with the modified heparinase of the invention to degrade the heparin. The method is particularly useful for the ex vivo removal of heparin from blood. In one embodiment of the invention the modified heparinase is immobilized on a solid support as is conventional in the art. The solid support containing the immobilized modified heparinase may be used in extracorporeal medical devices (e.g. hemodialyzer, pump-oxygenator) for systemic heparinization to prevent the blood in the devise from clotting. The support membrane containing immobilized heparinase I or II is positioned at the end of the device to neutralize the heparin before the blood is returned to the body.

In another aspect the invention is an immobilized substantially pure heparinase of the invention. The heparinase may be immobilized to any type of support but if the support is to be used in vivo or ex vivo it is desired that the support is sterile and biocompatible. A biocompatible support is one which would not cause an immune or other type of damaging reaction when used in a subject. The heparinase may be immobilized by any method known in the art. Many methods are known for immobilizing proteins to supports.

According to another aspect of the invention, there is provided methods for treating subjects in need of depletion of circulating heparin. Effective amounts of the modified heparinases of the invention are administered to subjects in need of such treatment. For example, subjects undergoing open heart surgery or hemodialysis often are in need of depletion of medically undesirable amounts of heparin in blood as a result of the surgery or hemodialysis. The subjects may be administered the modified heparinases of the invention in a manner and in amounts presently found acceptable when using native heparin. Effective amounts are those amounts which will result in a desired reduction in circulating heparin levels without causing any other medically unacceptable side effects. Such amounts can be determined with no more than routine experimentation. It is believed that doses ranging from 1 nanogram/kilogram to 100 milligrams/kilogram, depending upon the mode of administration, will be effective. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including oral, subcutaneous, intravenous, etc.

In general, when administered for therapeutic purposes, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

The present invention provides pharmaceutical compositions, for medical use, which comprise modified heparinase of the invention together with one or more pharmaceutically acceptable carriers and optionally other therapeutic ingredients. The term "pharmaceutically-acceptable carrier" as used herein, and described more fully below, means one or more compatible solid or liquid filler, dilutants or encapsulating substances which are suitable for administration to a human or other animal. In the present invention, the term "carrier" denotes an organic or inorganic ingredient, natural or synthetic, with which the active ingredient is combined to facilitate the application. The components of the pharmaceutical compositions also are capable of being commingled with the modified heparinases of the present invention, and with each other, in a manner such that there is no interaction which would substantially impair the desired pharmaceutical efficiency.

Compositions suitable for parenteral administration conveniently comprise a sterile aqueous preparation of the polysaccharide, which can be isotonic with the blood of the recipient. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

A variety of administration routes are available. The particular mode selected will depend, of course, upon the particular modified heparinase selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are parenteral routes. The term "parenteral" includes subcutaneous injections, intravenous, intramuscular, intraperitoneal, intra sternal injection or infusion techniques.

The compositions may conveniently be presented in unit dosage form and may be prepared by any of the methods well known in the art of pharmacy. All methods include the step of bringing the active modified heparinase into association with a carrier which constitutes one or more accessory ingredients. In general, the compositions are prepared by uniformly and intimately bringing the polymer into association with a liquid carrier, a finely divided solid carrier, or both, and then, if necessary, shaping the product. The polymer may be stored lyophilized.

Other delivery systems can include time-release, delayed release or sustained release delivery systems. Such systems can avoid repeated administrations of the heparinases of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

One of ordinary skill in the art, in light of the present disclosure, is now enabled to produce substantially pure preparations of any of these novel modified heparinases by standard recombinant technology. That is, one may substitute appropriate codons in SEQ ID NO: 1 or 3 to produce the desired amino acid substitutions by standard site-directed mutagenesis techniques. Obviously, one may also use any sequence which differs from SEQ ID NO: 1 or 3 only due to the degeneracy of the genetic code as the starting point for site directed mutagenesis. The mutated nucleic acid sequence may then be ligated into an appropriate expression vector and expressed in a host such as *F. heparinum* or *E. coli*. The resultant modified heparinase may then be purified by techniques well known in the art, including those disclosed below and in Sasisekharan, et al. (1993). As used herein, the term "substantially pure" means that the proteins are essentially free of other substances to an extent practical and appropriate for their intended use. In particular, the proteins are sufficiently pure and are sufficiently free from other biological constituents of their hosts cells so as to be useful in, for example, protein sequencing, or producing pharmaceutical preparations.

In another set of embodiments an isolated nucleic acid encoding the substantially pure modified heparinase of the invention is provided. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein the coding sequences are operably joined to regulatory sequences. Two DNA sequences are said to be operably joined if induction of a promoter in the 5' regulatory sequences results in the transcription of the coding sequence and if the nature of the linkage between the two DNA sequences does not (1) result in the introduction of a frameshift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Promoters may be constitutive or inducible. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, the term "stringent conditions" refers to parameters known to those skilled in the art. One example of stringent conditions is hybridization at 65° C. in hybridization buffer (3.5×SSC, 0.02% Ficoll, 0.02% polyvinyl pyrolidone, 0.02% bovine serum albumin (BSA), 25 mM $NaH_2PO_4$ (pH7), 0.5% SDS, 2 mM EDTA). SSC is 0.15M sodium chloride/0.15M sodium citrate, pH7; SDS is sodium dodecyl-sulphate; and EDTA is ethylene diamine tetra acetic acid. There are other conditions, reagents, and so forth which can be used, which result in the same degree of stringency. A skilled artisan will be familiar with such conditions, and thus they are not given here. The skilled artisan also is familiar with the methodology for screening cells for expression of such molecules, which then are routinely isolated, followed by isolation of the pertinent nucleic acid. Thus, homologs and alleles of the substantially pure modified heparinases of the invention, as well as nucleic acids encoding the same, may be obtained routinely, and the invention is not intended to be limited to the specific sequences disclosed.

For prokaryotic systems, plasmid vectors that contain replication sites and control sequences derived from a species compatible with the host may be used. Examples of suitable plasmid vectors include pBR322, pUC18, pUC19 and the like; suitable phage or bacteriophage vectors include λgt10, λgt11 and the like; and suitable virus vectors include pMAM-neo, pKRC and the like. Preferably, the selected vector of the present invention has the capacity to autonomously replicate in the selected host cell. Useful prokaryotic hosts include bacteria such as *E. coli, Flavobacterium heparinum, Bacillus, Streptomyces, Pseudomonas, Salmonella, Serratia*, and the like.

To express the substantially pure modified heparinases of the invention in a prokaryotic cell, it is necessary to operably join the nucleic acid sequence of a substantially pure modified heparinase of the invention to a functional prokaryotic promoter. Such promoter may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., *J. Bacteriol.* 162:176-182 (1985)) and the ζ-28-specific promoters of *B. subtilis* (Gilman et al., *Gene sequence* 32:11-20 (1984)), the promoters of the bacteriophages of *Bacillus* (Gryczan, In: *The Molecular Biology of the Bacilli*, Academic Press, Inc., NY (1982)), and *Streptomyces* promoters (Ward et al., *Mol. Gen. Genet.* 203:468-478 (1986)).

Prokaryotic promoters are reviewed by Glick (*J. Ind. Microbiol.* 1:277-282 (1987)); Cenatiempo (*Biochimie* 68:505-516 (1986)); and Gottesman (*Ann. Rev. Genet.* 18:415-442 (1984)).

Proper expression in a prokaryotic cell also requires the presence of a ribosome binding site upstream of the encoding sequence. Such ribosome binding sites are disclosed, for example, by Gold et al. (*Ann. Rev. Microbiol.* 35:365-404 (1981)).

Because prokaryotic cells will not produce the modified heparinases of the invention with normal eukaryotic glycosylation, expression of the modified heparinases of the invention of the invention by eukaryotic hosts is possible when glycosylation is desired. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO or CHO-K1, or cells of lymphoid origin, such as the hybridoma SP2/0-AG14 or the myeloma P3×63Sg8, and their derivatives. Preferred mammalian host cells include SP2/0 and J558L, as well as neuroblastoma cell lines such as IMR 332 that may provide better capacities for correct post-translational processing. Embryonic cells and mature cells of a transplantable organ also are useful according to some aspects of the invention.

In addition, plant cells are also available as hosts, and control sequences compatible with plant cells are available, such as the nopaline synthase promoter and polyadenylation signal sequences.

Another preferred host is an insect cell, for example in *Drosophila* larvae. Using insect cells as hosts, the *Drosophila* alcohol dehydrogenase promoter can be used (Rubin, *Science* 240:1453-1459 (1988)). Alternatively, baculovirus vectors can be engineered to express large amounts of the modified heparinases of the invention in insects cells (Jasny, *Science* 238:1653 (1987); Miller et al., In: *Genetic Engineering* (1986), Setlow, J. K., et al., eds., Plenum, Vol. 8, pp. 277-297).

Any of a series of yeast gene sequence expression systems which incorporate promoter and termination elements from the genes coding for glycolytic enzymes and which are produced in large quantities when the yeast are grown in media rich in glucose may also be utilized. Known glycolytic gene sequences can also provide very efficient transcriptional control signals. Yeast provide substantial advantages in that they can also carry out post-translational peptide modifications. A number of recombinant DNA strategies exist which utilize strong promoter sequences and high copy number plasmids which can be utilized for production of the desired proteins in yeast. Yeast recognize leader sequences on cloned mammalian gene sequence products and secrete peptides bearing leader sequences (i.e., pre-peptides).

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or which are subject to chemical (such as metabolite) regulation.

As discussed above, expression of the modified heparinases of the invention in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273-288 (1982)); the TK promoter of Herpes virus (McKnight, *Cell* 31:355-365 (1982)); the SV40 early promoter (Benoist et al., *Nature* (*London*) 290:304-310 (1981)); the yeast gal4 gene sequence promoter (Johnston et al., *Proc. Natl. Acad. Sci.* (*USA*) 79:6971-6975 (1982); Silver et al., *Proc. Natl. Acad. Sci.* (*USA*) 81:5951-5955 (1984)).

As is widely known, translation of eukaryotic mRNA is initiated at the codon which encodes the first methionine. For this reason, it is preferable to ensure that the linkage between a eukaryotic promoter and a DNA sequence which encodes the modified heparinases of the invention does not contain any intervening codons which are capable of encoding a methionine (i.e., AUG). The presence of such codons results either in the formation of a fusion protein (if the AUG codon is in the same reading frame as the modified heparinases of the invention coding sequence) or a frame-shift mutation (if the AUG codon is not in the same reading frame as the modified heparinases of the invention coding sequence).

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may, for example, provide for prototrophy to an auxotrophic host or may confer biocide resistance to, e.g., antibiotics, heavy metals, or the like. The selectable marker gene sequence can either be directly linked to the DNA gene sequences to be expressed, or introduced into the same cell by co-transfection. Additional elements may also be needed for optimal synthesis of the modified heparinases of the invention mRNA. These elements may include splice signals, as well as transcription promoters, enhancers, and termination signals. cDNA expression vectors incorporating such elements include those described by Okayama, *Molec. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as; for example, pBR322, ColE1, pSC101, pACYC 184, and πVX. Such plasmids are, for example, disclosed by Sambrook, et al. (*Molecular Cloning: A Laboratory Manual*, second edition, edited by Sambrook, Fritsch, & Maniatis, Cold Spring Harbor Laboratory, 1989)). *Bacillus* plasmids include pC194, pC221, pT127, and the like. Such plasmids are disclosed by Gryczan (In: *The Molecular Biology of the Bacilli*, Academic Press, NY (1982), pp. 307-329). Suitable *Streptomyces* plasmids include pIJ101 (Kendall et al., *J. Bacteriol.* 169:4177-4183 (1987)), and streptomyces bacteriophages such as φC31 (Chater et al., In: *Sixth International Symposium on Actinomycetales Biology*, Akademiai Kaido, Budapest, Hungary (1986), pp. 45-54). Pseudomonas plasmids are reviewed by John et al. (*Rev. Infect. Dis.* 8:693-704 (1986)), and Izaki (*Jpn. J. Bacteriol.* 33:729-742 (1978)).

Preferred eukaryotic plasmids include, for example, BPV, EBV, SV40, 2-micron circle, and the like, or their derivatives. Such plasmids are well known in the art (Botstein et al., *Miami Wntr. Symp.* 19:265-274 (1982); Broach, In: *The Molecular Biology of the Yeast Saccharomyces: Life Cycle and Inheritance*, Cold Spring Harbor Laboratory, Cold Spring Harbor, N.Y., p. 445-470 (1981); Broach, *Cell* 28:203-204 (1982); Bollon et al., *J. Clin. Hematol. Oncol.* 10:39-48 (1980); Maniatis, In: *Cell Biology: A Comprehensive Treatise*, Vol. 3, Gene Sequence Expression, Academic Press, NY, pp. 563-608 (1980)). Other preferred eukaryotic vectors are viral vectors. For example, and not by way of limitation, the pox virus, herpes virus, adenovirus and various retroviruses may be employed. The viral vectors may include either DNA or RNA viruses to cause expression of the insert DNA or insert RNA. Additionally, DNA or RNA encoding the modified heparinases of the invention polypeptides may be directly injected into cells or may be impelled through cell membranes after being adhered to microparticles.

Once the vector or DNA sequence containing the construct(s) has been prepared for expression, the DNA construct(s) may be introduced into an appropriate host cell by any of a variety of suitable means, i.e., transformation, transfection, conjugation, protoplast fusion, electroporation, calcium phosphate-precipitation, direct microinjection, and the like. After the introduction of the vector, recipient cells are grown in a selective medium, which selects for the growth of vector-containing cells. Expression of the cloned gene sequence(s) results in the production of the modified heparinases of the invention. This can take place in the transformed cells as such, or following the induction of these cells to differentiate (for example, by administration of bromodeoxyuracil to neuroblastoma cells or the like).

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Modification of Cysteine Residues Using pCMB and DTNB Inactivates Heparinase II Methods:

Chemicals and Materials. Urea, Tris, and TFA were from J T Baker (Phillipsburg, N.J.). DTT was obtained from Sigma. Sodium phosphate monobasic and dibasic and acetonitrile were from Mallinckrodt (Chesterfield, Mo.). Hydroxyapatite and BSA were purchased from Bio-RAD. The chemical modification reagents: IAA, IAM, 4-VP, NEM, pCMB, and DTNB were all purchased from Aldrich. 4-VP, NEM, and pCMB were used as received. IAA, IAM, and DTNB were recrystallized prior to use. All reagents were stored under nitrogen. Lys-C from *Achomobacter lyticus* (EC 3.4.21.50) was obtained from Wako Bioproducts (Richmond, Va.). [$^3$H] NEM was from New England Nuclear (Boston, Mass.). Heparin, from porcine intestinal mucosa with an average molecular weight of 12 kDa, was obtained from Hepar (Franklin, Ohio). Heparan sulfate, also derived from porcine intestinal mucosa, was from Celsus Laboratories (Cincinnati, Ohio). *Escherichia coli* BL21 (DE3) host was from Novagen (Madison, Wis.).

Heparinase II Activity Assay. Native heparinase II from *Flavobacterium heparinum*, was purified as described previously (Godavarti, R., and Sasisekharan, R (1996c) *Biochem. Biophys. Res. Comm.* 229, 770-777). The UV 232 nm assay to quantify native heparinase II enzymatic activity was similar to that reported for heparinase I (Bernstein, H., Yang, V. C., Cooney, C. L., Langer, R. (1988) *Meth. Enzym.* 137, 515-29). Briefly, the course of the reaction is monitored by measuring the increase in absorbance at 232 nm as a function of time under saturating substrate concentrations. With heparin as the substrate, the reaction was carried out at a concentration of 4 mg/ml in 50 mM sodium phosphate buffer, pH 7.3. With 2 mg/ml heparan sulfate, the reaction was measured in 50 mM sodium phosphate buffer, pH 6.9 (Sasisekharan, R., Moses, M. A., Nugent, M. A., Cooney, C. L., Langer, R. (1994) *Proc. Natl. Acad. Sci., USA* 91, 1524-1528). The temperature for all enzymatic activity measurements was kept constant at 35° C.

HPLC Analysis of Saccharide Products of Heparinase II Activity. Heparin or heparan sulfate was degraded by heparinase II or one of the recombinant heparinases for 18 h at 30° C. The reaction was stopped by boiling and the samples were injected onto a POROS Q/M (4.6×100 mm) anion-exchange column connected to a BIOCAD system (PerSeptive Biosystems, Framingham, Mass.) (Godavarti, R., and Sasisekharan, R (1996c) *Biochem. Biophys. Res. Comm.* 229, 770-777). A salt gradient of 0-2 M NaCl in 10 mM Tris pH 7.0 was run and products were monitored at 232 nm.

pCMB Modification Studies. (A) Inactivation with pCMB. Heparinase II (50 µg/ml) was incubated with 2.5-10 µM pCMB in 50 mM sodium phosphate buffer, pH 7.0, at 4° C. pCMB was prepared according to published procedures (Glazer, A., DeLange, R., Sigman, D. (1975) in *Laboratory Techniques in Biochemistry and Molecular Biology* (Work, T. S., and White, T. J., eds.), pp. 69-109, American Elsevier, New York). A control reaction mixture containing vehicle alone was run in tandem. At fixed time intervals, aliquots were withdrawn for the UV 232 nm enzyme activity assay.

(B) Reactivation of pCMB—modified heparinase II with DTT. Heparinase II (50 µg/ml) was incubated with 5 µM pCMB for 4 minutes and an aliquot was withdrawn to determine the fractional activity retained. DTT (10 mM) was then immediately added to the reaction mixture and to the control, which contained no pCMB. The mixtures were incubated at 4° C. Heparinase II activity was measured every half hour.

(C) Effect of salt on the inactivation of heparinase II by pCMB. Heparinase II was incubated with 5 µM pCMB in 50 mM sodium phosphate buffer, pH 7.0, with different salt concentrations (30, 60, 110, 180, 300, and 500 mM NaCl). A control mixture, which contained no additional salt, was also incubated with pCMB.

(D) Substrate protection of heparinase II against pCMB modification. Heparinase II (50 µg/ml) was preincubated with either 4 mg/ml heparin or 2 mg/ml heparan sulfate for 30 minutes prior to the addition of 5 µM pCMB and then the time course of inactivation was determined with the heparinase II activity assay.

(E) Quantification of pCMB—modified residues of heparinase II. Quantification of pCMB-modified residues of heparinase II was determined by difference spectra. At time zero, 19 µM pCMB was added to the sample cuvette containing heparinase II (825 µg/ml) in sodium phosphate buffer, pH 7.0. The change in absorbance at 250 nm was monitored every 30 seconds for 10 minutes. The number of modified residues was determined using $\in$=7,600 M$^{-1}$ cm$^{-1}$ (Boyer, P. D. (1952) *J. Am. Chem. Soc.* 76, 4331-4337). Heparinase II activity assays were completed under identical conditions with heparin as the substrate.

4-VP, NEM IAA, and AM Inactivation Heparinase II (100 µg/ml) was incubated with varying concentrations of either 4-VP, NEM, IAA or IAM (Lundblad, R. L. (1995) *Techniques in Protein Modification*. pp. 63-91, CRC Press, Boca Raton). Aqueous stock solutions (0.1 mM) of each reagent was prepared immediately before use. For NEM and 4-VP the concentrations of modifying reagent were varied from 0.2-2 mM. In the case of IAA or IAM, the concentrations of the reagent ranged from 1-10 mM. All reactions were conducted in 50 mM sodium-phosphate buffer, pH 7.0, at room temperature. The time course of inactivation was monitored in each case, time courses for each of the reagents were compared using either heparin or heparan sulfate as the substrate.

DTNB Modification Studies. (A) Inactivation with DTNB. Heparinase II (100 µg/ml) was incubated with DTNB (0.1-0.5 mM). A DTNB stock solution was made by dissolving DTNB in ethanol and an aliquot was added to the reaction mixture (Lundblad, R. L. (1995) *Techniques in Protein Modification*. pp. 63-91, CRC Press, Boca Raton). The control reaction mixture contained an equivalent amount of ethanol instead of DTNB; the amount of ethanol added was 3% of the total volume and did not have a measurable effect on enzymatic activity.

(B) Quantification of DTNB—modified residues of heparinase II. Quantification of DTNB-modified heparinase II residues was determined by difference spectra. At time zero, 2 mM DTNB was added to the sample cuvette containing heparinase II (825 µg/ml) in sodium phosphate buffer, pH 7.0. The change in absorbance at 410 nm was monitored every. 30 seconds for 10 minutes. To account for the decomposition of DTNB in the reaction mixture, a control was also done by monitoring the change in absorbance at 410 nm with only DTNB (2 mM) in 50 mM sodium phosphate buffer, pH 7.0. Heparinase II activity assays were also performed on the reaction mixture. The number of heparinase II cysteine residues modified was determined using $\in = 13,600$ M cm$^{-1}$ (Lundblad, R. L. (1995) *Techniques in Protein Modification.* pp. 63-91, CRC Press, Boca Raton). A similar experiment was completed after preincubating the enzyme with heparin for 30 minutes.

Results:

The reactivity of a panel of cysteine-specific reagents towards heparinase II was investigated. We not only sought to establish the importance, if any, of cysteine in heparinase II activity, but also sought to probe the chemical nature of the reactive cysteine(s). Two reagents in particular, pCMB and DTNB, were used extensively to chemically characterize the cysteines of heparinase II. Both these reagents, while considered cysteine specific, differ markedly in their chemical characteristics, thus together, they can provide a more complete picture of the environment and reactivity of heparinase's II cysteines than could an investigation using either reagent alone.

The effect of pCMB concentration on the inactivation of heparinase II was analyzed. Heparinase II (50 µg/ml) was incubated with various concentrations (i.e., 0-8 µM) of pCMB and a time course of inactivation was followed. The inactivation rate was concentration dependent through the range tested. pCMB showed the greatest reactivity towards heparinase II, completely inactivating heparinase II at 10 µM within 15 minutes. A plot of the ln (% activity) versus time yielded a straight line, the slope of which is the pseudo first-order rate constant. Upon plotting of the pseudo first-order rate constants as a function of pCMB concentration, the second-order rate constant for the inactivation was calculated to be 0.040 min$^{-1}$ µM$^{-1}$. The sulfhydryl-specific nature of the interaction was confirmed by the fact that the inactivation was readily reversed by the addition of 10 mM DTT.

To provide a foundation upon which to interpret other modification experiments, the inactivation kinetics of DTNB modification to heparinase II was also thoroughly investigated The inactivation rate, first order and second order rate constants were determined as for pCMB. A plot of the pseudo first order rate constants against the concentration of DTNB used (i.e., 0-0.5 mM) yielded a straight line with a second-order rate constant of 0.609 min$^{-1}$ mM$^{-1}$. A plot of the log k versus log [DTNB] confirmed that the reaction was first order in DTNB and suggested that one cysteine, modified by DTNB, was required for heparinase II activity. Identical rate constants of inactivation were obtained whether heparin or heparan sulfate was used as the substrate to monitor heparinase II activity. Like pCMB and DTNB, IAM, 4-VP, and NEM also inhibited heparinase II activity in a dose-dependent fashion. IAA was the least effective cysteine-specific reagent at inactivating heparinase II.

Having characterized the specific, stoichiometric interaction of pCMB and DTNB with the cysteines of heparinase II, we sought to extend the chemical modification studies with pCMB and DTNB to quantify the number of heparinase II cysteines modified by each reagent and correlate their modification with loss of enzymatic activity.

The interaction of pCMB with cysteine residues in 50 mM sodium phosphate pH 7.0 yields a mercaptide/cysteine adduct having an increased absorbance at 250 nm, characterized by a $\Delta\in = 7,600$ M$^{-1}$ cm$^{-1}$ (Boyer, P. D. (1952) *J. Am. Chem. Soc.* 76, 4331-4337). Taking advantage of this fact, we determined the relationship between the number of modified cysteines and loss of activity (as measured by A/Ao, the fractional remaining activity) to determine the number of essential cysteines in heparinase II that are modified by pCMB. A plot of fractional enzymatic activity remaining versus number of modified cysteines yielded a straight line with a slope near unity, suggesting that one cysteine in heparinase II is responsible for enzymatic activity. Upon incubation with 20 µM pCMB, loss of 98% activity was correlated with modification of 1.06 cysteines. In general, extrapolation to the y-axis of a plot of m versus A/Ao to determine the number of essential residues is appropriate in this case only if one cysteine is essential for activity and reacts much more readily with pCMB than the other two cysteines in heparinase II.

One possible role for a susceptible cysteine that, when modified, causes loss of enzymatic activity is that it is present in the active site of the enzyme. To attempt to understand whether the single reactive cysteine modified by pCMB was located at or near the active site of heparinase II, the enzyme was preincubated with either heparin or heparan sulfate before being subjected to chemical modification. Since the active site of the enzyme is presumably located proximately to the binding site for heparin and/or heparan sulfate, preincubation with one or both of the substrates should serve to shield such a cysteine from modification. With pCMB as the modification reagent, both heparin and heparan sulfate were able to protect the enzyme from inactivation although heparan sulfate was more effective (Table 1).

TABLE 1

| Substrate | Protection Reagent Used | | |
| --- | --- | --- | --- |
|  | None | Heparin | Heparan Sulfate |
| Heparin | 0.22 | 0.16 | 0.10 |
| Heparan Sulfate | 0.21 | 0.16 | 0.09 |

To confirm the analysis of the pCMB results and to extend them to determine the effect of heparin preincubation on the number of cysteines modified, DTNB was used to determine the number of cysteines modified with and without heparin preincubation. Heparinase II was incubated with 2 mM DTNB. One attribute of DTNB is that the 2-nitro-5-mercaptobenzoate anion released upon disulfide exchange with a cysteinyl residue is readily monitored ($\in = 13,600$ M$^{-1}$ cm$^{-1}$ at 410 nm) (Lundblad, R. L. (1995) *Techniques in Protein Modification.* pp. 63-91, CRC Press, Boca Raton) without interference from product formation ($\lambda_{max} = 232$ nm). Thus, it was uniquely suited, as compared to other reagents, to determining whether heparin preincubation has any effect on the number of cysteines modified. The number of cysteine residues modified by DTNB was measured as a function of time. After 10 minutes, an aliquot of the reaction mixture was removed and the activity of the protein determined. Without heparin preincubation, 2.4 cysteines were modified with a concomitant loss of 80% of the initial activity after 10 minutes. However, when the enzyme was preincubated with heparin, 1.3 cysteines, or approximately one less cysteine, was modified with only 25% loss of activity in the same period of time. The above experiments with pCMB and DTNB taken together demonstrate that one cysteine is surface exposed and can be protected from modification by heparin or heparan sulfate.

To examine the reactivity of the surface exposed "unique" cysteine in heparinase II that is modified by chemical reagents, the pH profile of pCMB inactivation was investigated at a pH range of 5-8. It is known that the mercaptide anion is more susceptible to chemical modification, especially by electrophilic compounds such as IAA and pCMB (Torchinsky, Y. (1981) *Sulfur in Proteins*, Pergamon Press, Inc., New York). Table 2 shows the pH profile of pCMB inactivation as a function of pH. There is very little pH dependence of the first-order rate constant of inactivation, less than a two-fold difference, indicating that the surface exposed cysteine is present in one ionic state from pH 5 to 8. Based on similar results with heparinase I and taking into account the high susceptibility of heparinase II to pCMB modification, it is probable that the surface exposed cysteine exists in the active site of heparinase II as the mercaptide anion.

TABLE 2

| | pH | | | |
|---|---|---|---|---|
| | 5.0 | 6.0 | 7.0 | 8.0 |
| k(min$^{-1}$) | 0.16 | 0.14 | 0.21 | 0.24 |

Together, the results of the chemical modification studies support the hypothesis that one cysteine in heparinase II is susceptible to chemical modification due to its high reactivity, and that this cysteine is surface exposed and located at or near the active site of heparinase II.

Example 2

The Chemical Environment in the Active Site Affects Thiol Reactivity

One mechanism by which a surface exposed reactive cysteine may exist in heparinase II at physiological pH is that the presence of nearby basic clusters serves to lower the pKa of the cysteine by stabilizing its mercaptide anion form through ionic interactions. To determine the effect, if any, of the ionic environment on the reactivity of the cysteine residue, inactivation of heparinase II by pCMB was investigated as a function of salt concentration. Heparinase II was incubated with 5 µM pCMB in 50 mM sodium phosphate pH 7.0 at 4° C. with increasing concentrations of salt (i.e., 0, 30, 60, 110, 180, 300, and 500 mM NaCl). After 1, 4, 7 and 10 minutes of incubation with pCMB, aliquots were withdrawn for activity measurements. Controls that contained only salt were run at the same time to account for loss of heparinase II activity solely due to increasing salt concentration. The first order rate constant of inactivation by pCMB decreased with increasing salt concentration. Between 0 and 300 mM NaCl, the rate decreased more than 4-fold, with a 2-fold drop occurring between 0 and 100 mM. The rate did not change significantly at concentrations higher than 300 mM NaCl. This decrease in the first order rate constant with increasing salt concentration indicated that the active site of heparinase II is charged, influencing the partitioning of ionic compounds such as pCMB and further indicated that this charge can be effectively masked by salt. The surface exposed reactive cysteine can be effectively masked from pCMB modification by salt, suggesting that this cysteine exists in an ionic environment that facilitates its reactivity.

Example 3

Lys-C Mapping of the Cysteines of Heparinase II

Methods:

[$^3$H]NEM Labeling and Lys-C Digest of Heparinase II. To determine which cysteine residues were modified by NEM and pCMB, mapping studies using the protease Lys-C were completed. In one study, heparinase II (1 nmole) was incubated with [$^3$H]NEM for thirty minutes. Unreacted [$^3$H]NEM was separated from the modified heparinase II by reverse phase HPLC (RPHPLC), the protein was concentrated by lyophilization, and digested with Lys-C under denaturing, nonreducing conditions.

In another study, heparinase II (3 nmol) was reacted with a stoichiometric amount of pCMB for 15 minutes. Less than 2% of total heparinase II enzymatic activity remained after this time interval. The protein was then denatured under strictly nonreducing conditions and reacted with an excess of IAM (4 mM). Modified heparinase II was separated and concentrated. pCMB was removed via addition of DTT. [$^3$H]NEM was added to the reaction mixture; unreacted tritium was separated by RPHPLC and heparinase II was digested with Lys-C.

Peptides derived from heparinase II digested by Lys-C, were separated by RPHPLC. The peptides were separated using a variation of the M-Stone gradient, which included a five minute isocratic phase (1.6% acetonitrile, 0.1% TFA) at the beginning of the run. Lys-C peptides were monitored at 210 nm and 277 nm, collected in microcentrifuge tubes and counted for tritium incorporation. The tritium-incorporated peptide peaks were sequenced using an Applied Biosystems Sequencer model 477 with an on-line model 120 PTH amino acid analyzer (Biopolymers Laboratory, MIT).

Results:

The chemical modification experiments point to a single surface exposed cysteine, in an ionic environment, as critical for heparinase II enzymatic activity. To identify the cysteine modified by pCMB, we sought to identify the reactive cysteine by labeling, digesting modified heparinase II, and isolating and sequencing the peptide containing the reacted cysteine. [$^3$H]NEM was used to label heparinase II. As pointed out earlier, like pCMB, NEM readily inhibits heparinase II in a dose-dependent fashion. However, unlike pCMB, NEM modification is not readily reversible making the NEM—cysteine adduct stable during proteolytic digest of heparinase II and subsequent analysis.

[$^3$H]NEM was incorporated into heparinase II, the protein was digested by Lys-C under non-reducing conditions and the resulting peptides were separated by RPHPLC. When the radioactivity of the resultant peaks was measured, it was found that [$^3$H] had been incorporated into four of the peptides. Peptide sequencing results indicated that two of the peptides represented sequences containing cysteine 348, one of the peptides, ld1, contained the sequence KDPNVEPHCK (SEQ ID NO: 5), the other peptide, ld12, was an incomplete proteolysis product with the sequence KYYTMPALLAG-SYYKDEYLNYEFLKDPNVEPHCK (SEQ ID NO: 6). The other two peptides contained sequences that could unambiguously be traced to heparinase II but that did not contain cysteines.

To determine whether cysteine 348 is the cysteine susceptible to modification by pCMB as well as NEM, the labeling and mapping study was completed again, but this time the pCMB reactive cysteine was labeled with [$^3$H]NEM. To accomplish this objective, pCMB—modified heparinase II was isolated, denatured, and then reacted with IAM to block the other two cysteines. Subsequently, pCMB labeling was reversed by addition of DTT and then the protein was labeled with [$^3$H]NEM. After overnight digestion by Lys-C and RPHPLC separation, analysis of the peptides resulted in three peaks being labeled. ld1 eluted at 42 minutes and was found to contain a peptide corresponding to SEQ ID NO:5, with cysteine 348. ld2 eluted at 62 minutes and was found to contain a peptide corresponding to SEQ ID NO:6, again containing cysteine 348. The third labeled peak, which did not have a cysteine—containing peptide, was also present in the control digest. These experiments identify and confirm that there is one cysteine (cysteine 348) in heparinase II that is uniquely reactive to chemical modification.

The mapping studies indicate that $Cys^{348}$ is probably proximate to $His^{451}$, another putative active site residue described herein. Tritium labeling of the pCMB—reactive cysteine resulted in a peptide that did not contain a cysteine but did contain $His^{451}$. It is possible that [$^3$H] NEM either labels the reactive histidine proximate to $Cys^{348}$ or that labeling of $Cys^{348}$ protects the histidine-containing peptide from proteolytic cleavage. In either case, this result suggests that $Cys^{348}$ and $His^{451}$ are both present in the active site of heparinase II.

Example 4

Site-Directed Mutagenesis and Recombinant Expression

Methods:

Mutagenesis and cloning of mutant heparinase II. The C164A, C189A, and C348A mutations were introduced by the overlap extension PCR methodology (Higuchi, R. (1990) in PCR Protocols: A Guide to Methods and Applications (Innis, M. A., Gelfand, D. H., Sninsky, J. J., and White, T. J., eds.), pp. 177-183, Academic Press, Inc, San Diego, Calif.) via 15 cycle PCR. PCR products were concentrated by spin column (Invitrogen, Carlsbad, Calif.) and subcloned into pCR 2.1. The authenticity of all mutations was verified by sequencing. Heparinase II and the three mutants were cleaved from pCR 2.1 via restriction digest with Nde I/Sac I and cloned into pSE02 for expression. pSE02 is a construct derived from pET28a which contains a His-Tag, for purification purposes, and an OmpT leader sequence for periplasmic export.

Expression, Isolation, and Purification of r-Heparinase II and Mutants in *E. coli*. The recombinant and mutant heparinases II were expressed with the putative *F. heparinum* leader sequence. Overnight cultures of BL21 were induced with IPTG in mid-log phase (O.D. 0.7-0.9) and allowed to grow for another four hours at room temperature at which time the cells were harvested as described previously (Ernst, S., Venkataraman, G., Winkler, S., Godavarti, R., Langer, R., Cooney, C. L., Sasisekharan, R. (1996) *Biochem. J.* 315, 589-597).

The cell pellet was resuspended in one-fiftieth of the original volume of 50 mM sodium phosphate, 50 mM NaCl pH 7.0. The resuspended culture was placed on ice and sonicated as described previously. The soluble portion of the cell lysate was isolated by centrifugation at 14,000 rpm for 20 minutes at 4° C. and then purified by hydroxyapatite chromatography. Briefly, before addition of the supernatant, the hydroxyapatite column was equilibrated with 50 mM sodium phosphate, 50 mM NaCl, pH 7.0 by washing with 5 column volumes. The 2 ml of supernatant was applied, followed by two washes with 50 mM sodium phosphate, 100 mM NaCl and 50 mM sodium phosphate, 200 mM NaCl. r-Heparinase II and the mutants were eluted by addition of 3 ml of 50 mM NaCl, 500 mM NaCl. SDS-Page was carried out using precast 10% gels and a Mini Protean II apparatus, and stained with the Silver Stain Plus kit (Bio-Rad) to verify protein purity. Exhaustive digests of both 4 mg/ml heparin and 2 mg/ml heparan sulfate were completed and the resulting products analyzed with a Perfusion Chromatography system in a fashion similar to the analysis completed for heparinase I (Godavarti, R., and Sasisekharan, R (1996c) *Biochem. Biophys. Res. Comm.* 229, 770-777). Running buffer used as 10 mM Tris, pH 7.0 and the salt gradient was 0-2 M NaCl over the course of ten minutes. Quantification of protein concentrations were determined using the Micro BCA reagent (Pierce Inc., Rockford, Ill.) relative to a BSA standard.

Results:

To confirm the role of cysteine 348 as the reactive cysteine required for heparinase II activity, cysteine to alanine mutants were created for each of the three cysteines (C164A, C189A, C348A). In each case protein production was induced by addition of IPTG and the protein was purified by hydroxyapatite chromatography. The recombinant proteins were analyzed by silver stain gel and found to be pure. Recombinant heparinase II was found to have a similar degradation product profile as native heparinase II with both heparin and heparan sulfate as substrates.

Each of the cysteine mutants (i.e., C164A, C189A, and C348A) and r-heparinase II as a control, were expressed in BL21. After purification, each of these four wild-type and mutant enzymes was characterized via exhaustive (i.e., 18 hours at 30° C.) substrate digests to determine product profiles. Perfusion chromatography profiles of the desaccharide products of the three cysteine mutants and the r-heparinase II were analyzed using either heparin and heparan sulfate as the substrate.

Both C164A and C189A had disaccharide product profiles that closely matched those of both r-heparinase II and native heparinase II. Interestingly, the C348A mutant was completely inactive towards heparin. In contrast, all three mutants gave product profiles very similar to that of wild type heparinase when heparan sulfate was used as the substrate. Taken together with the mapping studies and the chemical modification studies, cysteine 348 is proposed to be an essential residue in heparinase II involved in the breakdown of heparin but not heparan sulfate.

This study has demonstrated through a combination of chemical modification and site-directed mutagenesis experiments that cysteine 348 is an essential residue for catalysis in heparinase II. The chemical modification data unambiguously points to the fact that there is one cysteine that is solvent accessible and chemically more reactive towards modifying reagents than the other two cysteines. Protection experiments suggest that this cysteine is proximate to the active site since addition of substrate, either heparin or heparan sulfate, shields the cysteine from modifying reagents, such as pCMB and DTNB. One possible interpretation of the above data is that the chemical modification of the reactive surface accessible cysteine may alter the conformation of heparinase II, or impede substrate access to the active site and thereby affect heparinase II activity. Also, the substrate protection could somehow affect the chemical modification reaction and hence reduce the labeling kinetics. It is also possible that the reactive cysteine is not in the active site, but rather is necessary for stability. If this were the case, then the protection experiments would be interpreted as showing that heparin binding stabilizes the correct tertiary structure of heparinase II, protecting the critical cysteine from modification. While the above interpretations cannot be disproven, several points argue for a catalytic role of cysteine 348. First, $Cys^{348}$ is unusually reactive towards pCMB (and the modification is readily reversed upon addition of a sulfhydryl reagent like DTT) and is ionized at physiological pH. Second, CD profiles of native heparinase II and pCMB-modified heparinase II are superimposable indicating there are no gross distortions in the secondary structure of heparinase II upon binding of pCMB.

Of interest is the fact that, upon chemical modification, enzymatic activity towards both heparin and heparan sulfate is inhibited to the same extent, but the C348A mutant is able to catalyze the breakdown of heparan sulfate, but not heparin. These results may be interpreted to mean that there is one substrate binding domain in heparinase II that accommodates both heparin and heparan sulfate. Within this binding domain, specific amino acids are involved in the active site chemistry that affords the enzymatic breakdown of heparin; within this same binding domain separate amino acids are involved in the breakdown of heparan sulfate. $Cys^{348}$ is one residue that is required for the enzymatic cleavage of heparin but is not required for breakdown of heparan sulfate. However, addition of a bulky adduct from a modifying reagent presumably disrupts essential protein-substrate interactions that are critical for breakdown of either heparin or heparan sulfate within the substrate binding domain. This interpretation is also consistent with the observation that preincubation with heparan sulfate affords greater protection from modifying reagents, since heparan sulfate is known to bind to heparinase II with greater affinity.

Example 5

Terbium Specifically Interacts with Heparinase L

In an effort to further understand the mechanism by which heparinase I cleaves its polymer substrate, we sought to understand the role of calcium, as a necessary cofactor, in the enzymatic activity of heparinase I. Specifically, we undertook a series of biochemical and biophysical experiments were performed (and described below) to answer the question of whether heparinase I binds to calcium, and if so, which regions of the protein are involved in calcium binding. Using the fluorescent calcium analog terbium, we have found that heparinase I tightly binds divalent and trivalent cations. Further, we have established that this interaction is specific for ions that closely approximate the ionic radius of calcium. Through the use of the modification reagents Woodward's Reagent K and EDC, we have shown that the interaction between heparinase I and calcium is essential for proper functioning of the enzyme. Preincubation with either calcium alone or calcium in the presence of heparin is able to protect the enzyme from inactivation by these modifying reagents. In addition, through mapping studies of Woodward's Reagent K modified heparinase I, we have identified two putative calcium binding sites in heparinase I which are specifically modified by WRK leading to loss of enzyme activity.

Methods:

Chemicals and Materials. EDTA and MOPS were obtained from Sigma. Chelex Resin was purchased from Bio-RAD. $TbCl_3$, $LuCl_3$ and $CaCl_2$ as well as the chemical modification reagents WRK, EDC and glycine methyl ester were all purchased from Aldrich. EDC was used as received, WRK was recrystallized prior to use. Trypsin was obtained from Boehringer Mannheim. Heparin, from porcine intestinal mucosa with an average molecular weight of 12 kDa, was obtained from Celsus Laboratories (Franklin, Ohio). All other reagents were obtained as described in Example 1.

Heparinase I Activity Assay. The UV 232 nm assay to quantify heparinase I enzymatic activity was similar to that described in Example 1. With heparin as the substrate, the reaction was carried out at a concentration of 4 mg/ml in 100 mM MOPS, 5 mM calcium acetate, pH 7.0. The temperature for all enzymatic activity measurements was kept constant at 30° C. For the inactivation kinetic profiles, activity was measured as outlined above at precise time points.

Terbium Titrations of Heparinase I. The titrations of heparinase I with terbium were completed by adding aliquots of a terbium stock solution (in 10 mM MOPS, 0.1M KCl, pH 6.5) to a solution containing heparinase I (4.6 µM). To maintain a constant protein concentration, the same amount of heparinase I (4.6 µM) was present in the terbium stock solution as was present in the cuvette. The concentration of the terbium solution was determined by EDTA titration in the presence of a xylenol orange indicator. To ensure accurate readings, all solutions, except the terbium stock solution were run through a chelating column (Chelex Resin) to remove trace contaminants. After addition of a terbium aliquot, the sample was mixed and allowed to come to equilibrium for 15 minutes. Fluorescence measurements were recorded on a FluoroMax fluorescence spectrometer (Spex Instruments, Edison, N.J.). The geometry of fluorescence detection was 90°. All measurements were recorded using a quartz cell (Starna Cells) with a 1.0 cm path length, and the sample temperature was maintained at 25° C. using a circulating water-bath.

For the calcium competition titrations, to a solution of heparinase I (4.6 µM) plus eight molar equivalents of terbium was added aliquots of a 50 mM calcium solution that also contained 4.6 µM heparinase I. After each addition, the solution was thoroughly mixed and the solution allowed to stand for 15 minutes before a measurement was taken. In none of the experiments was protein precipitation evident.

Results:

Heparinase I requires calcium for activity, showing a five-fold increase in activity upon introduction of millimolar concentrations of calcium. In addition, heparinase I contains two putative calcium binding motifs, one present near the heparin binding domain which has been shown to be important for heparinase I activity; the other of which is present in the C-terminus region of heparinase I. Thus, these results are consistent with the binding of calcium by heparinase I and with this interaction being critical for enzymatic activity. However, it is also known that calcium interacts in a highly specific way with heparin, inducing a conformational change in the polymer chain. Thus, another possibility is that heparinase I can only act on the calcium-induced conformation of heparin. If this were the case, then the enzymatic activity of heparinase I could be affected by increasing calcium concentration without any direct interaction between calcium and the enzyme.

To address whether heparinase I itself binds calcium, we studied the interaction of terbium ($Tb^{3+}$) with heparinase I in the absence of heparin. In this way, interactions of heparinase I with terbium could be studied independently of confounding factors associated with heparin-terbium interactions. $Tb^{3+}$ is a lanthanide calcium analog often used to probe the nature of protein interactions with calcium. $Tb^{3+}$ possesses an ionic radius that is very similar to calcium in aqueous solution and has the advantage, that unlike calcium, the protein-Tb$^{3+}$ adduct is fluorescent. In addition, because of the increase in charge properties of terbium versus calcium (i.e., 3+ as opposed to 2+), terbium very often has a higher affinity for calcium binding sites than does calcium itself.

Upon titration of heparinase I with terbium in the absence of heparin, an increase in fluorescence was observed whether excitation was performed at 488 nm (direct excitation of the terbium adduct) or at 280 nm (excitation of nearby tyrosine side chains, followed by energy transfer to the terbium adduct). Since, as has been observed with other protein systems, the fluorescence signal was enhanced upon indirect excitation at 280nm, the most extensive studies were completed in this way. Fluorescence intensity increased upon titration of terbium to heparinase I until 10 terbium equivalents had been added. Beyond this point, the fluorescence intensity did not increase further.

To ensure that the terbium-heparinase I interaction was specific, the ability of calcium to compete with terbium for binding to heparinase I was investigated. Since, as noted above, erbium very often can have a 1000-fold higher affinity for calcium binding sites than does calcium, a large excess of calcium is required to reduce the binding of terbium to a protein. Specifically, in the case of heparinase I, after addition of 8 equivalents of terbium to heparinase I, calcium was added to the enzyme-terbium solution and the fluorescence was measured. Addition of calcium concentrations up to 2 mM were able to compete terbium off of heparinase I. Addition of calcium concentrations in excess of 2 mM resulted in only a minimal further decrease in relative fluorescence, suggesting that 2 mM calcium was sufficient to compete with terbium for binding to heparinase I. These results indicate that the interaction of terbium with heparinase I is highly specific and that this interaction substitutes for calcium binding to heparinase I.

Example 6

Inactivation of Heparinase I with Tb$^{3+}$ or Lu$^{3+}$

Methods

Effect of Lanthanides on Heparinase I Activity. To determine the effect of Tb$^{3+}$ and Lu$^{3+}$ on heparinase I activity, heparinase I was preincubated for 15 minutes with increasing amounts of either Tb$^{3+}$ and Lu$^{3+}$ in a 10 mM MOPS, 0.1M KCl, pH 6.5 solution. The range of lanthanide tested was 1 µM-10 mM. At this point, the activity of the heparinase I solution was measured using the 232 nm assay. The substrate solution was 4 mg/mL heparin, 5 mM calcium in 10 mM MOPS, 0.1 M KCl, pH 6.5. The concentrations of the lanthanide stock solutions were determined as outlined above. Control reactions were run in the absence of lanthanide.

Results:

In an effort to confirm and extend the conclusions of the fluorescence study, the effect of terbium on heparinase I activity was determined. Heparinase I activity was inhibited in a dose-dependent fashion by terbium with a measured IC$_{50}$ of 39 µM. This type of inhibition has been seen for other enzyme systems known to interact specifically with calcium. The effect of another lanthanide, lutetium, on heparinase I activity was also investigated. The ionic radius of Lu$^{3+}$ is smaller than that of Tb$^{3+}$, therefore, we expected that Lu$^{3+}$, a less suitable replacement for calcium in heparinase I, would be a less potent inhibitor of heparinase I activity. Indeed, although Lu$^{3+}$ was also able to inhibit heparinase I activity, the IC$_{50}$ was increased to 212 µM. Together with the fluorescence experiments, these results indicate that heparinase I interacts in a highly specific manner with terbium and, by extension, with calcium.

Example 7

Inactivation of Heparinase I by Chemical Modification with Woodward's Reagent K (WRK) and EDC Methods:

Formation and Degradation of the Keto Ketenimine Intermediate from WRK. Upon addition of WRK to an enzyme solution, the actual agent that modifies nucleophilic amino acids is not WRK itself, rather WRK is converted into a reactive intermediate which binds to selective amino acids in a protein. Therefore, to accurately model the kinetics of WRK modification of heparinase I, it is necessary to know the concentration of this intermediate, the keto ketenimine, as a function of time. The concentration of the keto ketenimine, and thus the rates of its formation and degradation, can be determined by monitoring an aqueous solution of WRK at 340 nm, where the keto ketenimine is the only species of WRK that absorbs appreciably ($\in$=4,730 cm$^{-1}$ M$^{-1}$). At pH 6.0, 6.5, and 7.0, the conversion of 50 µM WRK to the keto ketenimine and its subsequent degradation was determined in 100 mM MOPS by monitoring the change in absorbance at 340 nm every 30 seconds for 10 minutes. Stock solutions of WRK were made fresh with 0.1 M HCl at 4° C. A cuvette containing an equivalent amount of 0.1 M HCl instead of WRK was used as a blank. Similar procedures were used for 500 µM WRK in 100 mM succinic acid at pHs of 5.0, 5.5, and 6.0. To determine the rate constants of formation (k") and degradation (k') of the keto ketenimine, the following equation was used, $$[I] = \frac{k''}{k'' - k'}[W]_0 e^{-k't} - \frac{k''}{k'' - k'}[W]_0 e^{-k''t}$$

In this equation t is the measured time, [I] is the concentration of the ketoketenimine intermediate, and [W]$_0$ is the initial concentration of WRK (either 50 µM or 500 µM).

pH Dependence of Inactivation of Heparinase I with WRK. Heparinase I (30 µg/ML) was inactivated with 0.1 mM-2 mM WRK at room temperature. The control mixture contained no WRK but an equivalent amount of 0.1 M HCl. Reactions were carried out in 100 mM succinic acid at pH 5.0, 5.5 and 6.0 and in 100 mM MOPS at pH 6.0, 6.5 and 7.0. At fixed time intervals, aliquots were withdrawn for the UV 232 nm activity assay. The kinetics of WRK inactivation of heparinase I were determined by plotting the natural log of percent activity versus an adjusted time term (to account for the formation and decomposition of the keto ketenimine intermediate). This adjusted time term was calculated according to the following equation:

$$t'' = \frac{k''}{k'' - k'}\left(\frac{1 - e^{-k't}}{k'} - \frac{1 - e^{-k''t}}{k''}\right)$$

Results:

The amino-acid specific modification of heparinase I to delineate essential residues in its enzymatic activity has been described in co-pending PCT Patent Application WO 97/16556, claiming priority to U.S. Provisional Patent Application Ser. No., 60/008,069, and the related U.S. National Phase patent application, (60/066,481), which is hereby incorporated by reference. Specifically, cysteine specific reagents pCMB and IAA were used to identify cysteine 135 as essential and the histidine specific reagent DEPC was used to identify the catalytically critical histidine 203. The focus of the present studies was to determine whether the first, second, or both putative calcium binding sites were important for heparinase I activity using modification reagents specific for carboxylate groups. Therefore, the effect of WRK and EDC on heparinase I activity was investigated.

Formation and Degradation of the Keto Ketenimine Intermediate from WRK. In an effort to understand the modification kinetics of heparinase I by WRK, the rates of formation and degradation of the keto ketenimine were followed. The results were fit to a nonlinear equation as outlined above. Keto ketenimine concentration peaked at a level of about 0.03 mM within 35 seconds. This was followed by a gradual decrease in concentration to less than 0.005 mM by 210 seconds. The derived rate constants for the formation (0.061 sec$^{-1}$) and degradation (0.019 sec$^{-1}$) of the keto ketenimine were used to accurately determine the kinetics of heparinase I inactivation by WRK.

WRK and EDC inactivate heparinase I in a dose-dependent way. Having determined the kinetics of keto ketenimine formation, the kinetics of WRK inactivation were delineated. WRK was found to inhibit heparinase I in a dose-dependent fashion through the range of 0-400 μM WRK. Plotting the pseudo-first order rate constants as a function of the WRK concentration yielded a second order rate constant of 7.9 mM$^{-1}$ min$^{-1}$.

To ensure that the reaction was specific to carboxylate residues, the effect of another carboxylate-specific reagent, EDC, on heparinase I activity was determined. Similar to what was seen for WRK, EDC (in the millimolar range) was found to inhibit heparinase I in a dose-dependent fashion.

Example 8

Calcium and Heparin Protect Heparinase I from WRK-Mediated Inactivation

Methods:

$Ca^{+2}$ Protection of WRK Inactivation of Heparinase L. To investigate the ability of $Ca^{+2}$ to protect the enzyme against modification by WRK, heparinase I (30 μg/mL) was first incubated with different concentrations of $Ca^{+2}$, ranging from 100 μM to 20 mM, for 30 minutes at pH 7 before 50 μM WRK was added to the reaction mixtures. The time course of inactivation was then determined. An activity assay was also performed with a control mixture with no prior addition of $Ca^{+2}$.

Results:

If WRK modifies the calcium binding domain(s) of heparinase I leading to inactivation because of disrupting interactions critical for proper enzymatic functioning, then preincubation with either calcium or heparin, or both, should offer some protection from inactivation. To determine whether this is the case, heparinase I was preincubated for 30 minutes with either calcium, heparin or heparin and 5 mM $Ca^{+2}$. Heparin was able to partially protect the enzyme from inactivation, however, preincubation with heparin and calcium was able to almost completely protect the enzyme from inactivation. Preincubation with increasing amounts of calcium was found to protect heparinase I from WRK-mediated inactivation, with a $K_{0.5}$ of 980 μM. At large calcium concentrations, calcium alone ($\kappa_{inact}$=2.1 min$^{-1}$) protected heparinase I about half as well as heparin plus calcium ($\kappa_{inact}$=1.2 min$^{-1}$).

Example 9

Mapping of Residues in Heparinase I Modified by WRK

Methods:

Tryptic Digest and Protein Sequence Analysis. Tryptic digest of the samples was performed as described previously. To 16 μg of heparinase I was added 4 mM WRK. The sample was allowed to incubate for 30 minutes at room temperature. An 10-fold excess of glycine methyl ester was added to quench the reaction. Then, the enzyme was denatured in 50 uL of 8 M urea/0.4 M ammonium carbonate and reduced with 5 mM dithiothreitol at 65° C., cooled to room temperature, and alkylated with 10 mM iodoacetamide for 15 minutes. The reaction was quenched with water by bringing the total reaction volume to 200 μL. To the above reaction, 4% (wt/wt) trypsin was added and the digestion was carried out at 37° C. for 24 hr. The proteolytic reaction was terminated by freezing at −20° C. The digest was separated using a gradient reverse-phase HPLC (2-80% acetonitrile in 0.1% TFA for 120 min). Tryptic peptides were monitored at 210, 277, and 320 nm and collected. Based on the peptide peaks monitored at 320 nm, 5 peaks were collected and sequenced using an on-line model 120 phenylthiohydantoin amino acid analyzer (Biopolymers Laboratory, Center for Cancer Research, Massachusetts Institute of Technology). To determine whether preincubation with calcium protected the enzyme from WRK modification, heparinase I was first incubated with 100 mM $CaCl_2$ at room temperature. Heparinase I digests in the absence of WRK-modification were included as controls.

Results:

WRK modification of specific amino acid residues forms covalent adducts that are stable to proteolytic mapping. In the presence of a suitable nucleophile, the WRK adduct absorbs in the near UV region (280-320 nm). Therefore, the tryptic map of heparinase I was monitored and peaks with absorbance higher than controls were collected and sequenced. The peptides eluting at 52 (td 52), 54 (td 54), 56.5 (td 56), 59 (td 59), and 95 min (td 95) were sequenced. The complete sequences of the peptides are as follows:

```
td52:
KAIIDNK;                        (SEQ ID NO:11 )

td54 and td59:
KNIAHDKVEKKDK;                  (SEQ ID NO: 12)

td56:
RVNVQADSAK;                     (SEQ ID NO: 13)

td95:
KFGIYRVGNSTVPVTYNLSGYSETAR      (SEQ ID NO:14 )
```

The late eluting peak, td 95, was found to correspond to the C-terminal region of heparinase I. Two of the four clustered peaks, td 54 and td 59, were found to correspond to a region of the protein which overlapped with the primary heparin binding site of heparinase I. The other two peptides, td 52 and td 56 were found to be small peptides in the N-terminal region of heparinase I, both of which contain aspartate residues.

Example 10

The Calcium Binding Domain of Heparinase I

Many studies have aimed at identifying consensus sequences for calcium coordinating motifs, and most of these have focused on a particular calcium-coordinating motif, the EF-hand, present in many calcium binding proteins [Kretsinger, R. H., *Cold Spring Harbor Symp. Quant. Biol.* 52:499-510 (1987); and Moncrief, N. D. et al., *J. Mol. Evol.* 30:522-562 (1990)]. We set out to determine whether any of the WRK-labeled peptides conformed to an EF-hand motif.

Table 3 lists the consensus sequence of the EF-hand calcium-coordinating motif. The canonical EF-hand consists of two α-helices interposed by a loop region which contains the calcium chelating amino acids. These amino acids, identified as X, Y, Z, -Y, -X, and -Z in Table 3 (six ligands) chelate calcium either through an oxygen atom of a side chain or through a carbonyl atom of the peptide backbone.

Examination of the modified tryptic peptides and comparison of their amino acid sequence with the consensus EF-hand calcium chelating sequence (Table 3) indicates that two of these modified peptides (viz., the C-terminal region of heparinase I and the region proximate to the heparin binding site of heparinase I) share similarities with a consensus EF-hand sequence and could potentially bind calcium.

The first site, hereafter referred to as CB-1, extends from $Glu^{207}$ to $Ala^{219}$ (Table 3) and is proximate to the heparin binding site which has also been shown to be critical for enzymatic functioning and contains $His^{203}$, a putative active site residue. Within CB-1, the potential calcium chelating amino acids include $Glu^{207}$, $Asp^{210}$, $Asp^{212}$, and $Thr^{216}$. The second site, hereafter referred to as CB-2, is at the C-terminus of heparinase I, extending from $T^{373}$ to $R^{384}$. Like CB-1, CB-2 contains amino acids that could potentially bind calcium. These include $Thr^{373}$, $Asn^{375}$, $Ser^{377}$, $Ser^{380}$, $Glu^{381}$. Importantly, both CB-1 and CB-2 are modified by WRK/glycine methyl ester.

To determine whether these peptides which were modified by WRK in the above experiment could be protected upon preincubation with calcium, 100 mM $Ca^{++}$ was added to heparinase I before the addition of WRK and subsequent digestion. Under these conditions, td 54, td 59, (corresponding to modification of CB-1) and td 95 (corresponding to modification of CB-2) were all protected from modification by preincubation with calcium, consistent with either CB-1, CB-2, or both being involved in calcium-binding by heparinase I.

TABLE 3

| EF-hand homology | 1 | | 3 | | 5 | 6 | 7 | 8 | 9 | | | 12 |
|---|---|---|---|---|---|---|---|---|---|---|---|---|
| | X | | Y | | Z | G | -Y | I | -X | | | -Z |
| aa$^a$ sequence | | | | | | | | | | | | |
| CB-1 | E | K | K | D | K | D | G | K | I | T | Y | V | A |
| CB-2 | V | T | Y | N | L | S | G | Y | S | E | T | A | R |
| Consensus | D | X | D | X | D | G | X | I | S | X | X | E | |
| | | | N | | N | | | | L | T | | | |
| | | | S | | | | | | V | G | | | |
| | | | | | | | | | | D | | | |
| | | | | | | | | | | N | | | |
| | | | | | | | | | | E | | | |

By a combination of biophysical and biochemical techniques, we have conclusively determined that heparinase I binds calcium. Furthermore, we have shown that the interaction between calcium and heparinase I is important for proper functioning of the enzyme and we have mapped the calcium-binding regions of heparinase I.

Fluorescence titration experiments have often been used to establish a specific interaction between calcium and a protein, including enzymes. We find that, in the presence of heparinase I, there is a fluorescence enhancement of terbium. This enhancement plateaus at a terbium:enzyme ratio of 10:1. To confirm that this interaction is specific for calcium, we find that terbium binding can be competed off by addition of an excess of calcium. Furthermore, terbium has a more pronounced effect on heparinase I activity than lutetium, a lanthanide with an ionic radius that does not as closely mimic that of calcium.

To corroborate the findings of the terbium study, we studied the interaction of WRK with heparinase I. We found that heparinase I is inhibited by WRK in a dose-dependent suggesting that WRK is modifying carboxylate residues important for proper enzymatic functioning. WRK is well-established in terms of its ability to modify glutamate and carboxylate amino acids [Keresztessy, Z. et al., *Arch. Biochem. Biophys.*, 314:142-152 (1994); Chauthaiwale, J. et al., *Biochim. Biophys. Acta.*, 1204:164-168 (1994); and Komissarov, A. A., et al., 270:10050-10055], which are especially prevalent in calcium coordinating motifs.

Several lines of evidence support the supposition that WRK is modifying carboxylate residues in heparinase I.

First, preincubation with calcium was found to protect heparinase I from inactivation by WRK in a dose-dependent fashion. Second, EDC, like WRK, was found to modify heparinase I. Finally, we mapped the residues that were modified by WRK. These mapping studies revealed that all the peptides contained carboxylate-containing amino acids. In addition, no peptides contained cysteine 135, indicating that, under these reaction conditions, WRK is specific for carboxylate-containing amino acids. Together, these findings support the notion that WRK is modifying carboxylate-containing amino acids in the calcium binding motifs of heparinase I.

The protection data also clearly highlights another point, that in the enzymatic function of heparinase I a ternary complex forms between heparin, calcium, and heparinase I. Preincubation with heparin and calcium protects heparinase I from modification by WRK almost entirely whereas preincubation with either alone does not.

Thus, taken together, the chemical modification and fluorescence data clearly shows that calcium binds to heparinase I, and that this interaction is critical for proper functioning of heparinase I. In addition, the mapping studies implicate two sites on heparinase I that could potentially bind calcium, either one or both of which are critical for complete enzymatic activity. Both of the sites contain a number of amino acids with oxygen-containing side chains, especially glutamate and aspartate, the preferred chelating motifs for the hard acid $Ca^{++}$ [Kretsinger, R. H., supra; and Moncrief N. D. et al., supra].

In summary, the experiments outlined in this study have shown that heparinase I binds calcium and has identified two sites, CB-1 and CB-2, which play a role in calcium binding and mediating heparinase I activity.

Heparinase I shares catalytic mechanism with pectate lyases (Pels). Pels are major virulence factors of plant pathogenic *Erwinia* sp., which depolymerize cell wall polygalacturonides in the presence of $Ca^{+2}$ and destroy the integrity of plant tissues (Kotoujansky, A. (1987) Annu. Rev. Phytopathol. 25, 405-430, Barras, F., Van Gijsegem, F., and Chatterjee, A. K. (1994) Annu. Rev. Phytopath. 32, 201-234, Collmer, A., and Keen, N. T. (1986) Annu. Rev. Phytopathol. 24, 383-409). Pels have an unusual "parallel β helix" structure, which is generated by coiling a β strand into a large, right-handed helix with an unusual stacking of asparagines on consecutive turns of parallel β helix core (Yoder, M. D., Lietzke, S. E., and Jurnak, F. (1993) Structure 1, 241-251). A putative calcium binding site consisting of asp-131, glu-166, and asp-170 was identified in Pel C (Yoder, M. D., Keen, N. T., Jurnak, F. (1993) Science 260, 1503-1507). Both Heparinase I and Pels degrade the polysaccharide through a typical β-elimination process, and both are $Ca^{+2}$ dependent for activities (Sasisekharan, R., Venkataraman, G., Godavarti, R., Ernst, S. E., Cooney, C. L. and Langer, R. (1996) J. Biol. Chem. 271, 3124-3131, Rexova-Benkova, L. and Markovic, O. (1976) Adv. Carbohydr. Chem. Biochem. 33,.323-381). Narsimha Rao et al. (Narsimha R A O, M., Kembhavi, A. A. and Pant, A. (1996) Biochem. J. 319, 159-164) reported that pectate lyase from *Fusarium moniliformae* depolymerizes its substrate, polygalacturonic acid, by abstraction of a proton from C-5 with a lysine residue, in which they proposed, by polarizing carboxyl group, $Ca^{+2}$ acidify the α-proton at C-5 and facilitate abstraction by the catalytic base of the enzyme. In the same study, one calcium ion was shown binding to lectate enzyme in a position analogous to that of Pel C.

A more general mechanism for enzyme-catalyzed β-elimination reactions of carboxylic acids was proposed by Gerlt and Gassman (Gerlt, J. A. and Gassman, P. G. (1991) J. Am. Chem. Soc. 114, 5928-5934). Although the α-proton of a carbon acid is more acidic than an aliphatic proton, the inductive effect of the carboxyl group is insufficient to decrease the pKa difference of the α-proton and the catalytic base. According to Gerlt and Gassman, the pKa of the carbon acid could be sufficiently decreased by an additional acid catalyst acting on the carbonyl or carboxyl group. They also proposed that upon binding to the active site of the enzyme, the anionic carboxylate group of the substrate will interact directly with a cation (either a metal ion and/or cationic amino acid functional group) and form the enol/enolate intermediate. A second more acidic amino acid is proposed to protonate the leaving β-substituent.

FIG. 1 shows a schematic model of the catalytic domain of heparinase I. Cysteine 135, exists in heparinase I as a thiolate anion due to a decreased pKa by surrounding positively charged residues, initiates the abstraction of the C-5 proton of uronate. In addition, histidine 203 and lysine 199 have been shown to play a role in the catalysis. The abstraction of the C-5 proton of heparinase by the base, presumed to be the thiolate anion of cysteine 135, would require a general acid catalyst acting on the carboxyl group. $Ca^{+2}$ could satisfy such a requirement by acting as a Lewis acid. Alternatively, lysine 199 could act as an acid catalyst to protonate the carbonyl oxygen in carboxyl group, and $Ca^{+2}$ could act to stabilize either deprotonated lysine 199 or cysteine 135. The polarization of the carboxyl group by $Ca^{+2}$ or lysine 199 would acidify the α-proton at C-5 and facilitate the abstraction by cysteine of heparinase I. Histidine could act as a second acidic catalyst to protonate the leaving β-substituent. The data presented herein indicate that both CB-1 and CB-2 bind calcium and the calcium binding in both sites is involved in the catalytical mechanism of heparinase I.

Cysteine 135, histidine 203 and lysine 199 were identified as catalytically critical residues. Here we show that $Ca^{+2}$ functions as an Lewis acid acting on the carboxyl group. Lysine 199 could act as an acid catalyst to protonate the carbonyl oxygen in carboxyl group. $Ca^{+2}$ could also act to stabilize either deprotonated lysine 199 or cysteine 135. The polarization of the carboxyl group by $Ca^{+2}$ or lysine would lower the pKa of α-proton at C-5 and facilitate the abstraction by cysteine of heparinase I. Histidine 203 would act as a second acidic catalyst to protonate the leaving β-substituent.

Example 11

Mutagenesis of Calcium Binding Site 1 (CB-1)

Previous study in our laboratory has shown the activity of heparinase I is a function of added calcium concentration and the enzyme activity increases with the addition of calcium up to 5 mM. Furthermore, as demonstrated above we have shown that calcium binds specifically to heparinase I, and that calcium binding is required for the enzyme activity. A systematic site-directed mutagenesis is used here to demonstrate that both calcium binding consensus sequences are important for heparinase I activity. More specifically, site-directed mutagenesis of D212A, G213A, T216A in CB-1 and N375, Y379, E381 A in CB-2 results in substantial reduction in enzyme activity (FIG. 1).

Methods:

Heparin (porcine intestinal mucosa, average molecular weight of 13 kDa and activity of >150 USP units/mg) was from Celcus (Cincinnati, Ohio). Urea, dithiothreitol (DTT) and acetonitrile were from Allied Chemicals (Deerfield, Ill.). Molecular weight standards were obtained from GIBCO BRL/Life Technologies (Md.) and BIO-RAD (CA). *E.coli*

BL21 (DE3) host was from Novagen, Wis. Molecular biology reagents and their sources are listed in the appropriate sections below.

The recombinant and mutant heparinase I were expressed without the putative *F. heparinum* leader sequence; i.e. as a construct (-L r-heparinase I) that reads Met-Gln22-Gln23-(Sasisekharan, R., Bulmer, M., Moremen, K. W., Cooney, C. L. and Langer, R., (1993) Proc. Natl. Acad. Sci. U.S.A. 90, 3660-3664). To facilitate purification, the heparinase I gene was expressed using the pET-15b system (Novagen, Wis.). This construct has a poly-histidine tag and a thrombin cleavage site in a 21 amino acid N-terminal leader sequence (Sasisekharan, R., Leckband, D., Godavarti, R., Venkatararnan, G., Cooney, C. L. and Langer, R. (1995) Biochemistry 34, 14441-14448).

Mutagenesis: The mutations were introduced via 16 cycle PCR, as described previously by the method of Higuchi (Higuchi, R. (1990) *PCR Protocols: A Guide to Methods and Applications*, Academic Press, Inc., San Diego, Calif.). All the mutant genes were cloned into pET-15b and were sequenced to verify the mutations as described previously (Sasisekharan, R., Leckband, D., Godavarti, R., Venkataraman, G., Cooney, C. L. and Langer, R. (1995) Biochemistry 34, 14441-14448).

Expression and Purification: The construct were transformed in BL21 (DE3) (Novagen), and the proteins were purified as described previously (Yang, V. C., Linhardt, R. J., Bernstein, H., Cooney, C. L. and Langer, R. (1985) J. Biol. Chem. 260, 1849-1857). SDS-PAGE was carried out using precast 12% gels and a Mini Protean II apparatus, and stained with the Silver Stain Plus kit (Sasisekharan, R., Leckband, D., Godavarti, R., Venkataraman, G., Cooney, C. L. and Langer, R. (1995) Biochemistry 34, 14441-14448).

Heparinase I Activity Assays: The UV 232 nm assay was used as described in Example 1. When measuring the enzyme activity as a function of heparin concentration, heparin concentrations varied from 0 to 4 mg/ml at a fixed calcium concentration of 5 mM (100 mM MOPS buffer/5 mM calcium acetate, pH 7.0). The data was then fit to an non-linear equation to determine Kcat and Km of heparinases I. Heparinase mutant activity was also investigated as a function of calcium concentration ranging from 0 to 10 mM. This data was also fit to an non-linear function to determine $K_{0.5}$ that is the calcium concentration at which half of the maximum enzyme activity was observed. Activity is expressed as IU-μmol product formed/min using $\varepsilon = -3800\text{-M}^{-1}\text{CM}^{-1}$.

HPLC of heparin oligosaccharides: Heparin (4 mg/ml) was incubated with -Lr-heparinase I and mutant enzymes in 100 mM MOPS, 5 mM calcium acetate buffer, pH 7.0, for 18 h. The reaction was then subjected to anion-exchange HPLC as described in Example 1. Oligosaccharide products were monitored and resolved at 232 nm, as described (Sasisekharan, R., Bulmer, M., Moremen, K. W., Cooney, C. L. and Langer, R., (1993) Proc. Natl. Acad. Sci. U.S.A. 90, 3660-3664).

Figure 2:
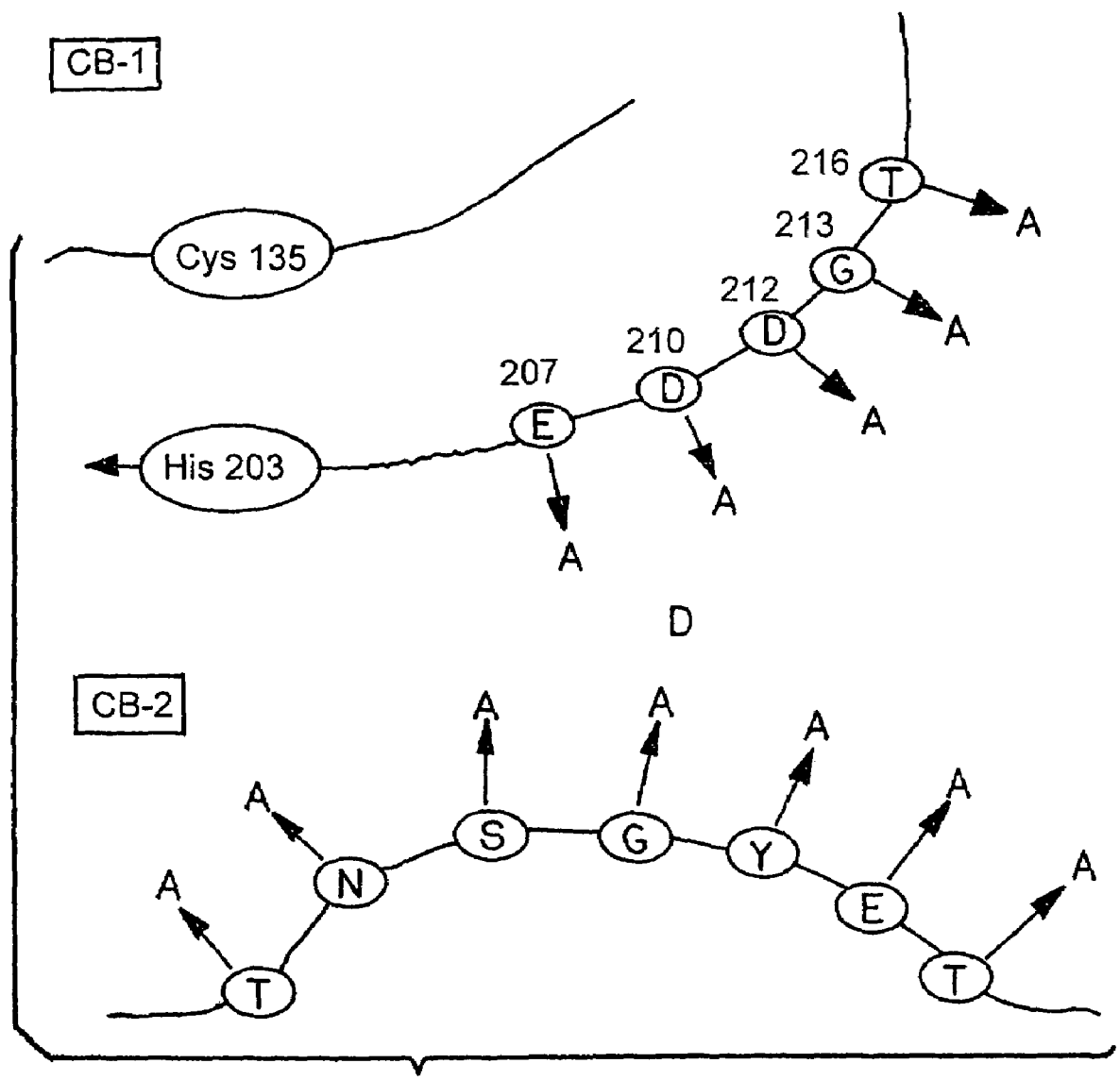
FIG. 2 is a schematic representation of the various heparinase I mutations undertaken for this study. Two putative calcium binding consensus sequences (CB-1 and CB-2) were chosen as targets for mutagenesis study. Based on alignment with classical EF-hand calcium binding motif (shown in Table 3), glutamate 207, aspartate 210, 212, glycine 213, and threonine 216 in CB-1 were first individually changed to alanines. Then double and triple mutants (D210A/D212A, E207A/D210A, E207A/D212A, D212A/T216A, G213A/T216A, E207A/D210A/D212A, D212A/G213A/T216A) were made to investigate the collective effect of mutations. In CB-2, double mutants G378A/Y379A and E381A/T382A were first made. Since the double mutants affected enzyme activity, glycine 378, tyrosine 379, glutamate 381 and threonine 382 were individually changed to alanines to examine the possibility of one of these residues having a dominant effect on enzyme activity. Based on homology to EF-hand, N375A, S377A, T373A were also made.

Results:

Various different mutations in heparinase I were made for this study. In CB-1, D204A, D210A, D212A, E207A, G213A and T216A were made first (FIG. 2). Later double mutants D210A/D212A, E207A/D210A, E207A/D212A, D212A/T216A, and G213A/T216A were made. Finally, triple mutants (E207A/D210A/D212A, D212A/G213A/T216A) of all putative calcium coordinating residues were made.

Table 4 lists the kinetic parameters obtained for wild-type r-heparinase I and all the mutant enzymes. E207A had no effect on enzyme activity with a Kcat value of 92 sec$^{-1}$.

D210A and D212A had a moderate effect on enzyme activity with a minor reduction in individual Kcat values (74 and 65 sec$^{-1}$, respectively). G213A and T216A affected enzyme activity significantly with about 3 and 2 fold decreases in Kcat values compared to that of wild-type r-heparinase I. Furthermore, mutants E207A/D210A, E207A/D212A, and E207A/D210A/D212A obtained no further reduction in enzyme activity compared to D210A, D212A and D210A/D212A, respectively, thus suggesting that glutamate 207 individually or jointly is not required for enzyme activity. Since aspartate 210, 212, glycine 213, and threonine 216 individually affected enzyme activity, the effect of combined mutations of these amino acids was examined. Double mutations D210A/D212A and G213A/T216A produced a more profound reduction in enzyme activity (4.5 and 5 fold decreases in Kcat values, respectively) than any of the single mutations. Triple mutant D212A/G213A/T216A decreased the enzyme activity by close to 5-fold. However, no further reduction in enzyme activity was observed for double mutant D212A/T216A as compared to the T216A single mutation.

Figure 3:
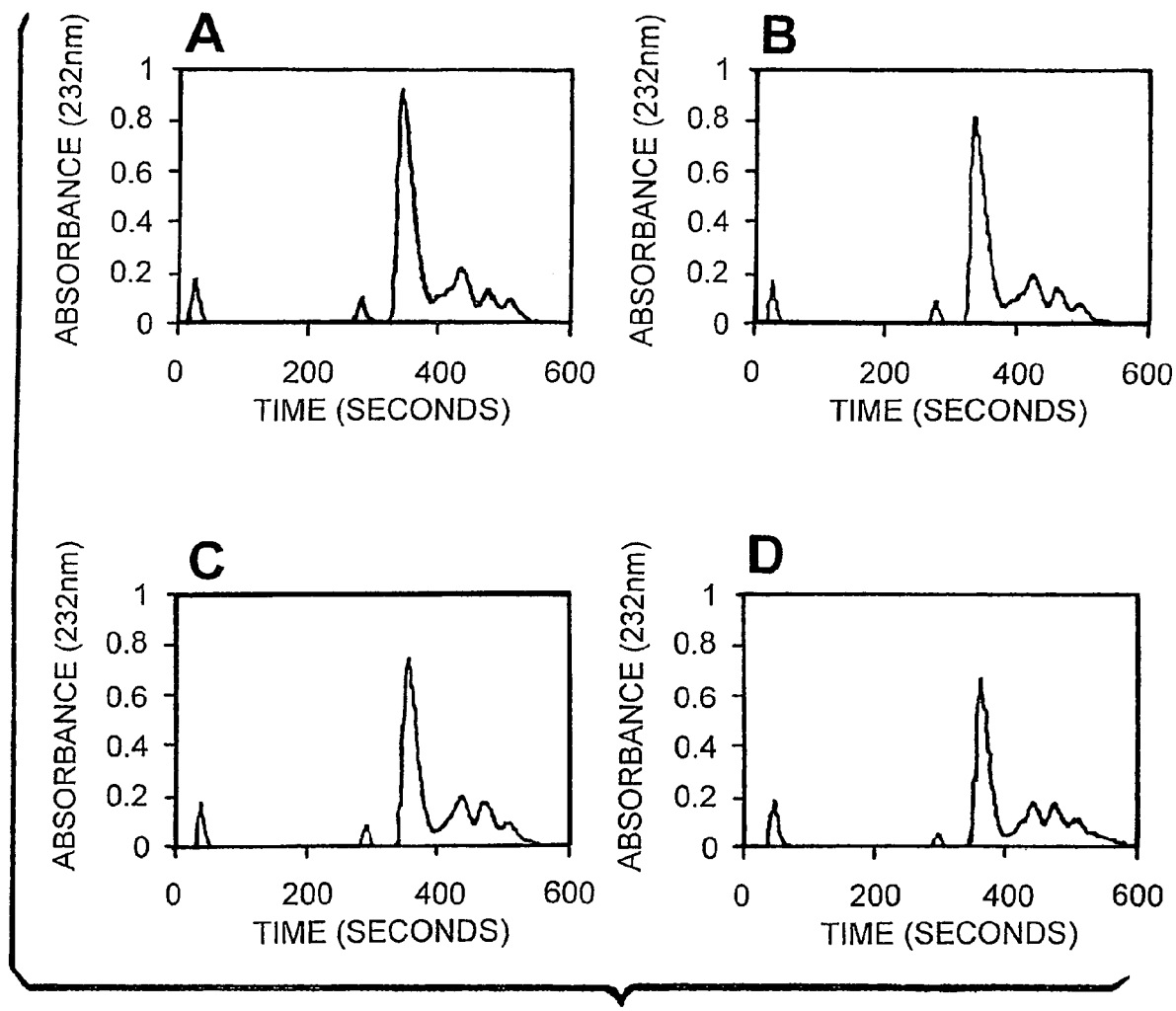
FIG. 3 is an anion-exchange HPLC separation of oligosaccharides products from CB-1 mutants. A shows the product profile of heparin degradation by wild-type r-heparinase I; B shows the product profile of heparin degradation by E207A/D210A; C shows the product profile of heparin degradation by E207A/D210A/D212A; D shows the product profile of heparin degradation by D212A/G213A/T216A.

All mutations in CB-1 resulted in increases in $K_{0.5}$ values, which represent the calcium concentrations at which half of the maximum enzyme activity was observed (Table 4). Furthermore, there is a strong correlation between loss of enzymatic activity and an increase in the $K_{0.5}$. These results suggest that CB-1 mutants lower the enzymatic activity of heparinase I primarily through lowering its calcium affinity. Moreover, this result is consistent with what is seen upon comparison of the exhaustive heparin digests of recombinant heparinase I and the mutants E207A/D212A, E207A/D210A/D212A, and D212A/G213A/T216A. Mutations in CB-1 do not affect the product profile of heparinase I but simply slow the enzyme's catalytic turnover rate (FIG. 3).

TABLE 4

| Enzyme | Kcat sec$^{-1}$ | $K_{0.5}$ μM | Km μM | $K_{0.5}$ μM | NaCl mM |
|---|---|---|---|---|---|
| -L | 92 | 270 | 3.94 | 270 | 482 ± 3 |
| E207A | 92 | 520 | 3.1 | 520 | 493 |
| D210A | 74 | 310 | 2.64 | 310 | 500 |
| D212A | 65 | 370 | 1.94 | 370 | 498 |
| G213A | 28 | 740 | 0.97 | 740 | 476 |
| T216A | 50 | 430 | 1.45 | 430 | 479 |
| E207A/D210A | 65 | 470 | 2.77 | 470 | 513 |
| D210A/D212A | 21 | 700 | 0.32 | 700 | 515 |
| E207A/D212A | 58 | 710 | 0.93 | 710 | 513 |
| D212A/T216A | 52 | 320 | 1.52 | 320 | 497 |
| G213A/T216 | 19 | 2200 | 0.83 | 2200 | 498 |
| E207/D210A/D212A | 25 | 810 | 0.73 | 810 | 540 |
| D212A/G213A/T216A | 20 | 730 | 3.16 | 730 | 495 |
| T373A | 85 | 50 | 0.96 | 50 | 480 |
| N375A | 10 | 60 | 0.88 | 60 | 490 |
| S377A | 71 | 50 | 2.74 | 50 | 486 |
| G378A | 41 | 80 | 0.74 | 80 | 489 |
| Y379A | 9 | 230 | 0.32 | 230 | 489 |
| E381A | 10 | 180 | 0.52 | 180 | 505 |
| T382A | 65 | 100 | 1.64 | 100 | 488 |
| G378A/Y379A | 9 | 90 | 0.31 | 90 | 489 |
| E381A/T382A | 10 | 180 | 1.75 | 180 | 505 |

Example 12

Mutagenesis of Calcium Binding Site 2 (CB-2)

Results:

In CB-2, double mutants G378A/Y379A and E381A/T382A were made first. If double mutations had an effect on catalytic activity, the residues were then individually changed to alanines to examine the possibility of one of the residues having a dominant effect on enzyme activity. Based on EF-hand motif consensus sequence (Table 3), threonine-373, asparagine-375 and serine-377 were also individually changed to alanines.

For the G378A/Y379A double mutant, the enzyme activity (kcat) was reduced by 10-fold. A similar effect was observed for double mutant E381A/T382A in which kcat was decreased by 9-fold. Since the joint alteration of glycine-378 and tyrosine-379 as well as glutamate-381 and threonine-382 affected heparinase I activity drastically, we subsequently investigated the effect of individually altering these residues to alanines to examine whether one mutation had a more pronounced effect than the other on heparinase I activity. When glycine-378 and threonine-382 were individually changed to alanines, their $k_{cat}$ values were decreased only by about 1 half (Table 4). However, the Y379A and E381 single mutations decreased enzyme activity (kcat) by about 10-fold, suggesting these residues are important for calcium binding and/or heparinase I activity.

Since threonine-373, asparagine-375 and serine-377 also are oxygen containing amino acids and conform to EF-hand motif consensus sequence (Table 3), we studied the effect of individually changing these amino acids on heparinase I activity as well. For the T373A and S377A mutants, no significant decrease in enzyme activity was observed (Table 4). Interestingly, a loss of dependence on calcium was observed on S377A mutation. Furthermore, N375 mutation decreased heparinase I activity (kcat) by more than 9-fold. Unlike the CB-1 mutants, all CB-2 mutants showed decreased $K_{0.5}$ values (Table 4).

Figure 4:
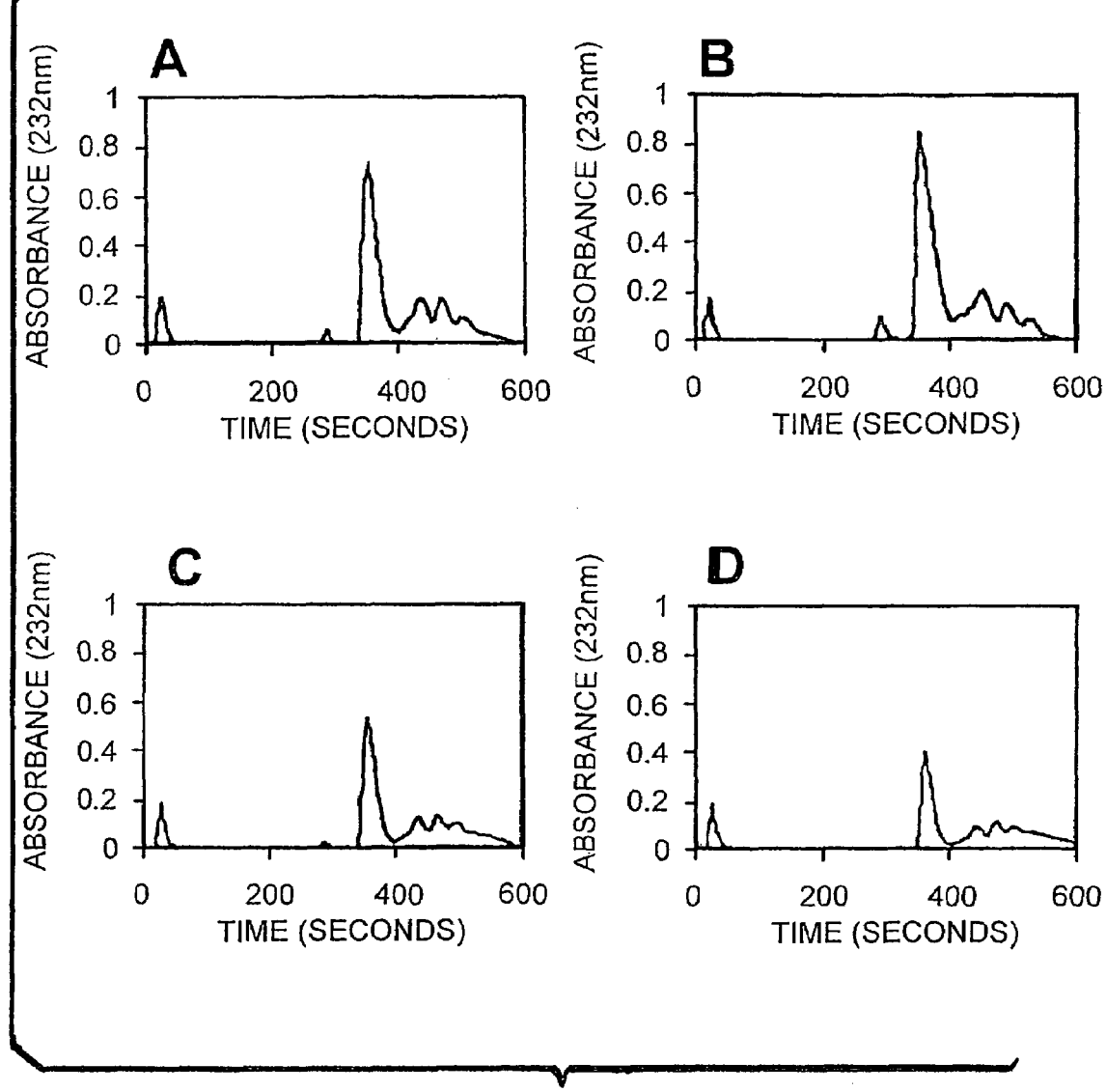
FIG. 4 is an anion-exchange HPLC separation of oligosaccharides products from CB-2 mutants. A shows the product profile of heparin degradation by N375A; B shows the product profile of heparin degradation by S377A; C shows the product profile of heparin degradation by G378A/Y379A. D shows the product profile of heparin degradation by E381A/T382A.

The product profiles for mutants N375A, S377A, G378A/Y379A, and E381A/T382A were similar to that of -L recombinant heparinase I, but, unlike CB-1 mutants, there was a lower amount of the major products (essentially di- and tetra-saccharides) and a greater fraction of digestion fragments larger than hexa-saccharide (FIG. 4). The presence of digestion fragments larger than hexasaccharide argues for a role for CB-2 in the processivity of heparinase I.

Example 13

Heparin Affinity Chromatography

Methods:

Heparin-POROS chromatography: About 30-40 µg of -L r-heparinase I and the various mutant enzymes were injected into a heparin POROS (4.6 mm×100) column (PerSeptive BioSystems, Framingham, Mass.) connected to BioCAD system (PerSeptive BioSystems). Proteins were eluted using a linear gradient of 0.1 M NaCl in 10 min (10 mM Tris, 1 mM EDTA pH 7.0) and monitored at 210 nm. EDTA was added to chelate any calcium ions that may be present in the buffers.

Results:

We have shown previously that, in the absence of calcium, native heparinase I from F. heparinum binds a heparin-POROS column and can be eluted at a salt concentration around 500 mM (Sasisekharan, R., Venkataraman, G., Godavarti, R., Ernst, S. E., Cooney, C. L. and Langer, R. (1996) J. Biol. Chem. 271, 3124-3131). However, it is necessary to point out that compared to other heparin-binding proteins, such as lipoprotein lipase or fibroblast growth factor, which elute at much higher salt concentrations of about 0.9-1.5 M NaCl (Klagsbrun, M. and Baird, A. (1991) Cell 67, 229-231, Hata, A., Ridinger, D., Sutherland, S., Emi, M., Shuhua, Z., Myers, R., Ren, K., Cheng, T., Inoue, I., Wilson, D., Iverius, P. and Lalouel, J. (1993) J. Biol. Chem. 268, 8447-8457), heparinase has a lower affinity for heparin (Sasisekharan, R., Venkataraman, G., Godavarti, R., Ernst, S. E., Cooney, C. L. and Langer, R. (1996) J. Biol. Chem. 271, 3124-3131). Heparin-POROS chromatography was used in this study to investigate whether the mutations affected heparin binding and hence altered the elution profiles. As shown in Table 4, wild-type r-heparinase I elutes at a salt concentration of about 482 mM. For CB-1, all mutants except for glycine 213 and threonine 216 eluted at a higher salt concentration. CB-2 did not have much effect. Interestingly, a direct overlapping correlation was observed between the salt concentration eluted and loss of negative charge of carboxyl groups in both CB-1 and CB-2. Salt concentrations of about 500 mM, 510 mM and 540 mM were able to neutralize 1, 2 and 3 negative charges respectively. D210A, E207A and D212A had one negative charge neutralized. D210A/D212A, E207A/D210A and D210A/D212A each had two negative charges neutralized. E207A/D210A/D212A had three negative charges neutralized. These observations are expected given the high negative charge of heparin and are consistent with the notion that a positively charged microenvironment in heparin binding sites is important for catalysis (as described above). Most of the CB-2 mutants (T373A, N375A, S377A, G378A, Y379A, T382A and G378/Y379A) also eluted at salt concentrations comparable to wild-type r-heparinase I (Table 4).

As mentioned above, heparin binding to heparinase is not a strong interaction, and the observed effects on heparin binding upon mutagenesis also is not dramatic. Under the experimental conditions tested, relative to wild-type heparinase I, mutant enzymes (D212A, N375A, Y379A, and E381A) decreased enzyme activity significantly while they showed increased affinity for heparin binding slightly. This suggests that heparin binding alone is not necessarily contributing to catalytic activity of heparinase I.

Therefore, all of the mutations involved in this study resulted in little to no change to the ability of heparinase I to bind heparin specifically, consistent with the earlier observation that heparinase I is able to bind heparin in the absence of calcium [Sasisekharan, R. et al., J. Biol. Chem. 271, 3124-3131 (1996)]. Together with the observation that all mutant enzymes retained enzymatic activities to a various extent, these results suggest the structure of the enzyme was unlikely to be perturbed upon site-specific mutagenesis.

Fluorescence Competition. To determine the effect of mutations in CB-1 and CB-2 on the ability of heparinase I to bind calcium, mutants with a dramatic drop in activity were tested for their ability to bind calcium. To accomplish this, we examined the ability of heparinase I and mutants to compete for free calcium with the calcium-chelating fluorescence probe rhod-5N. The fluorescence probe rhod-5N was dissolved and diluted in buffer A (10 mM MOPS and 100 mM KCl, pH 6.5). Buffer A and the water used in the study were run through a Chelex Resin column to remove trace amounts of calcium. In the absence of calcium, rhod-5N is not fluorescent, however upon binding calcium rhod-5N is fluorescent with an emission $\lambda_{max}$ of 576 nm. Before titration, rhod-5N and heparinase I were added to a quartz cuvette such that the final concentration of rhod-5N in the cuvette was 0.3 µM and heparinase I is 3 µM. To this solution was added aliquots of a calcium solution (20 mM) which had been previously equilibrated with 0.3 µM rhod-5N and 3 µM heparinase I. The stock was added such that the calcium concentration in the cuvette was 50, 100, 200, 500, 1000, 5000 µM. After allowing the solution to come to equilibrium, the sample was scanned from 560 nm to 600 nm with the excitation wavelength fixed at 561 nm. The plot of $I/I_{max}$ versus [Ca$^{++}$] was fitted to a non-linear equation to determine the apparent $K_d$ ($K_d'$) value. Thus, $K_d'$ values represent the apparent dissociation constants for the fluorescence probe rhod-5N. Control samples without heparinase I were included in the study.

(Halic) Results: The results of the kinetic analysis of CB-1 and CB-2 mutants raised the question of whether mutations in CB-2 mediate their effect through decreasing the affinity of heparinase I for calcium. To test this hypothesis directly we tested the ability of heparinase I and selected mutants to bind calcium using a fluorescence titration assay. Thus, the rationale for the fluorescence competition study is, using the calcium-chelating probe rhod-5N, to determine whether mutations in CB-1 or CB-2 affect the ability of heparinase I to bind calcium. In this study, we expected heparinase I to bind and compete for calcium with the fluorescence probe rhod-5N, and this competition is expected to lower the apparent affinity of rhod-5N for calcium. This decrease is reflected in an increase in the apparent $K_d$ ($K_d'$) values. Those mutants (E207A/D210A/D212A and D212A/G213A/T216A in CB-1, N375A, E381A, and G378A/Y379A in CB-2) that showed significant decrease in enzyme activity were chosen for fluorescence competition study. Table 6 shows the data derived from the fluorescence competition study. As we expected, wild type -L r-heparinase I binds calcium and competes the calcium off the fluorescence probe, resulting in a significantly increased $K_d'$ value. Triple mutants in CB-1 both have a diminished ability to compete for calcium and only lead to a minor increase in $K_d'$. The calcium binding ability of the CB-2 mutants lies between the wild type enzyme and the CB-1 mutants, suggesting a moderate reduction in the calcium binding ability. This result confirmed that both CB-1 and CB-2 are involved in calcium binding.

TABLE 6

Fluorescence competition study with wild-type recombinant heparinase I and mutant heparinases I

| Enzyme tested | $K_d'$ µM |
|---|---|
| -L | 206 |
| E207A/D210A/D212A | 151 |
| D212A/G213A/T216A | 116 |
| N375A | 216 |
| E381A | 175 |
| G378A/Y379A | 136 |

$K_d'$ eyaks 117 µM in the absence of enzyme. A lower $K_d'$ value means less binding of calcium by heparinase I The data presented herein confirms that both calcium binding sites in heparinase I, are involved in calcium binding and enzyme activity. Site directed mutagenesis studies in CB-1 identified $Asp^{210,212}$, $Gly^{213}$, and $Thr^{216}$ as important residues in calcium binding and enzyme activity; kinetic studies showed that these corresponding mutants, individual or combined, decreased the $K_{cat}$ value for the degradation of heparin by heparinase I and increased the $K_{0.5}$ value for calcium (Table 4). In addition, examining the $K_{cat}$ and the $K_{0.5}$ values for CB-1 mutants indicates a inverse correlation between the two values, suggesting that these mutants are lowering the enzyme activity of heparinase I through decreasing the binding of calcium to the enzyme. Fluorescence studies further confirmed that mutation of these residues to alanines led to a decreased calcium binding affinity in the CB-1 mutant enzymes (Table 6). Thus, taken together, these studies show that CB-1 binds calcium and that mutations in CB-1 mediate their affect, either entirely or in part, through decreasing the affinity of heparinase I for calcium.

One important observation of this study is that the latter half of CB-1 (including $Gly^{213}$ and $Thr^{216}$) appears to be more important than the first half of CB-1 ($Glu^{207}$, $Asp^{210,212}$) in calcium binding and enzyme activity. G213A, T216A, and G213A/T216A gave $K_{cat}$ values of 28, 50, and 19 $sec^{-1}$ compared to 92, 74, 65 and 25 $sec^{-1}$ obtained from E207A, D210A, D212A, and E207A/D210A/D212A. A similar trend was observed when comparing the $K_{0.5}$ values for calcium binding between these same mutant enzymes (Table 4).

A second observation derived from this study is that both CB-1 and CB-2 are involved in calcium binding; however, CB-2 plays a more prominent role in heparinase I activity. As shown in the fluorescence competition study, mutations in both CB-1 and CB-2 decreased the calcium binding affinity of heparinase I. On the other hand, mutations in CB-2 (N375A, Y379A, E381A, G378A/Y379A, and E381A/T382A) decreased enzyme activity drastically ($K_{cat}$ values were decreased by about 10 fold), while none of the mutations in CB-1 reduced enzyme activity by greater than 5 fold. Together with the $K_{0.5}$ data, these results indicate that mutations in CB-2 exerts a more pronounced effect on heparinase I, and thereby, the residues in CB-2 mediate their effect on heparinase I activity through interactions that are more complex than CB-1.

One interpretation of these results is that both CB-1 and CB-2 bind calcium; CB-1, which conforms more readily to the consensus calcium chelating motif, is a high affinity site. On the other hand, CB-2, which conforms less readily to the consensus calcium chelating motif, is presumably a lower affinity calcium binding site (Table 3). Mutations in CB-1 result in a CB-1 site with decreased affinity for calcium; however selected mutations in CB-2 completely eliminate its ability to bind calcium. In this case, the $K_{0.5}$ for CB-2 mutants is reflective of calcium binding to site 1.

This interpretation is consistent with three observations. First, in the fluorescence competition experiments, mutations in CB-2 resulted in an enzyme that was more like wild type heparinase I as compared to CB-1 mutants in competing calcium away from rhod-5N. This points to the fact that CB-1 binds calcium better than CB-2. Second, there is very little variation in the $K_{0.5}$ of the CB-2 mutants, consistent with the hypothesis that any mutation in CB-2 eliminates the ability of CB-2 to bind calcium. Also, the $K_{0.5}$ value for CB-2 mutants, ~50-90 µM, is probably reflective of the affinity of calcium for CB-1. Finally, the heparin binding properties of CB-2 mutants suggests that other possible effects, including unfolding of the protein, are not likely to occur here. These results point to two sites in heparinase I that bind calcium, a high affinity site (CB-1) and a lower affinity site (CB-2).

In summary, this study confirms the accompanying biochemical investigation into calcium binding to heparinase I. Further, we have identified key residues in CB-1 and CB-2 that are critical for proper functioning of heparinase I. Within CB-1 the latter half of the calcium-chelating sequence, including $Gly^{213}$, and $Thr^{216}$, are more critical for activity. Mutation of selected residues within this sequence affects both enzyme activity and calcium binding activity by heparinase I. Mutations within the second binding site, CB-2, have a greater effect on the enzymatic activity of heparinase I arguing for a more pronounced role for CB-2 as compared with CB-1 in the enzymatic activity of heparinase I.

Example 15

DEPC Inactivates Heparinase II in a Dose Dependent Fashion

Methods:

Chemicals and Materials. The chemical modification reagent diethylpyrocarbonate (DEPC) was purchased from Aldrich and used as received (Milwaukee, Wis.). All other reagents were obtained as described in Example 1.

Heparinase II Activity Assay. The assay was performed as described in Example 1.

Chemical Modification of Heparinase II with DEPC. (A) Decomposition of DEPC in Sodium Phosphate Buffer. At pH ranging from 5.5 to 8.0, 9.9 mM DEPC was incubated with different concentrations of sodium phosphate buffer. At fixed time intervals, a 10 µL aliquot was withdrawn to react with 10 mM imidazole (in 250 mM sodium phosphate buffer, pH 7.5). The concentration of intact DEPC remaining was measured from the increase in absorbance at 230 nm ($\epsilon$=3,000 cm$^{-1}$mM$^{-1}$). A second-order rate constant for the decomposition of DEPC in sodium phosphate buffer was derived for each pH.

(B) Inactivation of Heparinase II with DEPC. At pH ranging from 5.5 to 8.0, heparinase II (100 µg/ml) was incubated with DEPC in 50 mM sodium phosphate buffer at room temperature. At each pH, different concentrations of DEPC, ranging from 0.2 mM to 2.0 mM, were used to inactivate the enzyme. The 6.9 M DEPC stock solution was diluted in ethanol. The control mixtures contained an equivalent amount of ethanol instead of DEPC; the amount of ethanol added was less than 3% of the total volume and was determined not to affect significantly the enzymatic activity of heparinase II. At fixed time intervals, aliquots were withdrawn from the reaction mixtures and enzymatic activity determined by the UV 232 nm activity assay. The time course of inactivation was determined by monitoring the enzymatic activity retained after each time interval. The kinetics of DEPC inactivation of heparinase II were determined by plotting the natural log of percent activity versus an adjusted time term (to account for the decomposition of DEPC). Briefly, this adjusted time term (t') was calculated according to the following equation:

$$t' = \frac{1 - e^{k't}}{k'}$$

In this equation, k' is the first order rate constant for DEPC hydrolysis and t is the measured time after addition of DEPC to the heparinase II solution.

Results

DEPC readily inactivates heparinase II in a concentration-dependent manner. One complicating factor is that DEPC is unstable in aqueous solution. Therefore, the decomposition of inhibitor was investigated at a range of pH from 5-8. At each pH measured, the decomposition of DEPC followed first-order kinetics. To allow for the hydrolysis of DEPC, the inactivation data were plotted as the natural log of percentage activity versus an adjusted time factor (t'). For each concentration of DEPC used, this adjusted plot generated a straight line, indicating the reaction was pseudo first-order. The rate of inactivation of heparinase II was determined when both heparin and heparan sulfate were used as substrate.

Second-order rate constants were determined by re-plotting the pseudo first-order rate constants as a function of DEPC concentration. This analysis yields a straight line from which the second-order rate constant can be derived. With heparin as the substrate, the rate constant of inactivation was found to be 0.16 min$^{-1}$mM$^{-1}$; with heparan sulfate as the substrate, the rate constant was determined to be 0.24 min$^{-1}$mM$^{-1}$.

Example 16

Reactivation of DEPC-Modified Enzyme with Hydroxylamine

Methods:

Heparinase II (100 µg/mL) was incubated with 0.4 mM DEPC at pH 7.0 until its enzymatic activity was reduced to 50% of its initial value. Hydroxylamine was then immediately added to the reaction mixture to a final concentration of 500 mM and the reaction was incubated at room temperature for 8 hours. Every hour aliquots were withdrawn for the activity assay. The control mixture contained no DEPC but the same concentration of hydroxylamine to account for non-specific activity loss.

Results

DEPC is usually considered to be a histidine specific reagent. However, besides the imidazole ring of histidine, DEPC can also react with the nucleophilic side chains of other amino acids, such as tyrosine, lysine, and cysteine. To ensure that DEPC was histidine-specific under the conditions of this experiment, the ability of hydroxylamine to reverse the inactivation of heparinase II was studied. At pH 7.0, heparinase II was incubated with 0.4 mM DEPC until the enzymatic activity reached 50% of its initial value. Hydroxylamine (500 mM) was immediately added to the modified enzyme. By approximately 1.5 hours, the enzyme recovered about 80% of its initial activity. At later time points smaller incremental recoveries of enzyme activity were observed such that by 8 hours, the enzyme recovered about 90% of its initial value. Reactivation of the DEPC-modified enzyme indicated that neither cysteine nor lysine reacted to an appreciable extent with DEPC. In addition, reversibility of DEPC modification indicated that the reagent did not inactivate the enzyme by irreversibly altering heparinase II conformation.

To address whether tyrosine residues were modified by DEPC, the interaction of the tyrosine-specific reagent, tetranitromethane, with heparinase II was studied. Tetranitromethane, a tyrosine-specific modifying reagent, did not inactivate heparinase II, indicating that there are no tyrosine residues that are critical for activity that can be chemically modified. In addition, no change in the absorbance at 278 nm was observed when heparinase II was incubated with DEPC, which would be required if DEPC modified tyrosine residues.

Example 17

Determining pH of Histidine Residues Modified by DEPC

Methods:

Heparinase II (50 µg/mL) was pre-incubated with either 4 mg/mL heparin or 2 mg/mL heparan sulfate for 30 minutes prior to the addition of 0.8 mM DEPC. The time course of inactivation was determined with the heparinase II activity assay using both heparin and heparan sulfate as substrates.

Results

Different second-order rate constants of inactivation were determined using heparin or heparan sulfate as the substrate, indicating that different histidine(s) were critical for enzymatic activity towards heparin as compared with heparan sulfate. To investigate the chemical characteristics of the different histidines, the inactivation of heparinase II was determined as a function of pH. For the pH range of 5.5 to 8.0, a graph of the second-order rate constants of inactivation versus pH yielded a hyperbolic curve. A similar curve was generated with heparan sulfate as the substrate.

To confirm that histidines, and not lysines or cysteines, were being modified at pH 8, the reversibility of the reaction was determined using hydroxylamine. At pH 8, but not above, over 70% of activity could be restored with hydroxylamine. Therefore, up to pH 8, the interaction of DEPC with heparinases II involves only histidine modification.

Example 18

Determining Number of Histidine Residues Modified by DEPC

Methods:

Quantification of DEPC-modified residues of heparinase II was determined by difference spectra. At time zero, 2 mM DEPC was added to the sample cuvette containing heparinase II (825 μg/mL) in sodium phosphate buffer, pH 7.0. The change in absorbance at 240 nm was monitored every minute for 10 minutes. The number of modified residues was determined using $\epsilon=3,200\,M^{-1}cm^{-1}$ (Lundblad, R. L. (1995) *Techniques in Protein Modification*, CRC Press, Boca Raton). Heparinase II activity assays were completed under identical conditions with heparin as the substrate.

Results

To quantify the number of histidines that reacted with DEPC, the absorbance at 240 nm was followed as a function of time. The DEPC-histidine adduct, in a stoichiometry of 1:1, absorbs strongly in the near UV region ($\lambda_{max}$=240 nm, $\epsilon=3,200\,M^{-1}cm^{-1}$). After ten minutes, roughly three histidines are modified by DEPC. Interestingly, the absorbance increase is nearly linear, indicating that the three histidines which react with DEPC do so at nearly the same rate. This result is consistent with the DEPC inactivation data. Under the same conditions, an enzyme activity assay was completed to determine the effect on activity of the modification of the three histidine residues. After 10 minutes, there was loss of 90% of heparinase II enzymatic activity towards heparin and heparan sulfate substrates. Thus, there are three histidines that are more reactive towards DEPC than the rest of the histidines in heparinase II.

Example 19

Location of DEPC-modified Residues

Results

The chemical modification data points to three histidines being DEPC-reactive and essential for heparinase II activity. One possible role for either one, two, or all three of these histidines is that they are present in the active site of heparinase II. To attempt to understand whether any or all of the histidines are located at or near the active site of heparinase II, the enzyme was pre-incubated with either heparin or heparan sulfate before being subjected to chemical modification. Since the active site of the enzyme is presumably located in proximity to the binding site for heparin and/or heparan sulfate, pre-incubation with one or both of the substrates should serve to shield an active-site histidine from modification.

In the case of heparinase II pre-incubation with heparin, enzymatic activity towards heparan sulfate but not enzymatic activity towards heparin was lost upon addition of DEPC. Conversely, heparan sulfate was unable to protect heparinase II from DEPC-inactivation regardless of the substrate used. These results indicate that at least one and presumably more than one of the histidines are involved in the breakdown of heparin, while a separate histidine or histidines are involved in the breakdown of heparan sulfate.

Example 20

Identification of Active-Site Residues

Methods:

To determine which histidine residues were modified by DEPC, mapping studies using the protease Lys-C were completed. In one study, heparinase II (1 nmole) was incubated with 2 mM DEPC for twenty minutes. Unreacted DEPC was separated from the modified heparinase II by reverse phase HPLC (RPHPLC), the protein was concentrated by lyophilization, and digested with Lys-C under denaturing, reducing conditions.

To differentiate between histidines responsible for the breakdown of heparin versus those that are responsible for the breakdown of heparan sulfate, the modification and mapping studies were completed again but heparinase II was pre-incubated with 4 mg/mL of heparin or heparan sulfate. After 30 minutes, DEPC was added, the reaction was allowed to continue for 20 minutes, and heparinase II was digested by Lys-C under denaturing, reducing conditions.

Peptides derived from heparinase II digested by Lys-C, were separated by RPHPLC and monitored at 210, 240, and 277 nm. Peptide peaks not present in the control digest were collected and sequenced using an applied Biosystems Sequencer model 477 with an on-line model 120 PTH amino acid analyzer (Biopolymers Laboratory, MIT).

Results

To identify the histidines that are susceptible to DEPC modification, DEPC-modified heparinase II was digested with Lys-C. Since a DEPC-modified residue should be more hydrophobic, thus eluting later on a RPHPLC C4 column, the proteolytic digest of DEPC-modified heparinase II was compared with a control digest. Three peptides: 1d4, 1d5, and 1d6 were found to migrate differently in the digest of DEPC-modified heparinase II as compared with the control digest. All three of these peptides also had significant absorbance at 240 nm, as compared to non-adduct peptide peaks, indicative of a DEPC-histidine adduct. 1 d4, migrating at 45 minutes contained the sequence KRTIAH$^{451}$NSLLIYDPK SEQ ID NO: 8, with a modified residue in the sixty cycle (histidine 451). 1d5, migrating at 85 minutes, contained the sequence KEH$^{238}$LVAR SEQ ID NO: 9, with a modified residue in the sixth cycle (histidine 451). 1d5, migrating at 85 minutes, contained the sequence KEH$^{238}$LVAR,SEQ ID NO: 9 with a modified residue in the second cycle (histidine 238). Finally, 1d6, migrating at 87 minutes, contained the sequence KFWLLH$^{579}$SIEQPEIK SEQ ID NO: 10, with a modified residue in the fifth cycle (histidine 579).

To identify the histidine that was protected upon heparin pre-incubation of heparinase II, the mapping studies were completed in an identical fashion, except the enzyme was first pre-incubated with 4 mg/mL heparin for a period of 30 minutes. The Lys-C digest profile was identical to a profile of DEPC-modified heparinase II described above, except for the fact that 1d4, containing histidine 451, was absent. This result identifies histidine 451 as the essential histidine for the breakdown of heparin.

The chemical modification studies taken together with mapping studies point to histidines 238, 451 and 579 as being essential for heparinase II activity. These results also point to histidine 451 being an active site residue, responsible for the breakdown of heparin.

Example 21

Site-Directed Mutagenesis of the Histidines in Heparinase II

Methods:

Mutagenesis and cloning of recombinant mutant heparinases II. The 13 histidines were individually mutated to alanine by overlap extension PCR with 15 cycles. PCR products were cloned as described in Example 4. Expression, isolation, and purification of r-heparinase II and mutants in E. coli was performed as described in Example 4.

Results

Heparinase II contains 13 histidines in the mature protein. In an effort to corroborate the biochemical studies and determine which histidine residues were critical for heparinase II, each of the histidines was individually mutated into an alanine residue. The recombinant mutant heparinases II proteins were expressed, purified, and enzymatic activity of each mutant towards both heparin and heparan sulfate was assessed. The results are presented in Table 7. Consistent with the biochemical experiments, histidines 238, 451 and 579 when changed to alanines were inactive, towards both heparin and heparan sulfate, such that no enzymatic products could be detected by HPLC analysis of the saccharide products of heparinase II even after an 18 hour digest within the limits of this experimental procedure. While seven of the histidine mutants (H48A, H249A, H252A, H347A, H440A, H473A and H682A) displayed detectable enzymatic activity, two other histidine mutants (H406A and H408A), in addition to the H238A, H451A and H579A mutants showed complete loss of enzymatic activity.

TABLE 7

| MUTANT | ENZYMATIC ACTIVITY (+/−) TOWARDS SUBSTRATE: | |
|---|---|---|
| | HEPARIN | HEPARAN SULFATE |
| H48A | + | + |
| H202A | + | + |
| H238A | − | − |
| H249A | + | + |
| H252A | + | + |
| H347A | + | + |
| H406A | − | − |
| H408A | − | − |
| H440A | + | + |
| H451A | − | − |
| H473A | + | + |
| H579A | − | − |
| H682A | + | + |

The data described above has demonstrated through a combination of chemical modification and site-directed mutagenesis experiments that histidine residues play essential roles in heparinase II. Mature native heparinase II contains 13 histidine residues, and some of these residues may be essential in one of three ways: the histidine can be an important structural element, it can be involved in substrate binding, or it can be a catalytic residue.

The abbreviations used throughout the patent application include: recombinant heparinase II (r-heparinase II), heparin-like glycosaminoglycans (HLGAGs), extracellular matrix (ECM), bovine serum albumin (BSA), reverse phase high pressure liquid chromatography (RPHPLC), trifluoroacetic acid (TFA), sodium dodecyl sulfate polyacrylamide gel electrophoresis (SDS-PAGE), isopropyl β-D-thiogalactoside (IPTG), diothiothreitol (DTT), 5,5'-dithiobis-(2-nitrobenzoic acid) (DTNB), p(chloromercuri)benzoate (pCMB), N-ethylmaleimide (NEM), iodoacetimide (IAM), iodoacetic acid (IAA), 4-vinylpyridine (4-VP).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method, comprising:

cleaving a glycosaminoglycan, which comprises a disaccharide unit of uronic acid and hexosamine, where the uronic acid is either L-iduronic acid or D-glucuronic acid and the hexosamine is linked to the uronic acid by a 1→4 linkage, with the heparinase of any one of:

a substantially pure heparinase comprising a modified heparinase II, and a substantially pure heparinase comprising a modified heparinase I, wherein the modified heparinase II has the amino acid sequence of the mature peptide of SEQ ID NO: 2, wherein at least one amino acid residue is substituted and the substitution is selected from the group consisting of (a) a cysteine residue corresponding to position 348 substituted with a different amino acid than in native heparinase II; (b) a histidine residue corresponding to at least one of positions 238, 252, 347, 440, 451, and 579 substituted with alanine, serine, tyrosine, threonine, or lysine; and (c) a conservative substitution of a heparin-binding sequence residue corresponding to at least one of positions 446-451, and wherein the modified heparinase I has the amino acid sequence of the mature peptide of SEQ ID NO: 4, wherein at least one amino acid residue is substituted and the substitution is a seine residue corresponding to position 377 substituted with alanine, serine, tyrosine, histidine, threonine, or lysine; and determining the sequence of the glycosaminoglycan or a cleaved portion thereof.

2. The method of claim 1, wherein the heparinase is a modified heparinase II that has the amino acid sequence of the mature peptide of SEQ ID NO: 2, wherein at least one amino acid residue is substituted and the substitution is selected from the group consisting of (a) a cysteine residue corresponding to position 348 substituted with a different amino acid than in native heparinase II; (b) a histidine residue corresponding to at least one of positions 238, 252, 347, 440, 451, and 579 substituted with alanine, serine, tyrosine, threonine, or lysine; and (c) a conservative substitution of a heparin-binding sequence residue corresponding to at least one of positions 446-451.

3. The method of claim 1, wherein the heparinase is a modified heparinase II that has the amino acid sequence of the mature peptide of SEQ ID NO: 2, wherein the cysteine residue corresponding to position 348 is substituted with a different amino acid than in native heparinase II.

4. The method of claim 3, wherein the heparinase is a modified heparinase II that has the amino acid sequence of the mature peptide of SEQ ID NO: 2, wherein the cysteine residue corresponding to position 348 of SEQ ID NO: 2 is substituted with a residue selected from the group consisting of alanine, serine, tyrosine, histidine, threonine, and lysine.

5. The method of claim 4, wherein the heparinase is a modified heparinase II that has the amino acid sequence of the mature peptide of SEQ ID NO: 2, wherein the cysteine residue corresponding to position 348 of SEQ ID NO: 2 is substituted with alanine.

6. The method of claim 1, wherein the heparinase is a modified heparinase II that has the amino acid sequence of the mature peptide of SEQ ID NO: 2, wherein a histidine residue corresponding to at least one of positions 238, 252, 347, 440, 451, and 579 is substituted with alanine, serine, tyrosine, threonine, or lysine.

7. The method of claim 6, wherein the heparinase is a modified heparinase II that has the amino acid sequence of the mature peptide of SEQ ID NO: 2, wherein the histidine residue corresponding to position 440 is substituted with a residue selected from the group consisting of alanine, serine, tyrosine, threonine, and lysine.

8. The method of claim 1, wherein the heparinase is a modified heparinase II that has the amino acid sequence of the mature peptide of SEQ ID NO: 2, wherein the substitution is a conservative substitution of a heparin-binding sequence residue corresponding to at least one of positions 446-451.

9. The method of claim 1, wherein the heparinase is a modified heparinase I that has the amino acid sequence of the mature peptide of SEQ ID NO: 4, wherein the serine residue corresponding to position 377 of SEQ ID NO: 4 is substituted with a residue selected from the group consisting of alanine, serine, tyrosine, histidine, threonine, and lysine.

10. The method of claim 9, wherein the heparinase is a modified heparinase I that has the amino acid sequence of the mature peptide of SEQ ID NO: 4, wherein the serine residue corresponding to position 377 of SEQ ID NO: 4 is substituted with alanine.

11. The method of claim 1, wherein the glycosaminoglycan is a heparin.

12. The method of claim 1, wherein the glycosaminoglycan is a heparan sulfate.

13. The method of claim 1, wherein the heparinase is immobilized on a solid support.

* * * * *

UNITED STATES PATENT AND TRADEMARK OFFICE
CERTIFICATE OF CORRECTION

PATENT NO. : 7,560,106 B2  
APPLICATION NO. : 11/191144  
DATED : July 14, 2009  
INVENTOR(S) : Ram Sasisekharan et al.

Page 1 of 1

It is certified that error appears in the above-identified patent and that said Letters Patent is hereby corrected as shown below:

At column 1, lines 16-19, please delete

"This invention was made with government support under Grant No. NIH-1R01-GM57073 awarded by the National Institutes of Health. The government may have certain rights to the invention."

and insert

-- This invention was made with government support under grant number R01 GM57073 awarded by the NIH. The government has certain rights in this invention. --

Signed and Sealed this
Fourteenth Day of June, 2011

David J. Kappos
*Director of the United States Patent and Trademark Office*

UNITED STATES PATENT AND TRADEMARK OFFICE
CERTIFICATE OF CORRECTION

PATENT NO. : 7,560,106 B2  
APPLICATION NO. : 11/191144  
DATED : July 14, 2009  
INVENTOR(S) : Ram Sasisekharan et al.

Page 1 of 1

It is certified that error appears in the above-identified patent and that said Letters Patent is hereby corrected as shown below:

At column 1, lines 16-19, please delete

"This invention was made with government support under Grant No. NIH-1R01-GM57073 awarded by the National Institutes of Health. The government may have certain rights to the invention."

and insert

-- This invention was made with government support under Grant Number R01 GM057073 awarded by the National Institutes of Health. The government has certain rights in the invention. --

This certificate supersedes the Certificate of Correction issued June 14, 2011.

Signed and Sealed this  
Twenty-first Day of February, 2012

David J. Kappos  
*Director of the United States Patent and Trademark Office*